(12) United States Patent
Zeikus et al.

(10) Patent No.: US 7,750,135 B2
(45) Date of Patent: Jul. 6, 2010

(54) MOLECULAR DESIGN OF THERMOSTABLE ALCOHOL DEHYDROGENASE FOR SYNTHESIS FOR CHIRAL AROMATIC ALCOHOLS

(75) Inventors: J. Gregory Zeikus, Okemos, MI (US); Karla I. Ziegelmann-Fjeld, Lansing, MI (US); Claire Vieille, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 11/881,690

(22) Filed: Jul. 27, 2007

(65) Prior Publication Data

US 2008/0220487 A1    Sep. 11, 2008

(51) Int. Cl.
*C07H 21/04* (2006.01)
*C12P 21/06* (2006.01)
*C12N 9/04* (2006.01)

(52) U.S. Cl. ............... 536/23.2; 435/69.1; 435/190

(58) Field of Classification Search ............ None
See application file for complete search history.

(56) References Cited

OTHER PUBLICATIONS

Burdette et al (J. Biochem 1997, 326, 717-724).*
Chica et al. (Curr Opin Biotechnol. Aug. 2005; 16(4):378-84).*
Witkowski et al. (Biochemistry. Sep. 7, 1999; 38(36): 11643-50).*

* cited by examiner

*Primary Examiner*—Delia M Ramirez
*Assistant Examiner*—Md. Younus Meah
(74) *Attorney, Agent, or Firm*—Medlen & Carroll, LLP

(57) ABSTRACT

The present invention relates to compositions and methods utilizing thermostable and novel alcohol dehydrogenase enzymes for biosynthesizing chiral specific molecules for use as precursor molecules in synthesizing pharmaceutical compounds. Particularly, in preferred embodiments, the invention relates to directed engineering of an enzymatic catalytic site of an alcohol dehydrogenase enzyme gene for enhancing enantioselectivity for (S)-enantiomer substrate catalytic activity for providing aryl (S)-enantiomer products in stereomeric excess.

3 Claims, 16 Drawing Sheets

A.

B.

SEQ ID NO:01

Sequence of TeSADH W110A, variant 1

MKGFAMLSIGKVGWIEKEKPAPGPFDAIVRPLAVAPCTSDIHTVFEGAIGERHNM
ILGHEAVGEVVEVGSEVKDFKPGDRVVVPAITPDWRTSEVQRGYHQHSGGMLA
GA<u>A</u>KFSNVKDGVFGEFFHVNDADMNLAHLPKEIPLEAAVMIPDMMTTGFHGAEL
ADIELGATVAVLGIGPVGLMAVAG<u>D</u>KLRGAGRIIAVGSRPVCVDAAKYYGATDI
VNYKDGPIESQIMNLTEGKGVDAAIIAGGNADIMATAVKIVKPGGTIANVNYFGE
GEVLPVPRLEWGCGMAHKTIKGGLCPGGRLRMERLIDLVFYKRVDPSKLVTHVF
RGFDNIEKAFMLMKDKPKDLIKPVVILA

SEQ ID NO:02

Sequence of TeSADH W110A, variant 1

Atgaaaggttttgcaatgctcagtatcggtaaagttggctggattgagaaggaaaagcctgctcctggcccatttgatgctattgta
agacctctagctgtggccccttgcacttcggacattcataccgttttgaaggagccattggcgaaagacataacatgatactcggt
cacgaagctgtaggtgaagtagttgaagtaggtagtgaggtaaaagattttaaacctggtgatcgcgttgttgtgccagctattacc
cctgattggcggacctctgaagtacaaagaggatatcaccagcactccggtggaatgctggcaggcNNNaaattttcgaatgt
aaaagatggtgttttggtgaattttttcatgtgaatgatgctgatatgaatttagcacatctgcctaaagaaattccattggaagctgc
agttatgattcccgatatgatgaccactggttttcacggagctgaactggcagatatagaattaggtgcgacggtagcagttttggg
tattggcccagtaggtcttatggcagtcgctggtNNNaaattgcgtggagccggaagaattattgccgtaggcagtagaccag
tttgtgtagatgctgcaaaatactatggagctactgatattgtaaactataaagatggtcctatcgaaagtcagattatgaatctaact
gaaggcaaaggtgtcgatgctgccatcatcgctggaggaaatgctgacattatggctacagcagttaagattgttaaacctggtg
gcaccatcgctaatgtaaattattttggcgaaggagaggttttgcctgttcctcgtcttgaatgggttgcggcatggctcataaaac
tataaaaggcgggctatgccccggtggacgtctaagaatggaaagactgattgaccttgttttttataagcctgtcgatccttctaag
ctcgtcactcacgttttccagggatttgacaatattgaaaaagcctttatgttgatgaaagacaaaccaaaagacctaatcaaacct
gttgtaatattagca For inserting an A at 110: 328NNN = gct or gcc or gca or gcg For inserting a D at 186: 556NNN = Gat or Gac

FIG. 9

SEQ ID NO:03

Sequence of TeSADH W110A, variant 2

MKGFAMLSIGKVGWIEKEKPAPGPFDAIVRPLAVAPCTSDIHTVFEGAIGERHNM
ILGHEAVGEVVEVGSEVKDFKPGDRVVVPAITPDWRTSEVQRGYHQHSGGMLA
GAKFSNVKDGVFGEFFHVNDADMNLAHLPKEIPLEAAVMIPDMMTTGFHGAEL
ADIELGATVAVLGIGPVGLMAVAGAKLRGAGRIIAVGSRPVCVDAAKYYGATDI
VNYKDGPIESQIMNLTEGKGVDAAIIAGGNADIMATAVKIVKPGGTIANVNYFGE
GEVLPVPRLEWGCGMAHKTIKGGLCPGGRLRMERLIDLVFYKRVDPSKLVTHVF
RGFDNIEKAFMLMKDKPKDLIKPVVILA

SEQ ID NO:04

Sequence of TeSADH W110A, variant 2

Atgaaaggttttgcaatgctcagtatcggtaaagttggctggattgagaaggaaaagcctgctcctggcccatttgatgctattgta
agacctctagctgtggccccttgcacttcggacattcataccgtttttgaaggagccattggcgaaagacataacatgatactcggt
cacgaagctgtaggtgaagtagttgaagtaggtagtgaggtaaaagattttaaacctggtgatcgcgttgttgtgccagctattacc
cctgattggcggacctctgaagtacaaagaggatatcaccagcactccggtggaatgctggcaggcNNNaaattttcgaatgt
aaaagatggtgttttggtgaattttttcatgtgaatgatgctgatatgaatttagcacatctgcctaaagaaattccattggaagctgc
agttatgattcccgatatgatgaccactggttttcacggagctgaactggcagatatagaattaggtgcgacggtagcagttttggg
tattggcccagtaggtcttatggcagtcgctggtgccaaattgcgtggagccggaagaattattgccgtaggcagtagaccagttt
gtgtagatgctgcaaaatactatggagctactgatattgtaaactataaagatggtcctatcgaaagtcagattatgaatctaactga
aggcaaaggtgtcgatgctgccatcatcgctggaggaaatgctgacattatggctacagcagttaagattgttaaacctggtggc
accatcgctaatgtaaattattttggcgaaggagaggttttgcctgttcctcgtcttgaatggggttgcggcatggctcataaaactat
aaaaggcgggctatgccccggtggacgtctaagaatggaaagactgattgaccttgttttttataagcctgtcgatccttctaagct
cgtcactcacgttttccagggatttgacaatattgaaaaagcctttatgttgatgaaagacaaaccaaaagacctaatcaaacctgtt
gtaatattagca For inserting an A at 110: 328NNN = gct or gcc or gca or gcg

SEQ ID NO:05

TeSADH Y267G Protein Sequence

MKGFAMLSIGKVGWIEKEKPAPGPFDAIVRPLAVAPCTSDIHTVFEGAIGERHNM
ILGHEAVGEVVEVGSEVKDFKPGDRVVVPAITPDWRTSEVQRGYHQHSGGMLA
GWKFSNVKDGVFGEFFHVNDADMNLAHLPKEIPLEAAVMIPDMMTTGFHGAEL
ADIELGATVAVLGIGPVGLMAVAGDKLRGAGRIIAVGSRPVCVDAAKYYGATDI
VNYKDGPIESQIMNLTEGKGVDAAIIAGGNADIMATAVKIVKPGGTIANVN<u>G</u>FGE
GEVLPVPRLEWGCGMAHKTIKGGLCPGGRLRMERLIDLVFYKRVDPSKLVTHVF
RGFDNIEKAFMLMKDKPKDLIKPVVILA

SEQ ID NO:06

TeSADH Y267G Nucleotide Sequence

Atgaaaggttttgcaatgctcagtatcggtaaagttggctggattgagaaggaaaagcctgctcctggcccatttgatgctattgta
agacctctagctgtggccccttgcacttcggacattcataccgtttttgaaggcgccattggcgaaagacataacatgatactcggt
cacgaagctgtaggtgaagtagttgaagtaggtagtgaggtaaaagattttaaacctggtgatcgcgttgttgtgccagctattacc
cctgattggcggacctctgaagtacaaagaggatatcaccagcactccggtggaatgctggcaggctggaaattttcgaatgtaa
aagatggtgttttggtgaattttttcatgtgaatgatgctgatatgaatttagcacatctgcctaaagaaattccattggaagctgcag
ttatgattcccgatatgatgaccactggttttcacggagctgaactggcagatatagaattaggtgcgacggtagcagttttgggtat
tggcccagtaggtcttatggcagtcgctggtgacaaattgcgtggagccggaagaattattgccgtaggcagtagaccagtttgt
gtagatgctgcaaaatactatggagctactgatattgtaaactataaagatggtcctatcgaaagtcagattatgaatctaactgaag
gcaaaggtgtcgatgctgccatcatcgctggaggaaatgctgacattatggctacagcagttaagattgttaaacctggtggcac
catcgctaatgtaaat<u>ggt</u>tttggcgaaggagaggttttgcctgttcctcgtcttgaatggggttgcggcatggctcataaaactata
aaaggcgggctatgccccggtggacgtctaagaatggaaagactgattgaccttgttttttataagcgtgtcgatccttctaagctc
gtcactcacgttttccggggatttgacaatattgaaaaagcctttatgttgatgaaagacaaaccaaaagacctaatcaaacctgttg
taatattagca

SEQ ID NO:07

Sequence of TeSADH (taken from the *T. ethanolicus* 39E draft genome sequence)

MMKGFAMLSIGKVGWIEKEKPAPGPFDAIVRPLAVAPCTSDIHTVFEGAIGERHN
MILGHEAVGEVVEVGSEVKDFKPGDRVVVPAITPDWRTSEVQRGYHQHSGGML
AGWKFSNVKDGVFGEFFHVNDADMNLAHLPKEIPLEAAVMIPDMMTTGFHGAE

LADIELGATVAVLGIGPVGLMAVAGAKLRGAGRIIAVGSRPVCVDAAKYYGATD
IVNYKDGPIESQIMNLTEGKGVDAAIIAGGNADIMATAVKIVKPGGTIANVNYFG
EGEVLPVPRLEWGCGMAHKTIKGGLCPGGRLRMERLIDLVFYKRVDPSKLVTHV
FRGFDNIEKAFMLMKDKPKDLIKPVVILA

SEQ ID NO:08

*Thermoanaerobacter ethanolicus* secondary-alcohol dehydrogenase TeSADH atgaaaggttttgcaatgctcagtatcggtaaagttggctggattgagaaggaaaagcctgctcctggcccatttgatgctattgta
agacctctagctgtggccccttgcacttcggacattcataccgtttttgaaggagccattggcgaaagacataacatgatactcggt
cacgaagctgtaggtgaagtagttgaagtaggtagtgaggtaaaagattttaaacctggtgatcgcgttgttgtgccagctattacc
cctgattggcggacctctgaagtacaaagaggatatcaccagcactccggtggaatgctggcaggctggaaattttcgaatgtaa
aagatggtgttttggtgaattttttcatgtgaatgatgctgatatgaatttagcacatctgcctaaagaaattccattggaagctgcag
ttatgattcccgatatgatgaccactggttttcacggagctgaactggcagatatagaattaggtgcgacggtagcagttttgggtat
tggcccagtaggtcttatggcagtcgctggtgccaaattgcgtggagccggaagaattattgccgtaggcagtagaccagtttgt
gtagatgctgcaaaatactatggagctactgatattgtaaactataaagatggtcctatcgaaagtcagattatgaatctaactgaag
gcaaaggtgtcgatgctgccatcatcgctggaggaaatgctgacattatggctacagcagttaagattgttaaacctggtggcac
catcgctaatgtaaattatttggcgaaggagaggttttgcctgttcctcgtcttgaatgggttgcggcatggctcataaaactataa
aaggcgggctatgccccggtggacgtctaagaatggaaagactgattgaccttgtttttttataagcctgtcgatccttctaagctcg
tcactcacgttttccagggatttgacaatattgaaaaagcctttatgttgatgaaagacaaaccaaaagacctaatcaaacctgttgt
aatattagca

SEQ ID NO:09

Demonstration for numbering amino acid positions in a sequence, for example, TeSADH

```
         10         20         30         40         50         60
MKGFAMLSIG KVGWIEKEKP TPGPFDAIVR PLAVAPCTSD VHTVFEGAIG ERHNMILGHE 70         80         90        100        110        120
AVGEVVEVGS EVKDFKPGDR VVVPAITPDW RTSEVQRGYH QHSGGMLAGW KFSNIKDGVF 130        140        150        160        170        180
GEFFHVNDAD MNLAHLPKEI PLEAAVMIPD MMTTGFHGAE LAEIELGATV AVLGIGPVGL
```

FIG. 9 CONT

```
          190        200        210        220        230        240
MAVAGAKLRG AGRIIAVGSR PVCVDAAKYY GATDIVNYKN GPIESQIMDL TEGKGVDAAI 250        260        270        280        290        300
IAGGNADIMA TAVKIVKPGG TIANVNYFGE GDVLPVPRLE WGCGMAHKAI KGGLCPGGRL 310        320        330        340        350
RMERLIDLVF YKRVDPSKLV THVFQGFDNI EKALMLMKDK PKDLIKPVVI LA
```

SEQ ID NO:10

*Thermoanaerobacter brockii* alcohol dehydrogenase CAA46053

MKGFAMLSIGKVGWIEKEKPAPGPFDAIVRPLAVAPCTSDIHTVFEGAIGERHNM
ILGHEAVGEVVEVGSEVKDFKPGDRVVVPAITPDWRTSEVQRGYHQHSGGMLA
GWKFSNVKDGVFGEFFHVNDADMNLAHLPKEIPLEAAVMIPDMMTTGFHGAEL
ADIELGATVAVLGIGPVGLMAVAGAKLRGAGRIIAVGSRPVCVDAAKYYGATDI
VNYKDGPIESQIMNLTEGKGVDAAIIAGGNADIMATAVKIVKPGGTIANVNYFGE
GEVLPVPRLEWGCGMAHKTIKGGLCPGGRLRMERLIDLVFYKRVDPSKLVTHVF
RGFDNIEKAFMLMKDKPKDLIKPVVILA

FIG. 9 CONT

SEQ ID NO:11

*Thermoanaerobacter brockii* alcoholde hydrogenase CAA46053 atgaaaggttttgcaatgctcagtatcggtaaagttggctggattgagaaggaaaagcctgctcctggcccatttgatgctattgta agacctctagctgtggccccttgcacttcggacattcataccgttttgaaggcgccattggcgaaagacataacatgatactcggt cacgaagctgtaggtgaagtagttgaagtaggtagtgaggtaaaagattttaaacctggtgatcgcgttgttgtgccagctattacc cctgattggcggacctctgaagtacaaagaggatatcaccagcactccggtggaatgctggcaggctggaaattttcgaatgtaa aagatggtgttttggtgaatttttcatgtgaatgatgctgatatgaatttagcacatctgcctaaagaaattccattggaagctgcag ttatgattcccgatatgatgaccactggttttcacggagctgaactggcagatatagaattaggtgcgacggtagcagttttgggtat tggcccagtaggtcttatggcagtcgctggtgccaaattgcgtggagccggaagaattattgccgtaggcagtagaccagtttgt gtagatgctgcaaaatactatggagctactgatattgtaaactataaagatggtcctatcgaaagtcagattatgaatctaactgaag gcaaaggtgtcgatgctgccatcatcgctggaggaaatgctgacattatggctacagcagttaagattgttaaacctggtggcac catcgctaatgtaaattattttggcgaaggagaggttttgcctgttcctcgtcttgaatggggttgcggcatggctcataaaactataa aaggcgggctatgccccggtggacgtctaagaatggaaagactgattgaccttgttttttataagcgtgtcgatccttctaagctcg tcactcacgttttccggggatttgacaatattgaaaaagcctttatgttgatgaaagacaaaccaaaagacctaatcaaacctgttgt aatattagcataa

SEQ ID NO:12

Chain B, *Equus caballus* (horse) Alcohol Dehydrogenase (E.C.1.1.1.1) (Ee Isozyme)
HRSADHE and PDB ID: 1HLD -B STAGKVIKCKAAVLWEEKKPFSIEEVEVAPPKAHEVRIKMVATGICRSDDHVVS
GTLVTPLPVIAGHEAAGIVESIGEGVTTVRPGDKVIPLFTPQCGKCRVCKHPEGNF
CLKNDLSMPRGTMQDGTSRFTCRGKPIHHFLGTSTFSQYTVVDEISVAKIDAASP
LEKVCLIGCGFSTGYGSAVKVAKVTQGSTCAVFGLGGVGLSVIMGCKAAGAARI
IGVDINKDKFAKAKEVGATECVNPQDYKKPIQEVLTEMSNGGVDFSFEVIGRLDT
MVTALSCCQEAYGVSVIVGVPPDSQNLSMNPMLLLSGRTWKGAIFGGFKSKDSV
PKLVADFMAKKFALDPLITHVLPFEKINEGFDLLRSGESIRTILTF

SEQ ID NO:13

Chain B, *Equus caballus* (horse) Alcohol Dehydrogenase (E.C.1.1.1.1) (Ee Isozyme)
HRSADHE 1 gaaaacggca tcatgagcac agcaggaaaa gtaataaaat gcaaagcggc tgtgctgtgg

FIG. 9 CONT

```
  61 gaggaaaaga aaccattttc catcgaggag gtggaggttg caccccgaa ggcccatgaa
 121 gtccgtataa agatggtggc cacaggaatt tgtcgctcag atgaccacgt ggttagtgga
 181 acccttgtca cacctcttcc tgtgatcgca ggccatgagg cagcgggcat tgtggagagc
 241 attggagaag gcgtcactac agtaagacca ggtgataaag tcatcccact ctttactccc
 301 cagtgtggaa aatgcagggt ttgtaagcac cctgaaggca acttctgctt gaaaaatgat
 361 ctgagcatgc ctcggggaac catgcaggat ggtaccagca ggttcacctg cagagggaag
 421 cccatccacc acttccttgg caccagcacc ttctcccagt acaccgtggt ggacgagatc
 481 tcagtggcca agatcgatgc ggcctcaccg ctggagaaag tctgtctcat tggctgtgga
 541 ttttctactg gttatgggtc tgcagtcaag gttgccaagg tcacccaggg ctccacctgt
 601 gccgtgtttg gccttggagg agtgggcctg tctgttatca tgggctgtaa agcagccgga
 661 gcggccagga tcattggggt ggacatcaac aaagacaagt ttgcaaaggc caaagaagtg
 721 ggtgccactg agtgtgtcaa ccctcaggac tacaagaaac ccatccagga ggtgctgaca
 781 gaaatgagca atggaggtgt ggattttttcc tttgaagtca ttggtcggct cgacactatg
 841 gtgactgcct tgtcatgctg tcaagaagca tatggtgtga gcgtcattgt gggagtacct
 901 cctgattccc aaaatctctc tatgaatcct atgttgctac tgagtggacg tacctggaaa
 961 ggagctattt ttggcggttt taagagtaaa gattctgtcc ccaaacttgt ggccgatttt
1021 atggctaaaa agtttgcact ggatccttta atcacccatg ttttacccttt tgaaaaaata
1081 aatgaaggat ttgacctgct tcgctctgga gagagtatcc gtaccatcct gacgttttga
1141 gaccatacaa atgtctgcac ttgtagccgt cttctggctc tctatcctc tggatcatca
1201 gccaaacgac atcaataatt ctgttcctca aagatgctat taatagttac cgctgggagc
1261 tttctaaaag aaacaaaaat tgatgtgaag tcacttttca agcaaacgtt taaaatccaa
1321 gtgagagcta gaggaaccat cagctgggta actgagccca ctaaactttc cttcttaatc
1381 attctcctca cgttgaatcc tgtcaccttt cccattgagg gaaggcatgt gttttgactt
1441 cttgcatgat ttgtatcttg ggcacccta gtattgaagc cgggggtggg gggtcctcat
1501 gatacttgcc cctcagcata cacgtgatgg gctattgtgc tctaagcctt ctccttctac
1561 atgcatttcc actgtctgta tttgccttt gatgaaggta acaaggtcgc acagtaaaat
1621 acagtctgtg aaaagatact ctcggattta taagtggaga aggtctagaa cttctaaatg
1681 cagggaattt cttaggaaaa tgtcatacat ctttataagg tggagggaaa tgtctttatc
1741 gcttttatac tgttggcagt g
```

SEQ ID NO:14

FIG. 9 CONT

5'-ATCAATATGTCATATGATGAAAGGTTTTGCAATGC

SEQ ID NO:15

5'-CATTCGAAATTTCGCGCCTGCCAGC

SEQ ID NO:16

5'-AGGACCATCTTTAGGGTTTACAATATC

SEQ ID NO:17

5'-GCTGGCAGGCGCGAAATTTCGAATG

SEQ ID NO:18

5'- GATATTGTAAACCCTAAAGATGGTCCT

SEQ ID NO:19

5'-GTCATCTCGAGTGCTAATATTACAACAGGTTTG

FIG. 9 CONT

MOLECULAR DESIGN OF THERMOSTABLE ALCOHOL DEHYDROGENASE FOR SYNTHESIS FOR CHIRAL AROMATIC ALCOHOLS

Aspects of this disclosure were accomplished in part with government support under Grant Award MCB-0445750 and 0445511 from the National Science Foundation. As such, the United States Government may have certain rights.

FIELD OF THE INVENTION

The present invention relates to compositions and methods utilizing thermostable and novel alcohol dehydrogenase enzymes for biosynthesizing chiral specific molecules for use as precursor molecules in synthesizing pharmaceutical compounds. Particularly, in preferred embodiments, the invention relates to directed engineering of an enzymatic catalytic site of an alcohol dehydrogenase enzyme gene for enhancing catalytic efficiency, and enantioselectivity, for (S)-enantiomer substrate catalytic activity, and for providing aryl (S)-enantiomer products in stereomeric excess.

BACKGROUND

Chiral aromatic alcohols are important building blocks for a variety of high-value chemicals including, but not limited to, pharmaceuticals, agrochemicals, and various other chiral compounds. Indeed, while generally only one enantiomer is biologically active for the intended purpose of the drug, the other enantiomer can be toxic. To achieve enantiomeric purity using current methods of traditional chemical synthesis, a reaction must either be fed a chiral feedstock or comprise an additional separation step, either of which can be time consuming and/or very costly. Therefore, there is a need for more efficient ways of producing stereomerically pure compounds.

SUMMARY OF THE INVENTION

The present invention relates to compositions and methods utilizing thermostable and novel alcohol dehydrogenase enzymes for biosynthesizing chiral specific molecules for use as precursor molecules in synthesizing pharmaceutical compounds. Particularly, in preferred embodiments, the invention relates to directed engineering of an enzymatic catalytic site of an alcohol dehydrogenase enzyme gene, for enhancing catalytic efficiency, and for enhancing enantioselectivity, for (S)-enantiomer substrate catalytic activity, and for providing aryl (S)-enantiomer products in stereomeric excess.

In some embodiments, the invention relates to a method of making a composition comprising (2S)-4-phenylbutan-2-ol in stereomeric excess comprising: a) providing: i) 4-phenylbutan-2-one, ii) a composition comprising the amino acid sequence having SEQ ID NO:01, and iii) a reducing agent; b) mixing said 4-phenylbutan-2-one, said composition, and said reducing agent under conditions such that (2S)-4-phenylbutan-2-ol is formed in stereomeric excess. In further embodiments, said reducing agent is NADPH. In one embodiment, the method further comprises a xerogel. In one embodiment, the amino acid sequence is encapsulated. In a further embodiment, the amino acid sequence further comprises a xerogel.

In some embodiments, the invention relates to a method of making a composition comprising (2S)-1-phenylpropan-2-ol in stereomeric excess comprising: a) providing: i) 1-phenylacetone, ii) a composition comprising the amino acid sequence having SEQ ID NO:01, and iii) a reducing agent; b) mixing said 1-phenylacetone, said composition, and said reducing agent under conditions such that (2S)-1-phenylpropan-2-ol is formed in stereomeric excess. In further embodiments, said reducing agent is NADPH. In one embodiment, the method further comprises a xerogel. In one embodiment, the amino acid sequence is encapsulated. In a further embodiment, the amino acid sequence further comprises a xerogel. In some embodiments, the invention relates to a method of making composition with stereomeric excess comprising: a) providing: i) a first compound having the following formula,

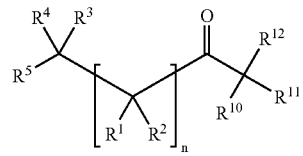

wherein, $R^5$ is alkyl, substituted alkyl, aryl, substituted aryl, heteroaryl, or substituted heteroaryl, $R^1$, $R^2$, $R^3$, and $R^4$, are each individually and independently hydrogen, alkyl, or halogen, $R^{10}$, $R^{11}$, and $R^{12}$ are each individually and independently hydrogen, or halogen, and n is 0, 1, 2, 3, 4, 5, 6, 7, 8, or 9; in other embodiments, $R^5$ is alkyl, substituted alkyl, aryl, substituted aryl, heteroaryl, or substituted heteroaryl, $R^1$, $R^2$, $R^3$, and $R^4$, are each individually and independently hydrogen, alkyl, halogen, or methoxy $R^{10}$, $R^{11}$, and $R^{12}$ are each individually and independently hydrogen, halogen, or methoxy and n is 0, 1, 2, 3, 4, 5, 6, 7, 8, or 9; ii) a composition comprising an amino acid sequence greater than 200 amino acid residues (but preferably less than 1000 amino acid residues) and at least 60% identical to SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic-acid corresponding to amino acid position 186 of SEQ ID NO:01; iii) a reducing agent; b) mixing said first compound, said amino acid sequence, and said reducing agent under conditions such that a second compound having the following formula,

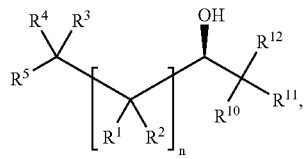

is formed in stereomeric excess. In further embodiments, said reducing agent is NADPH. In further embodiments, $R^1$ and $R^2$ are hydrogen. In further embodiments, $R^{10}$, $R^{11}$, and $R^{12}$ are hydrogen. In further embodiments, n=0, $R^3$ and $R^4$ are hydrogen and $R^5$ is aryl or substituted aryl. In further embodiments, second compound is formed in greater than 55%, 65%, 75%, 85%, 95%, and even more preferably in 99% stereomeric excess by weight. In further embodiments, said conditions include a temperature between 25° C. and 87.5° C. or 5° C., 15° C., 25° C., 35° C., 45° C., and 85° C., 87.5° C., 90° C., 92.5° C., 95° Celsius. In further embodiments, said conditions include a pH between 4.3 and 8.8 and more preferably a pH between 4.9 and 8.8. In one embodiment, the composition further comprises a xerogel. In one embodiment, the amino acid sequence is encapsulated. In a further embodiment, the amino acid sequence further comprises a xerogel.

In additional embodiments, the invention relates to a composition comprising an amino acid sequence greater than 200 amino acid residues (but preferably less than 1000 amino acid residues) and at least 60% identical (more preferably at least 80% identical, still more preferably at least 90% identical, still more preferably at least 95% identical, and most preferably at least 99% identical) to SEQ ID NO:01, wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01. In one embodiment, the composition further comprises a xerogel. In one embodiment, the amino acid sequence is encapsulated. In a further embodiment, the amino acid sequence further comprises a xerogel.

In further embodiments, the invention relates to a method of making a first compound having the following formula,

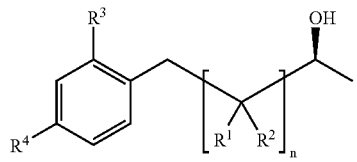

comprising: a) providing: i) a second compound having the following formula,

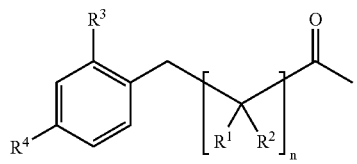

wherein, $R^1$, $R^2$, $R^3$, and $R^4$, are each individually and independently hydrogen, alkyl, or halogen and n is 0 or 1; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical or similar to SEQ ID NO:01 (more preferably at least 80% identical or similar, still more preferably at least 90%, still more preferably at least 95%, and most preferably at least 99% identical), wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, and iii) a reducing agent; b) mixing said second compound, said amino acid sequence, and said reducing agent under conditions such that said first compound is formed. In further embodiments, said reducing agent is NADPH. In one embodiment, the method further comprises a xerogel. In one embodiment, the amino acid sequence is encapsulated. In a further embodiment, the amino acid sequence further comprises a xerogel.

In some embodiments, the invention relates to a method of making composition with stereomeric excess comprising: a) providing: i) a first compound having the following formula,

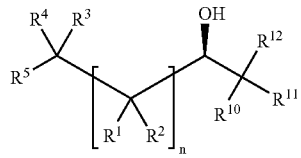

wherein, $R^5$ is alkyl, substituted alkyl, aryl, substituted aryl, heteroaryl, or substituted heteroaryl, $R^1$, $R^2$, $R^3$, and $R^4$, are each individually and independently hydrogen, alkyl, or halogen, $R^{10}$, $R^{11}$, and $R^{12}$ are each individually and independently hydrogen, or halogen, and n is 0, 1, 2, 3, 4, 5, 6, 7, 8, or 9; in other embodiments, $R^5$ is alkyl, substituted alkyl, aryl, substituted aryl, heteroaryl, or substituted heteroaryl, $R^1$, $R^2$, $R^3$, and $R^4$, are each individually and independently hydrogen, alkyl, halogen, or methoxy $R^{10}$, $R^{11}$, and $R^{12}$ are each individually and independently hydrogen, halogen, or methoxy and n is 0, 1, 2, 3, 4, 5, 6, 7, 8, or 9; ii) a composition comprising an amino acid sequence greater than 200 amino acid residues (but preferably less than 1000 amino acid residues) and at least 60% identical to SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic-acid corresponding to amino acid position 186 of SEQ ID NO:01; iii) an oxidizing agent; b) mixing said first compound, said amino acid sequence, and said reducing agent under conditions such that a second compound having the following formula,

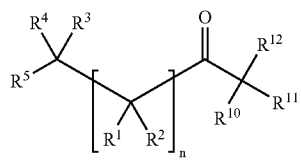

is formed in stereomeric excess. In further embodiments, said oxidizing agent is NADP$^+$. In further embodiments, $R^1$ and $R^2$ are hydrogen. In further embodiments, $R^{10}$, $R^{11}$, and $R^{12}$ are hydrogen. In further embodiments, n=0, $R^3$ and $R^4$ are hydrogen and $R^5$ is aryl or substituted aryl.

In further embodiments, said conditions include a temperature between 25° C. and 87.5° C. or 5° C., 15° C., 25° C., 35° C., 45° C., and 85° C., 87.5° C., 90° C., 92.5° C., 95° Celsius. In further embodiments, said conditions include a pH between 7.0 and 9.5 and more preferably a pH between 8.5 and 9.2 and even more preferably between 7.0 and 11.0.

In additional embodiments, the invention relates to a composition comprising an amino acid sequence greater than 200 amino acid residues (but preferably less than 1000 amino acid residues) and at least 60% identical or similar (more preferably at least 80% identical or similar, still more preferably at least 90% identical, still more preferably at least 95% identical, and most preferably at least 99% identical) to SEQ ID NO:01, wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01. In one embodiment, the invention relates to a composition comprising a gel sol formulation. In one embodiment, gel sol formulation is a xerogel. In one embodiment, the amino acid sequence is encapsulated. In a further embodiment, the amino acid sequence further comprises a xerogel.

In further embodiments, the invention relates to a method of making a first compound having the following formula,

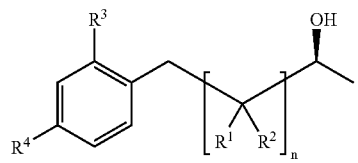

comprising: a) providing: i) a second compound having the following formula,

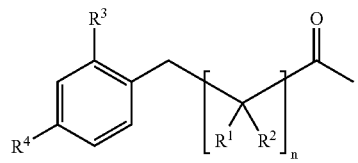

wherein, $R^1$, $R^2$, $R^3$, and $R^4$, are each individually and independently hydrogen, alkyl, or halogen and n is 0 or 1; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical or similar to SEQ ID NO:01 (more preferably at least 80% identical, still more preferably at least 90% identical, still more preferably at least 95% identical, and most preferably at least 99% identical), wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, and iii) a reducing agent; b) mixing said second compound, said amino acid sequence, and said reducing agent under conditions such that said first compound is formed. In further embodiments, said reducing agent is NADPH.

In some embodiments, the invention relates to a method of making a first compound having the following formula,

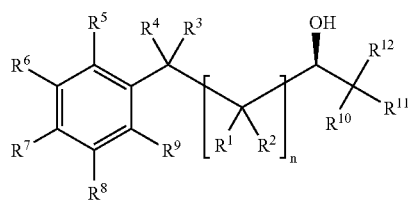

comprising: a) providing: i) a second compound having the following formula,

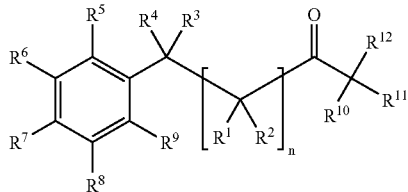

wherein, $R^1$, $R^2$, $R^3$, $R^4$, $R^5$, $R^6$, $R^7$, $R^8$, and $R^9$ are each individually and independently hydrogen, alkyl, or halogen, $R^{10}$, $R^{11}$, and $R^{12}$ are each individually and independently hydrogen, or halogen, and n is 0 or 1; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical to SEQ ID NO:01 (more preferably at least 80% identical, still more preferably at least 90% identical, still more preferably at least 95% identical, and most preferably at least 99% identical), wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, and iii) a reducing agent; b) mixing said second compound, said amino acid sequence, and said reducing agent under conditions such that said first compound is formed.

In some embodiments, the invention relates to a method of making a first compound having the following formula,

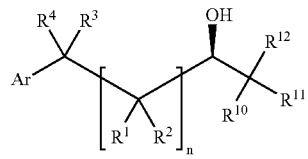

comprising: a) providing: i) a second compound having the following formula,

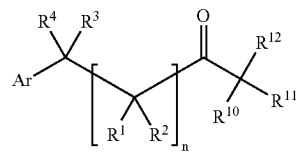

wherein, Ar is aryl, substituted aryl, heteroaryl, or substituted heteroaryl, $R^1$, $R^2$, $R^3$, and $R^4$, are each individually and independently hydrogen, alkyl, or halogen, $R^{10}$, $R^{11}$, and $R^{12}$ are each individually and independently hydrogen, or halogen, and n is 0, 1, 2, 3, 4, 5, 6, 7, 8, or 9; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical to SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, iii) a reducing agent; b) mixing said second compound, said amino acid sequence, and said reducing agent under conditions such that said first compound is formed in stereomeric excess.

In additional embodiments, the invention relates to a method of making composition with stereomeric excess comprising: a) providing: i) a first compound having the following formula,

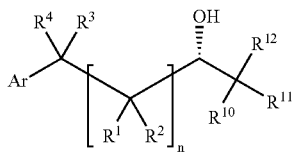

wherein, Ar is aryl, substituted aryl, heteroaryl, or substituted heteroaryl, $R^1$, $R^2$, $R^3$, and $R^4$, are each individually and independently hydrogen, alkyl, or halogen, $R^{10}$, $R^{11}$, and $R^{12}$ are each individually and independently hydrogen, or halogen, and at least one of $R^{10}$, $R^{11}$, or $R^{12}$ is a methoxy group, and n is 0, 1, 2, 3, 4, 5, 6, 7, 8, or 9; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical to SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01; iii) a reducing agent; b) mixing said first compound, said amino acid sequence, and said reducing agent under conditions such that a second compound having the following formula,

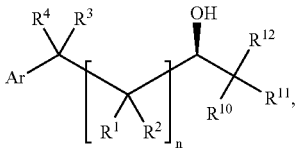

is formed in stereomeric excess.

In some embodiments, the invention relates to a method of making composition with stereomeric excess comprising: a) providing: i) a first compound having the following formula,

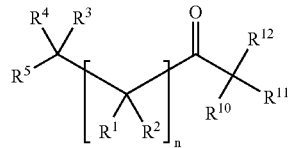

wherein, $R^5$ is alkyl, substituted alkyl, aryl, substituted aryl, heteroaryl, or substituted heteroaryl, $R^1$, $R^2$, $R^3$, and $R^4$, are each individually and independently hydrogen, alkyl, or halogen, $R^{10}$, $R^{11}$, and $R^{12}$ are each individually and independently hydrogen, or halogen, and n is 0, 1, 2, 3, 4, 5, 6, 7, 8, or 9; ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical or SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, and iii) a reducing agent; b) mixing said first compound, said amino acid sequence, and said reducing agent under conditions such that a second compound having the following formula,

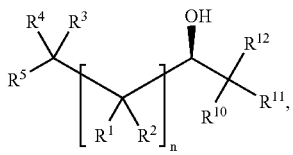

is formed in stereomeric excess.

In some embodiments, the invention relates to a method of making a composition with stereomeric excess comprising: a) providing: i) a first compound comprising an aryl and a methyl ketone, ii) a composition comprising an amino acid sequence greater than 50, 100, 150, 200, or 250 amino acid residues (but preferably less than 1000 amino acid residues) and at least 35%, 40%, 50%, 60%, 70%, 80%, or 90% identical to SEQ ID NO:01 (more preferably at least 80% identical, still more preferably at least 90% identical, still more preferably at least 95% identical, and most preferably at least 99% identical) wherein said amino acid sequence comprises either, 1) an alanine corresponding to amino acid position 110 of SEQ ID NO:01, or 2) an alanine corresponding to amino acid position 110 of SEQ ID NO:01 and an aspartic acid corresponding to amino acid position 186 of SEQ ID NO:01, and iii) a reducing agent; b) mixing said first compound, said amino acid sequence, and reducing agent under conditions such that a second compound comprising an aryl and an alpha methyl secondary alcohol is formed in stereomeric excess.

In some embodiments, the invention relates to a method of making a composition with stereomeric excess comprising: a) providing: i) a first compound comprising an aromatic moiety and a methyl ketone moiety, ii) a composition comprising an amino acid sequence variant of *Thermoanaerobacter ethanolicus* secondary alcohol dehydrogenase (TeSADH) and iii) a reducing agent; b) mixing said first compound, said amino acid sequence, and reducing agent under conditions such that a second compound comprising an aromatic moiety and a methyl secondary alcohol is formed in stereomeric excess.

In some embodiments, the invention relates to a method of making a composition with stereomeric excess comprising: a) providing: i) a first compound comprising 1) chemical group selected from the group consisting of arylalkyl, substituted arylalkyl, a heteroarylalkyl, and 2) a methyl ketone, ii) a microorganism that expresses a composition comprising an amino acid sequence variant of TeSADH and iii) a reducing agent; b) mixing said first compound, said microorganism, and reducing agent under conditions such that a second compound comprising an aromatic moiety and an methyl secondary alcohol is formed in stereomeric excess.

In some embodiments, the invention relates to an isolated nucleic acid sequence, selected from the group consisting of SEQ ID NO:02 and SEQ ID NO:04. In further embodiments, the invention relates to a composition comprising a nucleic acid sequence selected from the group consisting of SEQ ID NO:02 and SEQ ID NO:04.

In additional embodiments, the invention relates to an isolated polypeptide sequence, selected from the group consisting of SEQ ID NO:01 and SEQ ID NO:03. In further embodiments, the invention relates to a composition comprising a polypeptide sequence selected from the group consisting of SEQ ID NO:01 and SEQ ID NO:03.

In some embodiments, the invention relates to an isolated nucleic acid sequence that encodes the polypeptide sequences disclosed herein. In further embodiments, the invention relates to an isolated nucleic acid sequence that is complimentary to a single stranded nucleic acid sequence that encodes amino acid sequences disclosed herein.

In additional, embodiments, the invention relates to a microorganism that expresses amino acid sequences disclosed herein. In further embodiments, the invention relates to microorganisms that have nucleic acid sequences corresponding to the expression of amino acid sequences disclosed herein.

In further embodiments, the invention relates to a nucleic acid sequence coding for a polypeptide at least 35% identical to SEQ ID NO:01 (more preferably at least 80% identical, still more preferably at least 90% identical, still more preferably at least 95% identical, and most preferably at least 99% identical). It is preferred that the polypeptide exhibits at least 50% (more preferably at least 80%, still more preferably at least 90%, and most preferably at least 100%) of the activity of the polypeptide having the exact sequence of SEQ ID NO:01. In one embodiment, said nucleic acid sequence encodes a protein comprising an alanine at amino acid position 110. In further embodiments, said nucleic acid sequence encodes a protein further comprising an aspartic acid at amino acid position 186.

In some embodiments, the invention relates to a composition for providing (S)-stereospecific and stereoselective substrate catalytic activity, comprising a nucleic acid sequence coding for a polypeptide at least 35% identical to SEQ ID NO:01 (more preferably at least 80% identical, still more preferably at least 90% identical, still more preferably at least 95% identical, and most preferably at least 99% identical), wherein said nucleic acid sequence encodes a protein comprising an alanine at amino acid position 110 for providing aryl substrate catalytic activity. In further embodiments, said nucleic acid sequence encodes a protein further comprising an aspartic acid at amino acid position 186.

In one embodiment, the present invention contemplates a composition comprising an amino acid sequence greater than 200 amino acid residues and at least 90% identical to SEQ ID NO:01, wherein said composition exhibits at least 50% (more preferably at least 80%, still more preferably at least 90%, and most preferably at least 100%) of the activity of the polypeptide having the exact sequence of SEQ ID NO:01.

In one embodiment, the present invention contemplates a fusion protein, said fusion protein comprising a first amino acid sequence at least 90% (preferably at least 95%, a more preferably at least 99%) identical to SEQ ID NO:01, and a second amino acid sequence, wherein said second amino acid sequence comprises an affinity tag (e.g. a FLAG tag, a HIS tag, a polypeptide comprising an active site, such as an enzyme, etc.). It is preferred that the fusion protein exhibits enzyme activity that is at least 50% (more preferably at least 80%, still more preferably at least 90%, and most preferably at least 100%) of the activity of SEQ ID NO:01.

In additional embodiments, the invention relates to a method of making hydroxylalkylaryl (S)-enantiomer products, comprising, a) providing, i) a microorganism expressing an amino acid sequence at least 35% identical to SEQ ID NO:01 (more preferably at least 80% identical, still more preferably at least 90% identical, still more preferably at least 95% identical, and most preferably at least 99% identical), providing aryl (S) stereoselective substrate catalytic activity; and b) a mixture of aryl substrates, wherein said substrate is selected from the group comprising an aryl ketone; ii) contacting said microorganism with said aryl substrate, iii) incubating said contacted microorganism and aryl substrate under such conditions for providing aryl (S)-enantiomer products. In further embodiments, said nucleic acid sequence encodes a protein further comprising an aspartic acid at amino acid position 186. In further embodiments, said aryl substrate is selected from the group comprising benzylacetone, 1-phenyl-2-butanone, and 1-phenyl-2-propanone. In further embodiments, said aryl (S)-alcohol product is selected from the group comprising 4-phenyl-2-butanol, 1-phenyl-2-butanol, 1-phenyl-2-propanol, and 1-phenyl ethyl alcohol. In further embodiments, said aryl (S)-enantiomer product is in enantiomeric excess. In further embodiments, said aryl (S)-enantiomer product in enantiomeric excess is (S)-4-phenyl-2-butanol.

In one embodiment, the present invention contemplates a method for introducing a mutation in a wild-type *T. ethanolicus* adhB gene in the pADHB1M1-kan plasmid during amplification (e.g. PCR). For example, primers can be designed so as to create a mutation in the 5' end of the gene and the 3' end of the gene. In one embodiment, a primer encoding an alanine at position 110 of TeSADH is employed. In one embodiment, said primer has the nucleic acid sequence set forth in SEQ ID NO:15 or in SEQ ID NO:17.

In one embodiment, the present invention contemplates the expression of mutated TeSADH. In one embodiment, the mutated TeSADH is expressed as a fusion protein. In one embodiment, the mutated TeSADH contains an affinity tag permitting rapid isolation and/or purification. For example, in one embodiment, mutant TeSADHs are contemplated that are expressed in *E. coli* as fusion proteins with a C-terminal His6 tag. In a further embodiment, a mutant TeSADH is contemplated to comprise a fusion partner, including but not limited to enzymes of the oxidative pentose phosphate pathway, non-oxidative pentose phosphate pathway, etc.

The present invention contemplates using the polynucleotides of the present invention for expression of the polypeptides in vitro and in vivo. Therefore, the present invention contemplates polynucleotide sequences encoding the sequence of SEQ ID NO:01 or variants thereof, wherein said polynucleotide sequence is contained on a recombinant expression vector (e.g. operably linked to a promoter). It is also contemplated that such vectors will be introduced into a variety of host cells, both eukaryotic and prokaryotic (e.g., bacteria such as *Escherichia coli*).

DESCRIPTION OF THE FIGURES

FIG. 9 shows exemplary amino acid and nucleic acid sequences of *Thermoanaerobacter ethanolicus* secondary-alcohol dehydrogenase (TeSADH) W110A variant 1 (SEQ ID NOs:01 and 03, respectively); TeSADH W110A variant 2 (SEQ ID NOs:02 and 04, respectively); TeSADH mutant Y267G (SEQ ID NOs:05 and 06, respectively); wild type TeSADH (SEQ ID NOs: 07 and 08); demonstration of numbering amino acid positions in sequence for TeSADH (SEQ ID NO:09); *Thermoanaerobacter brockii* ADH CAA46053 (SEQ ID NOs:10 and 11); *Equus caballus* (horse) ADH (E.C.1.1.1.1) (SEQ ID NOs:12 and 13); and PCR primers (SEQ ID NOs: 14-19). Please note that the original (wild-type) TeSADH sequence starts with two methionines (MM). In contrast, as disclosed herein, TeSADH and TeSADH W110A sequences are provided that encode a single N-terminal methionine (one M) as the first amino acid residue in the sequence.

DEFINITIONS

Figure 1:
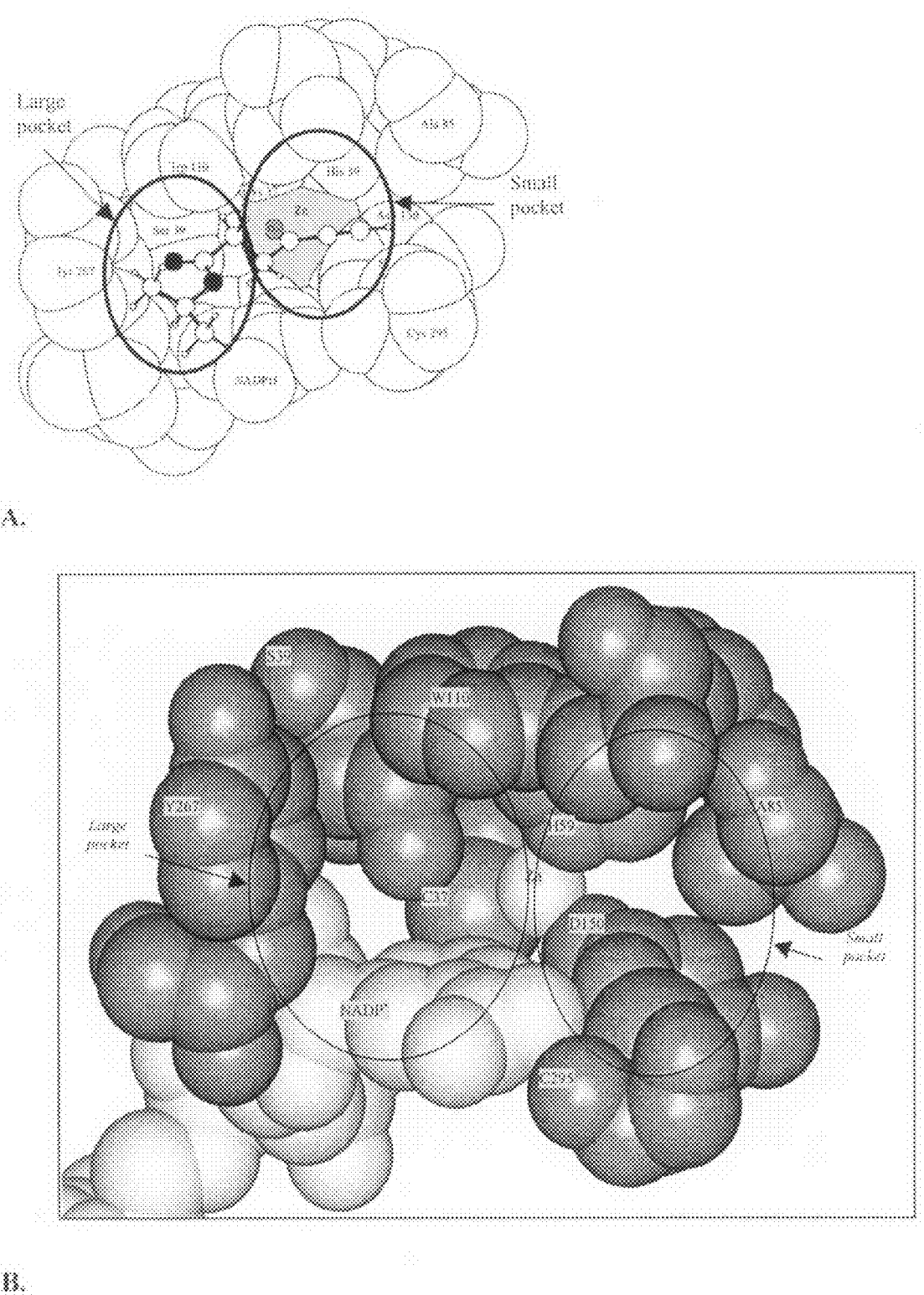
FIG. 1 shows an exemplary model of a *Thermoanaerobacter brockii* SADH ((TbSADH, identical to TeSADH) active site in CPK representation, based on PDB # 1YKF. NADP$^+$ and Zn are in white, TbSADH residues are in gray. NADP$^+$'s nicotinamide ring was rotated 90° to match the orientation of NAD⁺'s nicotinamide ring in the HLADH•BRB•NAD⁺ ternary complex (PDB # 1 HLD).

To facilitate an understanding of the present invention, a number of terms and phrases as used herein are defined below:

The use of the article "a" or "an" is intended to include one or more.

As used herein, terms defined in the singular are intended to include those terms defined in the plural and vice versa.

The chemical terms provided in this application have a variety of synonyms and thus the chemical terms listed in this application are not meant to be limiting descriptions.

The term "alkyl" refers to a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The term "aryl" refers to an aromatic carbocyclic moiety such as phenyl or naphthyl.

The term "heteroaryl" refers to an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The term "heteroarylalkyl" refers to an alkyl having at least one alkyl hydrogen atom replaced with a heteroaryl moiety, such as —$CH_2$pyridinyl, —$CH_2$pyrimidinyl, and the like.

The term "heterocycle" (also referred to herein as a "heterocyclic ring") refers to a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocyclealkyl" refers to an alkyl having at least one alkyl hydrogen atom replaced with a heterocycle, such as —$CH_2$-morpholinyl, and the like.

The term ""methyl secondary alcohol" refers to a hydroxyl-substituted alkyl having a methyl group bound to a carbon with a hydroxyl group, such as —$CHOHCH_3$.

The term "substituted", as used herein, refers to at least one hydrogen atom of a molecular arrangement is replaced with a substituent. With regard to amino acid sequences, a substituted amino acid is intended to include sequences in which an amino acid residue is replaced, deleted, added, or where any of the preceding optionally contains one or more additional substituent(s). In the case of an oxo substituent ("═O"), two hydrogen atoms are replaced. When substituted, one or more of the groups below are "substituents." Substituents within the context of this invention include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as, —$NR_aR_b$, —$NR_aC(═O)R_b$, —$NR_aC(═O)NR_aNR_b$, —$NR_aC(═O)OR_b$—$NR_aSO_2R_b$, —$C(═O)R_a$, $C(═O)OR_a$, —$C(═O)NR_aR_b$, —$OC(═O)NR_aR_b$, —$OR_a$, —$SR_a$, —$SOR_a$, —$S(═O)_2R_a$, —$OS(═O)_2R_a$ and —$S(═O)_2OR_a$. In addition, the above substituents may be further substituted with one or more of the above substituents, such that the substituent comprises a substituted alkyl, substituted aryl, substituted arylalkyl, substituted heterocycle, or substituted heterocyclealkyl. $R_a$ and $R_b$ in this context may be the same or different and, independently, hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

The term "unsubstituted", as used herein, refers to any compound that does not contain extra substituents attached to the compound. An unsubstituted compound refers to the chemical makeup of the compound without extra substituents, e.g., the compound does not contain protecting group(s). For example, unsubstituted proline is a proline amino acid even though the amino group of proline may be considered disubstituted with alkyl groups.

The terms "bacteria" and "bacterium" refer to all prokaryotic organisms, including those within all of the phyla in the Kingdom Procaryotae. It is intended that the terms encompass all microorganisms considered to be bacteria, for example, *Pseudomonas* sp. including *Mycoplasma*, *Chlamydia*, *Actinomyces*, *Streptomyces*, and *Rickettsia*. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process, which is well known in the art. (See e.g., Finegold and Martin, Diagnostic Microbiology, 6th Ed., CV Mosby St. Louis, pp. 13-15 [1982]). "Gram positive bacteria" are bacteria, which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "microorganism" refers to any species or type of microorganism, including but not limited to, bacteria, archaea, fungi, protozoans, mycoplasma, and parasitic organisms.

The terms "thermophile" and "hyperthermophile" refer to an organism isolated from high or extreme temperature environments (e.g. greater than 50° C., typically greater than 70 C, and more typically greater than 80 C, and most typically greater than 90° C., and as high as 97-101° C.), such as a *Thermoanaerobacter ethanolicus*, a bacterium isolated from a hot spring (Yellowstone National Park, Wyo., U.S.).

As used herein, the terms "contacting" and "contacted," refer to bringing one or more of the compositions of the present invention into contact with a substrate or a sample comprising potential substrates for reacting with the catalytic sites of enzymes of the present invention. Compositions of the present invention may react with the contacted substrates for providing reacted products. The present invention contemplates that the disclosed compositions are contacted with the substrates or samples comprising potential substrates in sufficient volumes and/or concentrations to react with the catalytic site.

As used herein, the term "enhanced" in reference to a chiral specific product, refers to an increase in the stereomeric excess of specific products following a chemical reaction of the present invention, for example, increasing the percent e.e. of a product over that obtained by previously published compositions and methods or increasing the percent e.e. of a product over that obtained by nonmutated enzymes.

As used herein, the term "incubating" in reference to a contacted enzyme and substrate, refers to maintaining a chemical or biochemical system under specific conditions, such a temperature and/or pressure and/or substrate or product concentration, in order to promote a particular reaction product.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The terms "allele" and "alleles" refer to each version of a gene for a same locus that has more than one sequence. For example, there are multiple alleles for eye color at the same locus.

The term "nucleic acid sequence," "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, disease resistance genes, growth factors, etc.), and non-coding regulatory sequences which do not encode an mRNA (e.g., promoter sequence, polyadenylation sequence, termination sequence, enhancer sequence, etc.).

The term "oligonucleotide" refers to a molecule comprised of two or more deoxyribonucleotides or ribonucleotides, preferably more than three, and usually more than ten. The exact size will depend on many factors, which in turn depend on the ultimate function or use of the oligonucleotide. The oligonucleotide may be generated in any manner, including chemical synthesis, DNA replication, reverse transcription, or a combination thereof.

The term "polynucleotide" refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA, or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

The terms "complementary" and "complementarity" refer to polynucleotides (i.e., a sequence of nucleotides) related by the base-pairing rules. For example, the sequence "A-G-T-" is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "protein," "polypeptide," "peptide," "encoded product," and "amino acid sequence" are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences that are derived from the deduced amino acid sequence and modified by post-translational processing, where modifications include, but not limited to, the addition of metal ions, glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence.

Some embodiments of the present invention provide mutant or variant forms of enzymes described herein. It is possible to modify the structure of a peptide having an activity of the enzymes described herein for such purposes as enhancing substrate specificity, stability, and the like. For example, a modified peptide can be produced in which the amino acid sequence has been altered, such as by amino acid substitution, deletion, or addition. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of enzymes described herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), *Biochemistry*, 2nd ed, WH Freeman and Co. [1981]). Whether a change in the amino acid sequence of a peptide results in a functional homolog can be readily determined by assessing the ability of the variant peptide to produce a response in a fashion similar to the wild-type protein using the assays described herein. Peptides in which more than one replacement has taken place can readily be tested in the same manner.

As used herein, the term "fusion protein" refers to a chimeric protein containing the protein of interest (i.e., a mutant enzyme or fragments thereof) joined to an exogenous protein fragment, such as a non-enzyme sequence, an enzyme sequence, etc. The fusion partner may provide a detectable moiety, may provide an affinity tag to allow purification of the recombinant fusion protein from the host cell, may provide an additionally enzymatic activity, and the like. If desired, the fusion partner may be removed from the protein of interest by a variety of enzymatic or chemical means known to the art.

The term "isolated" when used in relation to a nucleic acid or polypeptide, as in "an isolated oligonucleotide," refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded).

The term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the terms "purified" and "to purify" also refer to the removal of contaminants from a sample. The removal of contaminating proteins results in an increase in the percent of polypeptide of interest in the sample. In another example, recombinant polypeptides are expressed in bacteria, yeast, or mammalian host cells and the polypeptides are purified by the removal of host cell proteins; the percent of recombinant polypeptides is thereby increased in the sample.

The terms "in operable combination", "in operable order," and "operably linked" as used herein refer to the linkage of nucleic acid sequences in such a manner that a nucleic acid molecule capable of directing the transcription of a given gene and/or the synthesis of a desired protein molecule is produced.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" or "variant" when made in reference to a gene, respectively, to a gene or to a gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, "engineer," "site-directed mutagenesis," and "directed evolution" refer to a variety of methods for mutating, adding, deleting, or chemically modifying at least one nucleic acid of a sequence that results in substituting at least one amino acid in the expressed protein.

As used herein, "substrate" as in a biocatalytic reaction refers to a chemical entity whose conversion to a "product" or "products" is catalyzed by one or several enzymes.

As used herein, "nicotinamide adenine dinucleotide" or "NAD" or "NADH" refers in general to a ubiquitous redox cofactor that functions as a carrier of electron pairs for redox reactions. The oxidized form of the cofactor actually carries a positive charge, and is denoted NAD$^+$ while the reduced form is NADH.

The term "NAD" refers to a molecule with a chemical formula $C_{21}H_{27}N_7O_{14}P_2$, a structure

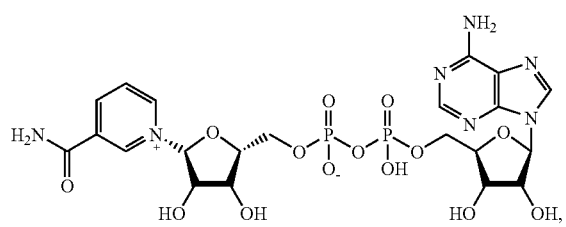

and further described as any one of synonyms including nicotinamide adenine dinucleotide; adenine-nicotinamide dinucleotide Coenzyme I; and the like.

The term "NADP" refers to refers to a molecule with a chemical formula C21-H28-N-7-O17-P3, a structure

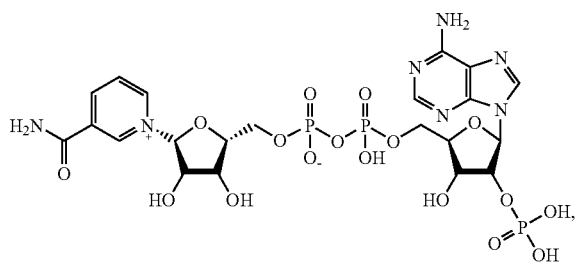

and further described as any one of synonyms including Nicotinamide adenine dinucleotide phosphate reductase; Coenzyme II; and the like.

The term "NADH" refers to a molecule with a chemical formula C21-H29-N-7-O14-P2, a structure

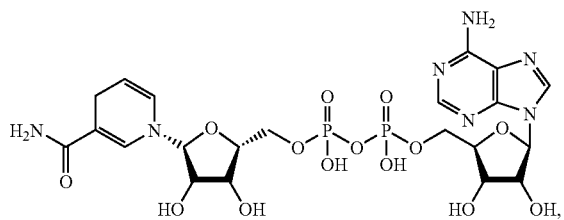

and further described as any one of synonyms including Dihydronicotinamide-adenine dinucleotide; Coenzyme I, reduced; and the like.

The term "NADPH" refers to a molecule with a chemical formula C21-H30-N-7-O17-P3, a structure

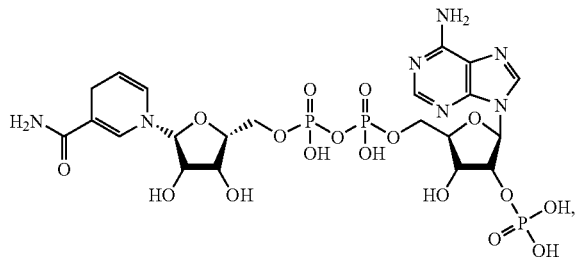

and further described as any one of synonyms including Nicotinamide adenine dinucleotide phosphate; and the like.

As used herein, a "reducing agent" refers to any of a variety of reagents that are utilized as a hydrogen donating source in the reduction of ketones to alcohols. In preferred embodiments, proteins disclosed herein catalyzed the reduction of ketones to alcohols using NADPH as a hydrogen donating source; thus, NADPH is a reducing agent. It is understood that the reducing agent may be generated in situ under the conditions of a particular chemical reaction. For example, in a preferred embodiment of the invention, the reaction mixture contains isopropanol that is used both as a cosolvent and as a substrate to recycle the cofactor. The reaction starts with isopropanol being oxidized to 2-propanone, and the reducing agent NADPH being produced to then be used for benzylacetone reduction. The reaction goes back and forth until most benzylacetone has been reduced to 4-phenyl-2-butanol. Other examples of reducing agents include, but are not limited to NADH, FADH, $FADH_2$, sodium borohydride, lithium aluminum hydride and the like.

As used herein, an oxidizing agent refers to any of a variety of reagents that are utilized as a hydrogen abstraction source in the oxidation of alcohols to ketones. In preferred embodiments, proteins disclosed herein catalyzed the oxidation of alcohols to ketones using $NADP^+$ as a hydrogen abstraction source from the alcohol in oxidation to the ketone; thus, $NADP^+$ is an oxidizing agent. It is understood that the reducing agent may be generated in situ under the conditions of a particular chemical reaction. Other examples of reducing agents include, but are not limited to $NAD^+$, FADH, $FAD^+$, potassium chromate, potassium permanganate, and the like.

As used herein, "mutant," "mutation," "mutating," and "mutagenesis" refer to any alteration in a gene from its "natural," "nonmutated," or "wild-type" state.

The term "wild-type" when made in reference to a peptide sequence and nucleotide sequence refers to a peptide sequence and nucleotide sequence, respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. In contrast, the term "modified" or "mutant" refers to a peptide sequence and nucleotide sequence which displays modifications in sequence and/or functional properties (i.e., altered characteristics, such as functionally altered and/or functionally inactive) when compared to the wild-type peptide sequence and nucleotide sequence, respectively. It is noted that naturally-occurring mutants can be isolated; these are identified by the fact that they have altered characteristics when compared to the wild-type peptide sequence and nucleotide sequence. Nucleic acid sequences and/or proteins may be modified by chemical, biochemical, and/or molecular biological techniques. Modifications to nucleic acid sequences include introduction of one or more deletion, insertion, and substitution. A "deletion" is defined as a change in a nucleic acid sequence in which one or more nucleotides is absent. An "insertion" or "addition" is that change in a nucleic acid sequence, which has resulted in the addition of one or more nucleotides. A "substitution" results from the replacement of one or more nucleotides by a molecule which is a different molecule from the replaced one or more nucleotides.

The terms "position 110" and "position 186" refer to amino acid positions as demonstrated in SEQ ID NO:01 and 09, corresponding to certain positions in homologous genes. When referring to an amino acid, such as alanine, corresponding to amino acid position, such as position 110, it is understood to include alignment shifts in which the amino acid sequence is not corresponding directly to the $110^{th}$ amino acid. For example, SEQ ID NO:01 may be altered such that the first five amino acids are deleted without loss of protein activity. In such a case, position 110 corresponds to the $105^{th}$ amino acid.

As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to biological activity. As used herein, the term "stereoisomer" refers to compounds that have their atoms connected in the same order but differ in the arrangement of their atoms in space. (e.g. L-alanine and D-alanine).

As used herein, the terms "substantially purified enantiomer" and "substantially purified enantiomer preparation" refer to a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

As used herein, the phrase "enantiomeric excess" or "e.e." refers to a reaction product wherein one enantiomer is produced in excess of the other and the percentage of the excess enantiomer is calculated using either (or both) of the following algorithms:

enantiomeric excess=(specific rotation of the reaction product/specific rotation of the pure enantiomer in excess)*100.      Algorithm No. 1 enantiomeric excess=(moles of major enantiomer-moles of other enantiomer/total moles of both enantiomers)*100.      Algorithm No. 2

As an example (the values in this example are offered for illustration only and do not represent data subsequently expressed in the "Experimental" section of this application), the observed rotation of a reaction product +8.52 degrees of rotation and the specific rotation of the R-configured enantiomer is reported as +15.00 degrees of rotation. The sign of the specific rotation of the reaction product indicates which enantiomer is in excess (e.g. in this example the R-configured isomer is in excess). If these values are inserted into Algorithm No. 1, the enantiomeric excess=(+8.52/+15.00) (100) =56.8% in excess of the R-isomer.

Whether expressed as a "purified enantiomer" or "a compound in enantiomeric excess", the terms refer to the amount of one enantiomer exceeds the amount of the other. Thus, when referring to an enantiomer preparation, both (or either) of the percent of the major enantiomer (e.g. by weight) and (or) the percent enantiomeric excess of the major enantiomer may be used to determine whether the preparation represents a purified enantiomer preparation.

As used herein, the term "optical purity" refers to the ratio of the observed optical rotation of a sample consisting of a mixture of enantiomers to the optical rotation of one pure enantiomer.

The term "stereomeric excess" refers to chiral chemical reactions wherein chiral product(s), such as enantiomers or diastereomers, are obtained in excess of the other stereoisomers. A stereoselective reaction may also be referred to as "asymmetric synthesis".

As used herein, a "catalyst" refers to a substance that, when added to a reaction mixture, changes (e.g. speeds up) the rate of attainment of equilibrium in the system without itself undergoing a permanent chemical change. Examples of suitable catalysts contemplated for use in the present invention include, but are not limited to, tetrabromomethane ($CBr_4$), carbon tetraiodide, and iodide.

The term "encapsulation" in general refers to any method of immobilizing a compound, such as an enzyme, onto a surface, or inside a case, such as a capsule, such that the compound retains its activity.

The term "hydrogel" refers to a wet sol gel in contrast to "xerogel" that refers to a dried form of "hydrogel."

DESCRIPTION OF THE INVENTION

The present invention relates to compositions and methods utilizing thermostable and novel alcohol dehydrogenase enzymes for biosynthesizing chiral specific molecules for use as precursor molecules in synthesizing pharmaceutical compounds. Particularly, in preferred embodiments, the invention relates to directed engineering of an enzymatic catalytic site of an alcohol dehydrogenase enzyme gene for catalytic efficiency and enhancing enantioselectivity for (S)-enantiomer substrate catalytic activity for providing aryl (S)-enantiomer products in stereomeric excess.

Commercially available enzymatic catalysts typically have several shortcomings that prevent their use in industrial applications. They lack long-term stability; they lack activity in organic solvents and at elevated temperatures; and their substrate specificity is often too narrow. They are often not capable of providing commercially desirable chiral products with an enantiomeric purity necessary for industrial applications. Therefore there is a need for industrial biocatalysts, such as purified enzyme systems, to create a chiral feedstock or to create an enantiomerically pure end product, in particular for chiral aromatic alcohols for providing enantiomeric purity through quicker and less costly methods. Chiral aromatic alcohols can be important building blocks in a variety of high-value chemicals including, but not limited to, pharmaceuticals, agrochemicals, and various other chiral compounds. Alcohol dehydrogenases (ADHs) (EC 1.1.1.1 and 1.1.2) catalyze the reversible reduction of ketones and aldehydes to alcohols (Burdette, et al., (1996) Biochem. J. 316: 115-122). Commercially available ADHs have several shortcomings that prevent their use in industrial applications. ADHs lack long-term stability, lack activity in organic solvents and at elevated temperatures, and their substrate specificity is often too narrow (Hummel, et al., (1997) Adv. Biochem. Engin./Biotechnol. 58:145-184); herein incorporated by reference.

Naturally occurring (wild-type/nonmutated) ADH from various *Thermoanaerobacter* (T) species have been described in several publications and patents for use in stereoselective production of secondary alcohols. *T. ethanolicus*, *T. tengcongensis*, and *T. brockii* ADH-T are described for use as (S)-alcohol dehydrogenases and as overexpressed recombinant products in *E. coli*, (E.C. number: 1.1.1.2) (Intl. Publication No. WO2005121326; herein incorporated by reference; *Thermoanaerobacter* (T) species in Product List for Order-No: 26.10; Julich Chiral Solutions, Prof.-Rehm-Straβe 1, D-52428 Jülich, Germany; *T. brockii* in U.S. Patent Appln. No. 20050191735; all of which are herein incorporated by reference). However, although these publications describe ADH from thermophilic organisms, none of these publications disclose sequence mutations of the present inventions or demonstrate the use of a mutant ADH from a thermophilic organism, in particular a *T. ethanolicus*, with catalytic activity for aryl secondary alcohols and ketones, such as phenylacetone (1-phenyl-2-propanone) and benzylacetone (4-phenyl-2-butanone), for providing (S) aryl alcohols in enantiomeric excess. In particular, wild-type SADH, such as TeSADH, show little enzymatic activity upon benzylacetone or phenyl acetone substrates, such that no (S) products are formed. In contrast, W110A mutants of the present inventions are highly active on benzylacetone and phenyl acetone, and further demonstrate high (S) enantioselectivity yielding (S) products. Further, the inventors developed an enzyme catalyst that was able to produce 1-phenyl-2-propanol and 4-phenyl-2-butanol with good efficiency. Several attempts were previously made to engineer stereospecific catalytic activity in ADH and other hydroxylases from nonthermophilic organisms. For example, a YPR1 gene encoding the alcohol dehydrogenase from bakers' yeast (*Saccharomyces cerevisiae*) was engineered for producing S-1-phenylethanol by the reduction of acetophenone, such as for using in U.S. Patent Appln. No. 20020061564 and Nakamura et al., (1997) Bioscience, Biotechnology and Biochemistry, 61:375-377; all of which are herein incorporated by reference.

Further, attempts for providing stereospecific ADH activity in the oxidation of secondary alcohols or the reduction of ketones, including substrates with aryl including phenyl groups, have been described using enzymes from nonthermophile organisms. For example, *Rhodococcus ruber* ADH is described as a catalysis for the reduction of ketones, particularly of acetophenone, and for oxidizing alcohols, particularly of 1-phenylethanol with preferred co-substrates for the reduction as secondary alcohols, such as isopropanol, 4-methyl-2-pentanol or other C,C-di-(lower alkyl)-methanols, including 4-phenyl-2-butanol, cyclopentanol, 1-(2-naphthyl) ethanol, and 1-phenyl-1-ethanol in U.S. Patent Appln. No. 20040157305; Stampfer et al., 2003, Biotechnol Bioeng 81: 865-869, published Online: 16 Jan. 2003; all of which are herein incorporated by reference, *Lactobacilli* sp., *Lactobacillus kefir* or *Lactobacillus brevis*, are described including a recombinant *Lactobacillus reuteri* oxidoreductase demonstrating some reactivity to 1-phenyl-2-propanone and low if any reactivity to acetophenone, in U.S. Patent Appln. No. 20050191735; all of which are herein incorporated by reference in their entirety.

In contrast to available ADHs from nonthermophilic organisms, a secondary ADH(SADH) from the thermophilic bacterium, *Thermoanaerobacter ethanolicus* 39E, (TeSADH) is optimally active near 90° C., thermostable (half-life of 1.7 hours at 90° C.), and specific for secondary alcohols (Burdette and Zeikus, 1994, Biochem. J. 302:163-170; herein incorporated by reference). TeSADH is also stable in solvents as shown by the retention of 90%, 100%, 80%, and 68% activity after a 3-hr incubation at 50° C. in 100% n-dodecane, n-octane, toluene, and pyridine, respectively. Thus additional benefits of providing and using enzymatic catalysis from thermophilic organisms engineered for performing highly selective reactions and that they are predicted to function under mild reaction conditions. These properties help eliminate undesirable side reactions such as isomerizations, racemizations, and rearrangements.

Several SADH genes and proteins have been described. A *T. ethanolicus* adhB gene (Te ADHB) was cloned and expressed in *Escherichia coli* (Burdette et al., 1996, Biochem. J. 316:115-122; herein incorporated by reference) as further described in U.S. Pat. No. 5,908,924; herein incorporated by reference. TeSADH is a medium chain, zinc-containing, tetrameric, ADH with 40 kDa subunits. This TeSADH is an NADP(H)-dependent enzyme that contains a single catalytic zinc coordinated by Cys37, His59, and Asp150. A thermophilic ADH is commercially available under the name *Thermoanaerobacter brockii* SADH (TbSADH) (Sigma, St. Louis, Mo.). Early sequencing results showed that TeSADH and TbSADH differ by three residues: Trp91, Pro313, and Gln325 in TeSADH versus Arg91, Arg313, and Arg325 in TbSADH. However, recent *T. ethanolicus* 39E genome sequencing results (NCBI entry ZP_00779753; SEQ ID NO:09 and 10) and repeated sequencings by the inventors revealed that wild-type TeSADH (SEQ ID NO:09) is identical to TbSADH (SEQ ID NO:012 and 13). Both enzymes have very broad substrate specificities. Examples of chiral specific reactions using wild-type TbSADH demonstrated that smaller substrates (methyl ethyl, methyl isopropyl, or methyl cyclopropyl ketones) are reduced to R alcohols, whereas the higher ketones form the S enantiomer.

TbSADH's three-dimensional structure has been solved by X-ray crystallography in complex with $NADP^+$ (PDB ID: 1YKF) and in complex with (S)-2-butanol (PDB ID: 1BXZ). TeSADH has been structurally characterized by x-ray crystallography in the Arni lab at the Universidade de Sao Paulo, Ribeirao Preto-SP, Brazil (personal communication). Since these two enzymes are identical, published TbSADH structures were used for the modeling studies of the present inventions. The TbSADH substrate-binding site is composed of a large pocket and a small pocket (FIG. 1), whose structural and chemical makeups determine the enzyme's substrate specificity and stereospecificity. The small pocket has a higher affinity for alkyl groups than the larger pocket does, and it can accommodate methyl, ethyl, isopropyl, and cyclopropyl groups, while anything larger is excluded. The current hypothesis explaining TeSADH's stereospecificity is that, if the larger of the alkyl groups of a ketone fits into the small alkyl-binding pocket, then the enzyme will likely produce an (R)-alcohol. Thus if the larger of the alkyl groups is too large to fit into the small pocket, the large group may be forced into the large alkyl-binding pocket, causing the enzyme to produce an (S)-alcohol (Keinan et al., 1986, J. Am. Chem. Soc. 108:162-169; herein incorporated by reference). This type of predicted substrate specificity mechanism was demonstrated by mutations S39T and C295A in the TeSADH active site. Mutation S39T decreased the size of the large alkyl-binding pocket. Mutation C295A enlarged the small binding pocket, allowing for longer alkyl chains to fit. Both mutations shifted TeSADH enantioselectivity toward (R)-alcohols (Heiss et al., 2001, Bioorg. and Med. Chem. 9:1659-1666; Tripp et al., 1998, J. Am. Chem. Soc. 120:5137-5141; all herein incorporated by reference). This specificity mechanism is also illustrated by the fact that TbSADH is unable to use either 4-heptanone (butyl groups on each side of the ketone) or 5-nonanone (pentyl groups on each side of the ketone), while both 2-heptaone and 2-nonaone are substrates (Keinan et al., 1986, J. Am. Chem. Soc. 108:162-169; herein incorporated by reference).

In particular, it is contemplated that changing the catalytic properties and substrate specificity of ADHs (alcohol dehydrogenases) and other enzymes from thermophilic and hyperthermophilic organisms such as *T. ethanolicus, Thermotoga neapolitana*, and *Pyrococcus furiosus* provide highly enantioselective catalysts. It is further contemplated that by designing point mutations by modeling 1-phenylethanol in the catalytic site of *T. ethanolicus* secondary alcohol dehydrogenase (TeSADH) and then using site-directed mutagenesis may result in obtaining a TeSADH derivative that is active on a secondary alcohol group based on 1-phenylethanol for using 1-phenylethanol as a new substrate (Vieille, et al., Hyperthermophilic Proteins Rock, Abstract of Talk, Michigan State University, published online; herein incorporated by reference).

As described herein, mutations of Cys-295 to Ala-295 were actually introduced by the inventors into a *T. ethanolicus* secondary alcohol dehydrogenase (TeSADH) gene (C295A TeSADH) that produced a protein demonstrating a significant shift of enantioselectivity toward the (S)-configuration in the reduction of some ethynylketones to the corresponding chiral propargyl alcohols. C295A TeSADH demonstrated a much higher activity towards t-butyl and some alpha-branched ketones than did wild-type TeSADH, however the mutant TeSADH demonstrated activity for 2-propanol comparable to wild-type TeSADH, Heiss et al., (2001) Bioorg Med. Chem. July; 9(7):1659-66; herein incorporated by reference. Site-directed mutagenesis was also used for altering a wild-type *T. ethanolicus* secondary alcohol dehydrogenase (TeSADH) gene in order to induce a Ser39 to Thr (S39T mutation) in an expressed protein for enhancing enantioselectivity for (R)-enantiomer substrates. In particular, this mutation increases catalytic activity for a 2-propanol substrate and further demonstrates changes in enantioselectivity of wild-type TeSADH that demonstrates a preference for (S)-2-pentanol whereas the S39T SADH exhibits higher enantioselectivity for the (R)-enantiomers of both 2-butanol and 2-pentanol. Further, the effect of the mutation is to decrease (S)-2-butanol specificity, and to preferentially enhance (R)-2-pentanol specificity relative to (S)-2-pentanol, Tripp et al., (1998) J. Am. Chem. Soc. 120:5137-5140; herein incorporated by reference.

Thus, naturally derived and created mutants of *T. ethanolicus* 39E secondary alcohol dehydrogenase (TeSADH) are highly thermostable, solvent-stable, and active on a broad range of substrates except for commercially important aryl molecules such as phenylacetone (1-phenyl-2-propanone), benzylacetone (4-phenyl-2-butanone), and the like. Thus TeSADH provided an excellent enzyme/sequence template for engineering an industrially level catalyst for chiral chemical synthesis of (S) aryl alcohols and ketones, using novel substrates, such as phenylacetone (1-phenyl-2-propanone), and benzylacetone (4-phenyl-2-butanone).

(S)-1-phenethyl alcohol, (S)-1-phenyl-2-propanol, and (S)-4-phenyl-2-butanol were chosen as target products because they are precursors to many major pharmaceuticals containing a secondary alcohol group. Wild-type TeSADH (SEQ ID NO:05) has little detectable activity on (S) aryl alcohols, such as (S)-1-phenyl-2-propanol, (S)-4-phenyl-2-butanol, but it is highly active on 2-butanol. A single point mutation introduced by site-directed mutagenesis significantly altered TeSADH substrate specificity: the W110A TeSADH mutant uses (S)-1-phenyl-2-propanol, (S)-4-phenyl-2-butanol, and the corresponding ketones as substrates, but not the corresponding (R)-alcohols. W110A TeSADH's kinetic parameters on (S)-1-phenyl-2-propanol, phenylacetone, (S)-4-phenyl-2-butanol, and benzylacetone are in the same range as those of TeSADH on 2-butanol, demonstrating that W110A TeSADH is excellent catalyst on these substrates. In particular, W110A TeSADH is twice as efficient on benzylacetone as TeSADH is on 2-butanol, and it produces (S)-4-phenyl-2-butanol from benzylacetone with an enantiomeric excess above 50%, and more particularly above 99%. One of the characteristics of the chemical reactions is the capability for secondary ADH to catalyze reversible reactions. In some embodiments, secondary alcohols are converted into ketones. In some embodiments, ketones are converted into secondary alcohols.

W110A TeSADH is optimally active at 87.5° C.-2.5° C. below the wild-type TeSADH enzyme. It is less stable at 90° C. but more stable at 85° C. than wild-type TeSADH is at 90° C., indicating that the W110A mutation is only slightly destabilizing. W110A TeSADH is active on aryl derivatives of phenylacetone and benzylacetone, indicating that it could potentially have other synthetic uses. Its activity, stability, and enantiomeric specificity make W110A TeSADH a useful catalyst for chiral synthesis of aryl derivatives of alcohols. The W110A and another TeSADH mutant constructed in this study did not have the substrate specificity predicted by the first set of modeling studies described herein. Further modeling studies using the structure of the horse liver ADH in a ternary complex with a substrate and $NAD^+$ showed that (S)-2-butanol's orientation in TbSADH's catalytic site in the structure of the TbSADH•(S)-2-butanol binary complex does not reflect the substrate's orientation in the enzyme-substrate-cofactor ternary complex.

TeSADH was chosen as a target enzyme for the present inventions to develop a catalyst able to produce 1-phenethyl alcohol and 1-phenyl-2-propanol from acetophenone and phenylacetone, respectively. One-phenethyl alcohol has a variety of uses as an antimicrobial agent, a chiral reagent, a flavoring agent, and an additive in dyes and fragrances. (CHEMFNFO, 2002, online posting date). One-phenyl-2-propanol is important to the pharmaceutical industry because it is an immediate precursor to amphetamine and amphetamine derivatives (Liese et al., 2000, Wiley-VCH, Weinheim, New York; herein incorporated by reference).

TeSADH is naturally inactive on acetophenone and phenylacetone. During the development of the present invention a catalytic site point mutation was designed and then actually constructed, W110A, that allowed TeSADH to become active on phenylacetone, producing 1-phenyl-2-propanol. W110A TeSADH was shown to be active on benzylacetone, and demonstrated specificity for (S)-4-phenyl-2-butanol and (S)-1-phenyl-2-propanol. (S)-4-phenyl-2-butanol is also important to the pharmaceutical industry because it is used as a precursor to anti-hypertensive agents and spasmolytics (anti-epileptic agents) (Liese et al., 2000, Wiley-VCH, Weinheim, New York; herein incorporated by reference).

EXPERIMENTAL

The following examples serve to illustrate certain embodiments and aspects of the present invention and are not to be construed as liming the scope thereof. In the experimental disclosures that follow, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); pg (picograms); L and l (liters); ml (milliliters); μl (microliters); cm (centimeters); mm (millimeters); μm (micrometers); nm (nanometers); U (units); min (minute); s and sec (second); k (kilometer); deg (degree); ° C. (degrees Centigrade/Celsius).

Example 1

Materials and Methods

The following is a brief description of exemplary materials and methods that were used in subsequent Examples. Further descriptions are shown in Ziegelmann-Fjeld, et al., (2007) Protein Engineering, Design & Selection 20(2):47-55; Musa, et al., (2007) J. Org. Chem. 72:30-34; and Musa, et al., (2007) Angew. Chem. Int. Ed. 2007, 46:3091-3094; all of which are herein incorporated by reference in their entirety.

Chemicals. The racemic (rac), (S)-, and (R)-forms of 1-phenyl-2-propanol, racemic 4-phenyl-2-butanol, $NaIO_4$, $Na_2Cr_2O_7 \cdot 2H_2O$, and isopropenyl acetate were purchased from Aldrich (St. Louis, Mo.). Benzylacetone was purchased from ACROS Organics (Morris Plains, N.J.). *Candida Antarctica* lipase immobilized on acrylic resin was purchased from Sigma (L4777).

Phenylacetone Synthesis. Phenylacetone was synthesized from (rac)-1-phenyl-2-propanol as described Vondervoot et al., (2002) Synlett, 2:243-246, herein incorporated by reference, with a modification were the reaction was performed at room temperature instead of 4° C. as previously published. An exemplary yield was 33%. $^1$H NMR spectra were recorded on a Varian Mercury Plus 400 spectrometer at 400 MHz $^1$H NMR (CDCl$_3$): δ 7.2-7.4 (m, 5H), δ 3.7 (s, 2H), δ 2.2 (s, 3H). In brief, phenylacetone was synthesized from (rac)-1-phenyl-2-propanol as described Vondervoot et al., (2002) Synlett, 2:243-246, herein incorporated by reference), with a modification were the reaction was performed at room temperature instead of 4° C. as previously published. An exemplary yield was 33%. $^1$H NMR spectra were recorded on a Varian Mercury Plus 400 spectrometer at 400 MHz $^1$H NMR (CDCl$_3$): δ 7.2-7.4 (m, 5H), δ 3.7 (s, 2H), δ 2.2 (s, 3H). In brief, distilled water (25 ml), 70% aq HNO$_3$ (0.080 g, 0.88 mmol), and Na$_2$Cr$_2$O$_7$.2H$_2$O (0.048 g, 0.16 mmol) were mixed in a 100 ml-flask equipped with a mechanical stirrer. NaIO$_4$ (3.76 g, 17.6 mmol) was added at maximum speed of mechanical stirring. Subsequently, a solution of (rac)-1-phenyl-2-propanol (2.18 g, 16 mmol) in CHCl$_3$ (25 ml) was added in one portion. The mixture was vigorously stirred for 24 h at room temperature. The organic layer was separated from the aqueous layer, which was subsequently extracted with CH$_2$Cl$_2$ (2×25 ml). The combined organic layer was dried over Na$_2$SO$_4$, and the solvent was evaporated under reduced pressure to produce oil. The residual oil was purified by chromatography on a silica gel column (ethyl acetate/n-hexane=1/8) to give pure phenylacetone. An exemplary phenylacetone yield was 33%. $^1$H NMR spectra were recorded on a Varian Mercury Plus 400 spectrometer at 400 MHz $^1$H NMR (CDCl$_3$): δ 7.2-7.4 (m, 5H), δ 3.7 (s, 2H), δ 2.2 (s, 3H).

(S)-4-phenyl-2-butanol synthesis and kinetic resolution of 4-phenyl-2-butanol. (S)-4-Phenyl-2-butanol was produced from (rac)-4-phenyl-2-butanol by kinetic resolution as described (Choi et al., 2004), with the exception that the ruthenium catalyst and tert-butoxide were omitted. (S)-4-Phenyl-2-butanol and (R)-1-methyl-3-phenylpropyl acetate were produced in exemplary quantitative yields after a 5-day reaction at room temperature. In brief, racemic 4-phenyl-2-butanol (2.10 g, 14.0 mmol), isopropenyl acetate (2.10 g, 21.0 mmol), and lipase (42 mg) in toluene (50 ml) were mixed together in a 100-ml flask equipped with a mechanical stirrer. The reaction mixture was stirred at room temperature for 5 days. The reaction was monitored by GC to check the complete conversion of (R)-4-phenyl-2-butanol to the corresponding acetate. Capillary GC was performed on a Varian 3300 gas chromatograph with FI detection (Superco β-Dex 120 chiral column, 30m×0.250 mm id, 0.25 μm film thickness) programmed between 110° C. and 115° C. (1.5° C./min). The reaction mixture was filtered and concentrated at 50° C. under reduced pressure. The residue was chromatographed on a silica gel column (ethyl acetate/hexane=⅛) to give (S)-4-phenyl-2-butanol and (R)-1-methyl-3-phenylpropyl acetate in exemplary quantitative yields.

(S)-4-Phenyl-2-butanol $[α]_D$+13.5 (c=3.9, CHCl$_3$) $^1$H NMR (CDCl$_3$): δ 7.2-7.4 (m, 5H), δ 3.8 (m, 1H), δ 2.8 (m, 2H), δ 1.80 (m, 3H), δ 1.3 (d, 3H).

(R)-1-Methyl-3-phenylpropyl acetate $^1$H NMR (CDCl$_3$): δ 7.2-7.4 (m, 5H), δ 4.9 (m, 1H), δ 2.7 (m, 2H). δ 2.1 (s, 3H), δ 1.8 (m, 2H), δ 1.3 (d, 3H).

Preparation of (R)-4-phenyl-2-butanol. (R)-4-phenyl-2-butanol was then produced from (R)-1-methyl-3-phenylpropyl acetate by saponification. In brief, (R)-4-phenyl-2-butanol was then produced from (R)-1-methyl-3-phenylpropyl acetate by saponification. In brief, (R)-1-Methyl-3-phenylpropyl acetate (1.00 g, 5.20 mmol) and NaOH (0.31 g, 7.8 mmol) were dissolved in methanol/water (1:1) (40 ml) in a 100-ml flask equipped with a mechanical stirrer. The reaction mixture was refluxed for 1.5 hours then extracted with CH$_2$Cl$_2$ (3×20 ml). The combined organic layer was dried over Na$_2$SO$_4$ and concentrated under reduced pressure to produce (R)-4-phenyl-2-butanol. An exemplary yield was 90%. $[α]_D$-14.9 (c=3.9, CHCl$_3$) $^1$H NMR (CDCl$_3$): δ 7.2-7.4 (m, 5H), δ 3.8 (m, 1H), δ 2.7 (m, 2H). δ 1.8 (m, 2H), δ 1.6 (s, 1H), δ 1.3 (d, 3H).

Modeling. Modeling was done manually in InsightII (Accelrys, San Diego, Calif.) on a Silicon Graphics Octane 2 computer. Protein structures were obtained at the Research Collaboratory for Structural Bioinformatics (RCSB) Protein Data Bank (PDB) (Berman, et al., (2003) Nature Structural Biology 10 (12):980) website (www.pdb.org/; herein incorporated by reference).

Modeling active sites for identifying a target point mutation. The TbSADH•(S)-2-butanol complex (PDB ID: 1BXZ; Brockii; Li, et al., (1999) Proteins 37:619-627; herein incorporated by reference) was superimposed with the TbSADH•NADP+ complex (PDB ID: 1YKF; NADP-Dependent Alcohol Dehydrogenase From *Thermoanaerobium Brockii*; Korkhin, et al., in Perspectives on Protein Engineering, "from Folds to Functions", 5th International Conference, 2-6 Mar. 1996, Montpellier, France 39; Korkhin et al., 1998, J. Mol. Biol. 278:967-981; herein incorporated by reference) in InsightII. After superimposition, the entire 1BXZ structure, except for the (S)-2-butanol molecule, was removed, and the (S)-2-butanol was merged with the 1YKF structure. The result was a single TbSADH enzyme structure containing NADP$^+$, Zn$^{2+}$, and (S)-2-butanol. The 3D-structure of (S)-1-phenyl-2-propanol was generated with CORINA-Gasteiger Research. A substrate was fitted in the active site of the new TbSADH•(S)-2-butanol•NADP$^+$ complex), their reactive oxygen superposed with that of (S)-2-butanol. Modeling active sites using horse liver ADH.

In a second modeling approach, the inventors started from the structure of the horse liver ADH (HLADH) co-crystallized with a substrate (i.e., p-bromobenzyl alcohol, BRB) and NAD$^+$ (PDB # 1HLD). The TbSADH•(S)-2-butanol-NADP$^+$ model was superimposed with the structure of the HLADH•BRB•NAD$^+$ complex using the conserved catalytic site residues for the alignment. Starting from the (S)-1-phenyl-2-propanol pdb file the inventors generated in CORINA, the inventors further generated the lowest energy conformations of this substrate using Omega (OpenEye Scientific Software, Santa Fe, N. Mex.). Individual conformations were then fitted manually into the TbSADH catalytic site, their C—OH bond superimposed with that of BRB in HLADH. All individual conformations of (S)-1-phenyl-2-propanol were manually rotated around their C—OH bond axis to identify orientations that would minimize steric overlap between atoms of the substrate and active site residues. One of the seven (S)-1-phenyl-2-propanol conformations tested (the lowest energy conformation) created steric overlap with a single residue, Trp110, in TeSADH's catalytic site. Other (S)-1-phenyl-2-propanol conformations created overlaps with more than one residue.

The 3D structures of the mutant enzymes were modeled using the SWISS-MODEL program with the TbSADH•NADP$^+$ complex as the template. The wild-type enzyme was also modeled as a control to detect any changes that may be modeling artifacts. The models were superimposed with the TbSADH crystal structure to determine how much, if any, the backbone of the mutant structure deviated from the crystal structure.

Mutagenesis

Mutations W110A and Y267G were introduced by site-directed mutagenesis (SDM) using PCR (Burdette et al. Biochem. J. 302:163-1707; herein incorporated by reference). The wild-type adhB gene in the pADHBIM1-kan plasmid (a pBluescript II KS+-kanamycin derivative) (Burdette et al., 1997, Biochem. J. 326:717-724; Burdette et al., 1996, Biochem. J. 316:115-1227; all of which are herein incorporated by reference) was used as the template. Primers were synthesized by the Macromolecular Structure Facility, Biochemistry Department, Michigan State University. For unknown reasons the *T. ethanolicus* adhB gene does not lend itself to single-step mutagenesis using protocols such as Stratagene's QuikChange® Site-Directed Mutagenesis Kit. Therefore, mutagenesis was performed in two steps using the Expand High Fidelity PCR System (Roche, Indianapolis, Ind.).

In step 1, primers 5'-ATCAATATGTCATATGAT-GAAAGGTTTTGCAATGC (SEQ ID NO:14) (A, where CATATG encodes a 5' NdeI site) and 5'-CATTC-GAAAATTTCGCGCCTGCCAGC (SEQ ID NO:15) (where CGC creates the WhOA mutation) or 5'-AGGACCATCTT-TAGGGTTTACAATATC (SEQ 11D NO:16) (where AGG creates the Y267G mutation), were used to create the W110A or Y267G mutation in the 5' end of the gene, and primers 5'-GCTGGCAGGCGCGAAATTTTCGAATG (SEQ ID NO:17) (where GCG creates the W110A mutation) or 5'-GATATTGTAAACCCTAAAGATGGTCCT (SEQ ID NO:18) (where CCT creates the Y267G mutation), and 5'-GT-CATCTCGAGTGCTAATATTACAACAGGTTTG (SEQ ID NO:19) (B, where CTCGAG encodes a 3' XhoI site) were used to create the W110A or Y267G mutation in the 3' end of the gene. In step 2, the complete adhB gene was reconstructed using the two PCR products from step 1 as co-templates and oligonucleotides A (SEQ ID NO:14) and B (SEQ ID NO:19) as primers.

The PCR products were subcloned into the PCR 2.1-TOPO vector (Invitrogen, Carlsbad, Calif.) and transformed into "Chemically Competent One Shot TOP10 *E. coli* cells" (Invitrogen, Carlsbad, Calif.). The recombinant plasmids were purified from the TOP10 cells for automated sequencing at the Michigan State University Genomics Facility. Mutant sequences were compared to the wild-type adhB sequence using a ClustalW multiple sequence alignment program. Genes containing only the W110A (SEQ ID NO:02 or SEQ ID NO:04) or the Y267G mutation (SEQ ID NO:06) were then subcloned into pET24a(+) (Novagen, Madison, Wis.) for expression. W110A TeSADH pET24a(+) constructs were subcloned into competent *E. coli* and expressed in HB101 (DE3) and BL21 (DE3) (Novagen) cells using methods well known in the art. In these constructs and bacteria, W110A and Y267G TeSADHs were expressed as fusion proteins with a C-terminal His$_6$ tag.

Protein Expression.

W110A TeSADH was purified using the Gibco BRL procedure for Protein Expression System, pRoEX-1 vector (cat. no. 10197-010, Gaithersburg, Md.). *E. coli* (cells) containing the gene construct are grown up overnight in 5 mL LB with kanamycin (20 µg/ml). This overnight culture was centrifuged at 5000 rpm for 5-10 min then resuspended in 1 mL LB medium, of which the 1 ml was used to inoculate 500 mL of LB medium containing kanamycin (20 µg/ml). The inoculated medium is incubated until the population density reaches an OD$_{600}$ ranging from 0.6 to 1.0. Expression of the gene construct was induced with the addition of 1 mM IPTG to the medium and then incubated for 3 hours. The induced cells are then centrifuged at 5000 rpm for 20 min, the medium was removed and the pellet was resuspended in lysis buffer with the bacteria lysed in a French pressure cell. The lysed cells are then heated to 80° C. for 15 min (this step is done because the desired protein is thermostable but being expressed in a mesophillic host, so the heat destroys most of the other proteins). The solution is then centrifuged at 10,000 rpm for 10 min to pellet all the cell debris and denatured proteins. The supernatant is then loaded on a Qiagen Ni-NTA column, washed and eluted with a Tris buffer system containing imidazole. The resulting protein is run on an SDS-PAGE to check for purity, and the concentration is measured using BioRad Protein Dye using the bovine serum albumin as a control. Finally the protein solution was frozen in 250 µl aliquots at −80° C. for months without affecting enzyme activity.

Cultures of *E. coli* were grown in 500 ml LB medium (per liter: 10 g tryptone, 5 g yeast extract, and 5 g NaCl) containing 100 µg/l kanamycin. When the culture reached an OD$_{600}$ of 0.6-1.0, W110A TeSADH expression was induced with 1 mM IPTG (isopropyl-beta-D-thiogalactopyranoside) for 5 hours. Thereafter, cells were spun down (5,000 rpm for 20 min) and resuspended in 4 volumes of lysis buffer (50 mM Tris-HCl [pH 8.5], 10 mM 2-mercaptoethanol, 1 mM PMSF (Phenylmethylsulphonylfluoride) per 1 gram of cells. The cells were lysed in a French pressure cell and the lysate was spun down (10,000 rpm for 10 min) to remove the cell debris. The crude extract was heat-treated at 85° C. for 15 min to inactivate non-thermostable proteins, and then spun down (10,000 rpm for 10 min.) to remove the denatured proteins. The cleared crude extract was loaded on a 5-ml Ni-NTA (Qiagen, Valencia, Calif.) column.

Purification of Histidine Tagged Protein.

Preparation of Stock Solutions: 1 M Tris-HCL (pH~8.5): 12.1141 g Tris(2-Amino-2-(hydroxymethyl)-1,3-propanediol)/100 mL water, pH to 8.5 at 4° C. (pH 7.85 at 25° C.), 1 M Tris base: 12.1141 g Tris base/100 mL water, 2 M KCl: 74.55 g KCl/500 mL water, 1 M imidazole: 9.8517 g imidazole/150 mL water, Tris buffer was prepared at pH~8.5 at 4° C. without the addition of a chelating agent, such as DTT (1,4-dithiothreitol), EDTA (ethylenediaminetetraacetic acid) or the like. 100 mM PMSF: 17.4 mg/mL, Ethanol. For SDS-PAGE, fractions containing imidazole were heated to 37° C. for 10 minutes instead of boiling.

Preparation of Buffers: Lysis Buffer: 50 mM Tris-HCl (pH 8.5), 10 mM 2-mercaptoethanol, 1 mM PMSF at 4° C., for example, 60 mL of Lysis Buffer: 1.34 mL 1 M Tris-HCl, 1.66 mL 1 M Tris base, 0.042 mL 2-mercaptoethanol (add just before using), 0.6 mL 100 mM PMSF (add just before using), 56.36 mL water.

Buffer A: 20 mM Tris-HCL (pH~8.5), 100 mM KCl, 20 mM imidazole, 10 mM 2-mercaptoethanol, 10% (v/v) glycerol at 4° C., for example, 2.5 L (or 500 mL), 22.4 (4.48) mL 1 M Tris-HCl, 27.6 (5.52) mL 1 M Tris base, 125 (25) mL 2 M KCl, 50 (10) mL 1 M imidazole, 1.75 (0.35) mL 14.3 M 2-mercaptoethanol (add just before using), 250 (50) mL 100% glycerol (molecular biology grade), 404.65 (404.65) mL water.

Buffer B: 20 mM Tris-HCL (pH~8.5), 1 M KCl, 10 mM 2-mercaptoethanol, 10% (v/v) glycerol at 4° C., for example, 500 mL of Buffer: (or 100 mL), 4.5 (0.9) mL 1 M Tris-HCl, 5.5 (1.1) mL 1 M Tris base, 125 (50) mL 2 M KCl, 0.35 (0.07)

mL 14.3 M 2-mercaptoethanol (add just before using), 50 (10) mL 100% glycerol (molecular biology grade), and 189.65 (37.93) mL water.

Buffer C: 20 mM Tris-HCL (pH~8.5), 100 mM KCl, 100 mM imidazole, 10 mM 2-mercaptoethanol, 10% (v/v) glycerol at 4° C., for example, 1 L (or 200 mL): 9 (1.8) mL 1 M Tris-HCl, 11 (2.2) mL 1 M Tris base, 50 (10 mL 2 M KCl, 100 (20) mL 1 M imidazole, 0.70 (0.14) mL 14.3 M 2-mercaptoethanol (add just before using), 100 (20) mL 100% glycerol (molecular biology grade), 729.30 (145.86) mL water.

Preparation of Ni-NTA Column

Prepare a column with Ni-NTA resin, (for example, 1 mL resin is sufficient to purify approximately 4-8 mg of 6×His-tagged protein): a) mount column on solid support, b) transfer desired amount of Ni-NTA resin to a centrifuge tube and centrifuge 1,500×g for 5 minutes, c) remove supernatant and mix resin with 1 volume of wash buffer [Buffer A (Tris-based), Buffer D (phosphate-based), or your specific wash buffer], d) carefully pour the slurry into the column, and e) equilibrate the column with 5-10 volumes of wash buffer (Buffer A without the P at 4° C. at a flow rate of 1 mL/minute.

Preparation of Cell Extract

Incubate overnight (for growing) a 5 mL culture: a) spin down the overnight culture; resuspend in 5 mL fresh media, b) Inoculate 500 mL media with the 5 mL of overnight culture and allow to grow to 0.6-1 $OD_{660}$, c) induce culture with 1 mM IPTG and allow to incubate 3-4 hours, d) spin down culture in pre-weighed 250 mL centrifuge bottles at 5000 rpm for 20 minutes. At this point the centrifuge bottles with the cell pellets can be placed at −80° C. for overnight storage, e) resuspend cell pellet in lysis buffer (1 g cells per 4 volumes lysis buffer), f) lyse cells with the French press. Alternatively, sonicate until 80% cell lysis is achieved. For calculating % cell lysis: dilute 5 μL of cell suspension prior to sonication in 995 μL of water. Measure $A_{590susp}$ and record result. Sonicate cells and dilute 5 μL of sonicated cells in 995 μL of water. Measure $A_{590susp}$ and record result. % cell lysis =1−$(A_{590sonic}/A_{590susp})$, f) transfer lysate to sterile centrifuge tubes, g) heat extracts to 80° C. (instead of 85° C. for non-thermoproteins) for 15 minutes, and g) Centrifuge cell debris at 10,000 rpm for 10 minutes.

Purification of Protein in Tris buffer: a) Load sample on pre-equilibrated column, b) wash column with 10 volumes of Buffer A, c) wash column with 2 volumes of Buffer B, d) wash column with 2 volumes of Buffer A, e) elute with 5-10 volumes of Buffer C, f) collect 0.5 mL fractions or collect the single peak, alternatively, if a peak tails badly or the protein does not come off the column a higher concentration of imidazole may be needed. Alternatively, an imidazole gradient to may be used to elute off the protein.

Reuse of the Ni-NTA Resin.

The reuse of the Ni resin depends on the nature of the sample. Reuse should be performed with identical recombinant proteins with a maximum of 3-5 runs per column. When the Ni-NTA resin is to be used to purify a different recombinant protein or changes in color from light blue-green to brownish or grey, use fresh resin or regenerate used resin according to the following procedure by washing the column with the following in sequential order: a) volumes of 6 M guanidine hydrochloride/0.2 M acetic acid, b) 2 volumes of water, c) 3 volumes of 2% SDS, d) 1 volume of 25% EtOH, e) 1 volume of 50% EtOH, f) 1 volume of 75% EtOH, g) 5 volumes of 100% EtOH, h) 1 volume of 75% EtOH, i) 1 volume of 50% EtOH, j) 1 volume of 25% EtOH, k) 1 volume of water, l) 5 volumes of 100 mM EDTA, pH 8.0, m) 2 volumes of water, n) recharge the column with 2 volumes of 100 mM $NiSO_4$, o) wash the column with 2 volumes of water, p) wash the column with 2 volumes of 6 M guanidine hydrochloride/0.2 M acetic acid, and q) equilibrate column in Buffer A for the next run.

Enzyme Assays.

Activities of the wild-type, Y267G, and W110A TeSADHs were first tested in crude extracts from 5-ml cultures as described herein and in Burdette and Zeikus, 1994, Biochem. J. 302:163-170), with (rac)-2-butanol, (rac)-1-phenethyl alcohol, (rac)-1-phenyl-2-propanol, (rac)-4-phenyl-2-butanol, and phenylacetone as substrates. Assays were done in the presence of 50 mM Tris-HCl [pH 8.0] and 0.4 mM $NADP^+$ (alcohol oxidation), or pH 6.5 and 0.4 mM NADPH (ketone reduction). Initial velocity was measured spectrophotometrically at 60° C. by following NADPH production (alcohol oxidation) or consumption (ketone reduction) at 340 nm for 1 min in a Varian Cary 300 UV/Vis spectrophotometer equipped with a Peltier heating system. The enzyme was preincubated for at least 5 min at 40° C. before being added to the assays. The same conditions were used to test activity of the purified W110A TeSADH with (rac)-2-butanol; (S)- and (R)-1-phenyl-2-propanol; (S)- and (R)-4-phenyl-2-butanol; benzylacetone; phenylacetone; and the aryl derivatives (1 mM each) 1-chloro-3-phenyl-2-propanol, 3-chloro-3-methyl-4-phenyl-2-butanone, (2-fluorophenyl)acetone, and 1-(4-bromophenyl)acetone. One unit of activity was defined as the amount of enzyme needed to consume or produce 1 μmol of NADPH per minute.

Temperature Effects.

Enzyme assays were performed at temperatures from 5° C. to 97° C., with 10 mM (rac)-1-phenyl-2-propanol as the substrate to determine the effect of temperature on activity.

Kinetic Parameters.

To determine W110A TeSADH's kinetic parameters, enzyme assays were performed with (rac)-2-butanol (0.5-500 mM), (S)-1-phenyl-2-propanol (0.05-10.5 mM), (S)-4-phenyl-2-butanol (0.05-10 mM), benzylacetone (0.05-5 mM), and phenylacetone (0.05-7.5 mM) at 60° C. for 1 min in 50 mM Tris-HCl at pH 8.0 (alcohol oxidation) or pH 6.5 (ketone reduction) in the presence of 0.4 mM NADP(H). At least eight substrate concentrations were used for each data set and each set was performed in triplicate. The $K_m$ and $V_{max}$ values of W110A TeSADH were calculated using the Non-Linear Curve Fit tool of Origin 6.1 (OriginLab Corporation, Northampton, Mass.).

Ph Effects.

Enzyme assays were performed at pH values from 4.0 to 9.1 with 5 mM (rac)-4-phenyl-2-butanol as the substrate in order to determine the effect of pH on activity. Ketone reduction assays were performed in citrate buffer (pH 4.0 to 7.2) and Tris buffer (pH 7.0) in the presence of 0.4 mM NADPH. Alcohol oxidation assays were performed in citrate buffer (pH 7.0 and 7.2) and Tris buffer (pH 7.0 to 9.1) in the presence of 0.4 mM $NADP^+$. Assays at each pH were performed in triplicate.

Asymmetric Reduction of Benzylacetone to the Corresponding Sec-Alcohol.

A mixture of 0.3 mmol benzylacetone, 1.31 μmol (0.131 mM final concentration) $NADP^+$ and 0.56 mg W110A TeSADH in 10.0 ml Tris-HCl (pH 6.5)/isopropanol (70:30) was stirred at 50° C. for 12 h before being extracted with $CH_2Cl_2$. The organic layer was then concentrated under vacuum. The residual compound was purified on a silica gel column. The absolute configuration and enantiomeric excess of the produced alcohol were determined by comparing the sign value of the optical rotation with those reported previously for (S)-, and (R)-4-phenyl-2-butanol (Nakamura et al., 1999, J. Chem. Soc. Perkin Trans. 1:2397-24027; herein incorporated by reference).

Stability Assays.

Enzyme kinetic stability was tested as described (Burdette et al., 2000, Enzyme. Microb. Technol. 27:11-18; herein incorporated by reference) at 85° C. and 90° C. for W110A TeSADH, and 90° C. for TeSADH. Activity assays on the heat-treated enzymes were performed with 5 mM (rac)-4-phenyl-2-butanol (W110A TeSADH) and 5 mM 2-butanol (TeSADH). Fifty μl of the 0.2 mg/ml W110A TeSADH inactivation solution (10 μg enzyme) or 30 μl of the wild-type inactivation solution (6 μg enzyme) was added to each appropriate assay. Inactivation curves were performed in triplicate. They were fit using the Non-Linear Curve Fit tool of Origin 6.1.

W110A TeSADH solvent stability was tested with the same procedure as the thermostability tests (Burdette et al., 2000, Enzyme. Microb. Technol. 27:11-187; herein incorporated by reference) with 30% 2-propanol as the substrate in the incubating enzyme solutions. Time points were taken every 30 min for 2 hours. Fifty μL of the 0.2 mg/ml W110A TeSADH (10 μg per assay) in 30% 2-propanol (195 mM final concentration) inactivation solution was added to each enzyme assay. Activity assays were performed in 50 mM Tris-HCl (pH 8.0) containing 0.4 mM $NADP^+$.

Example 2

Modeling and Mutagenesis

It was previously been shown with TbSADH that large substrates, such as 2-decanone, are reduced to the corresponding alcohol at very low rates. In contrast, TbSADH is not significantly active on substrates containing rings with more than three carbons (Keinan et al., 1986, J. Am. Chem. Soc. 108:162-1697; herein incorporated by reference); because the bulk of the ring does not fit in the active site. Therefore, mutations of the present invention increased the size of the active site for accommodating the large phenyl rings of 1-phenethyl alcohol and 1-phenyl-2-propanol.

Figure 2:
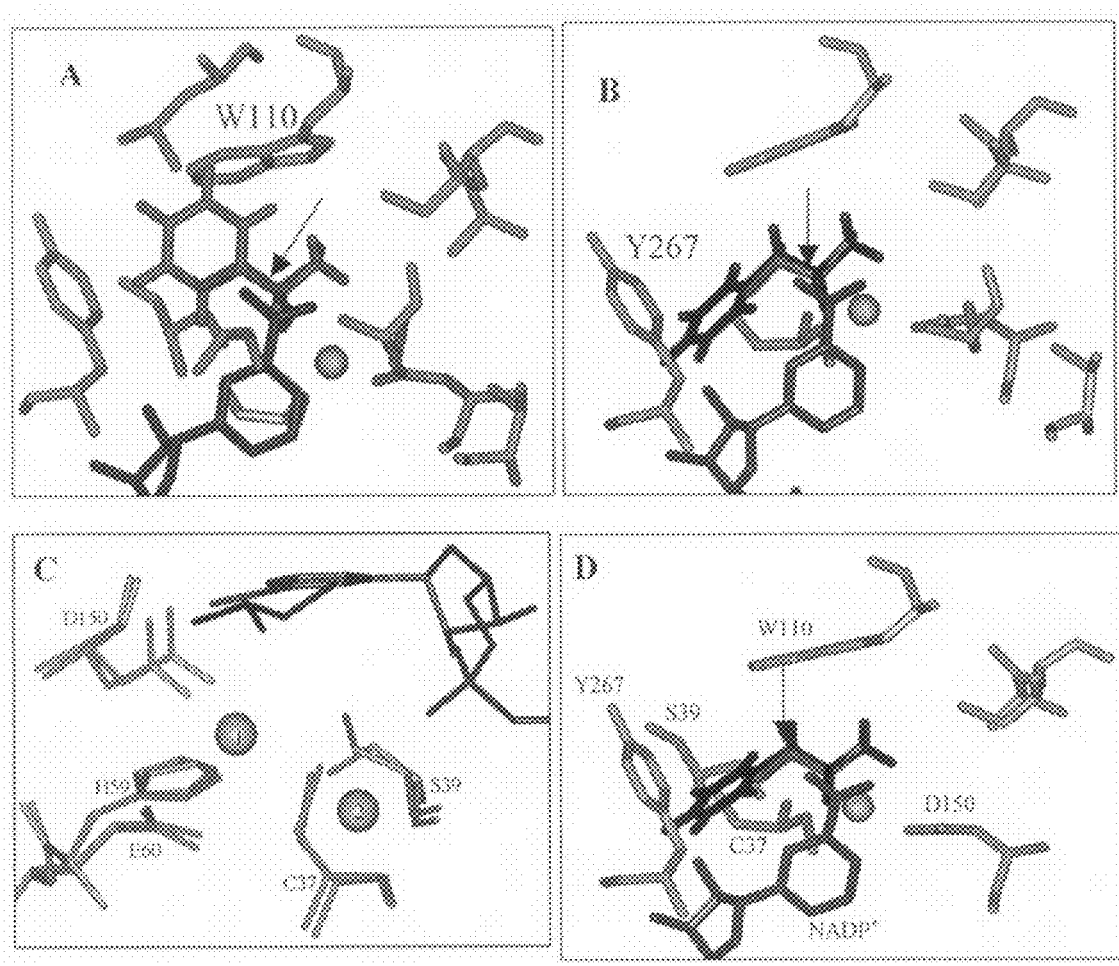
FIG. 2 shows exemplary models of a TbSADH active site in complex with NADP⁺, Zn²⁺, 2-butanol, and (S)-1-phenethyl alcohol (A) or (S)-1-phenyl-2-propanol (B), where pink/: 2-butanol; and blue/dark grey: (S)-1-phenethyl alcohol (A) or (S)-1-phenyl-2-propanol (B), C) and D) exemplary modeling of the TbSADH•(S)-2-butanol and the TbSADH•(S)—NADP⁺ binary complexes into a single, TbSADH•(S)-2-butanol•(S)—NADP⁺ model, blue: 2-butanol. The two structures were superimposed in InsightII using the heavy atoms of catalytic site residues C37, S39, H59, E60, Asp150, L294, and C295. Balls 1 and 2 denote the positions of the catalytic Zn²⁺ in the TbSADH•(S)—NADP⁺ and TbSADH•(S)-2-butanol binary complexes, respectively, blue/dark grey: 2-butanol. Green/light grey: TeSADH residues; red/medium grey: NADP⁺; orange/ball: Zn²⁺.

When the inventors superimposed the TbSADH•(S)-2-butanol and TbSADH•$NADP^+$ complexes, the inventors observed that the 2-butanol molecule in the TbSADH•(S)-2-butanol complex almost overlapped $NADP^+$'s nicotinamide ring in the TbSADH•$NADP^+$ complex (FIG. 2). In addition, the catalytic $Zn^{2+}$ moves by more than 1 Å between the two structures. These observations suggest that the positions in which $NADP^+$'s nicotinamide ring is oriented in the TbSADH•$NADP^+$ complex and/or the position in which 2-butanol is oriented in the TbSADH•(S)-2-butanol complex do not reflect their orientations in an active enzyme-substrate-cofactor ternary complex. In PDB structure #1 HLD, HLADH is co-crystallized with a substrate (i.e., p-bromobenzyl alcohol, BRB) and $NAD^+$. When the inventors superimposed this structure with those of the TbSADH•(S)-2-butanol and the TbSADH•$NADP^+$ complexes (1BXZ and 1YKF, respectively; FIG. 3A), the inventors saw that (i) the orientation of (S)-2-butanol in TbSADH's catalytic site did not correspond to that of BRB in HLADH, and (ii) that $NADP^+$'s nicotinamide ring in the TbSADH•$NADP^+$ complex was rotated by almost 90° in comparison to $NAD^+$'s nicotinamide ring in the HLADH•BRB•$NAD^+$ ternary complex.

Because HLADH is a primary ADH that showed low activity on secondary alcohols, it was unclear how well the orientation of the substrate in TeSADH should match that in HLADH. For this reason, the inventors decided to adopt two modeling and mutagenic strategies: one based on the orientation of (S)-2-butanol in a TbSADH•(S)-2-butanol•$NADP^+$ ternary model (construction described in the Materials and Methods) and one based on the orientation of BRB in the HLADH•BRB•$NAD^+$ ternary complex.

Figure 4:
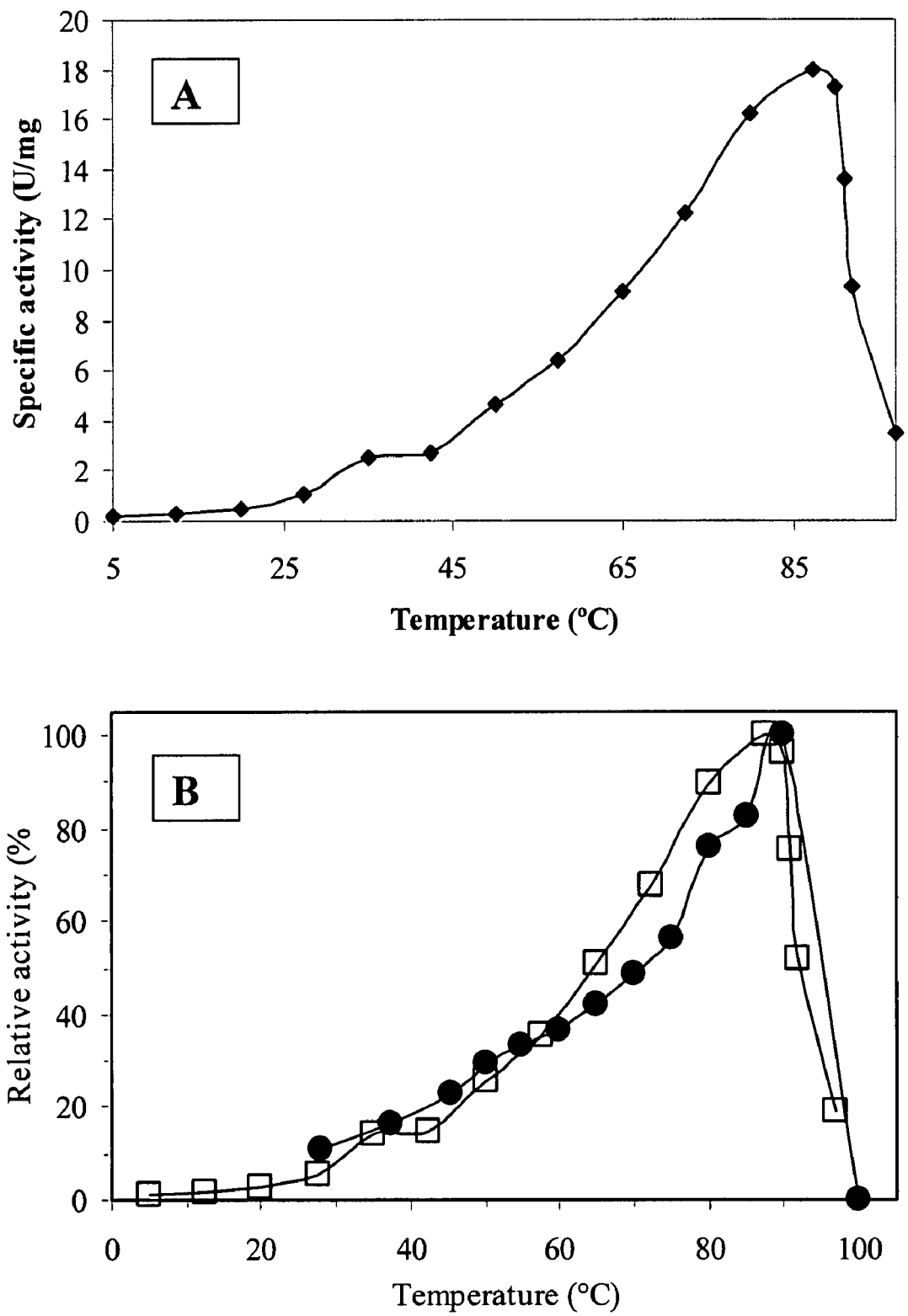
FIG. 4 shows an exemplary effect of temperature on A) W110A TeSADH activity with (rac)-1-phenyl-2-propanol as the substrate and B) exemplary temperature activity profiles of W110A TeSADH with (rac)-1-phenyl-2-propanol as the substrate (□) and of TeSADH with 2-butanol as the substrate (●).

(S)-1-Phenyl-2-propanol was fitted manually into the TbSADH•(S)-2-butanol•$NADP^+$ model with the reactive hydroxyl group superimposed with that of (S)-2-butanol. As seen in FIG. 4, the phenyl ring of (S)-1-phenyl-2-propanol is in close proximity (1.69 Å) with the Cβ of Y267. This steric clash potentially excludes (S)-1-phenyl-2-propanol from being a substrate for TeSADH. To remove this steric overlap, the inventors constructed the Y267G mutant to increase the depth of the large pocket enough to accommodate the phenyl ring of (S)-1-phenyl-2-propanol.

In the second modeling approach, seven Omega-generated conformations of (S)-1-phenyl-2-propanol were manually fitted into the TbSADH catalytic site, with their C—OH bond superimposed with that of BRB in HLADH. (S)-1-phenyl-2-propanol individual conformations were manually rotated around their C—OH bond axis to identify orientations that would minimize steric overlap between atoms of the substrate and active site residues. Two orientations of one (S)-1-phenyl-2-propanol conformation tested (the lowest energy conformation) created steric overlap with a single residue, Trp110, in TeSADH's catalytic site (FIG. 3B). All other (S)-1-phenyl-2-propanol conformations created overlaps with more than one residue. The inventors constructed the W110A mutant and removed the steric overlap between (S)-1-phenyl-2-propanol and Trp110 (FIG. 3C).

Thus W110A and Y267G mutations were individually modeled into TbSADH using SWISS-MODEL for predicting changes in the mutant structure in comparison to the TbSADH crystal structure. Wild-type TbSADH was also modeled as a check for potential artifacts in the modeling process. In both mutant 3D-models the backbones of the mutated residues, Y267G and W110A, remained unchanged, with the same ((ϕ,ψ) angles as in the wild-type crystal structure. In both mutant models the catalytic zinc shifted by 0.78 Å, and the side-chains of zinc-binding residues, His59, Cys37, Asp150, were slightly reoriented. Because these changes also occurred in the wild-type (control) model they were indeed discounted as modeling artifacts.

Mutations W110A and Y267G were then separately introduced into the *T. ethanolicus* adhB gene by site-directed mutagenesis for providing SEQ ID NO:02 and SEQ ID NO:06, respectively. Mutant TeSADHs were expressed in *E. coli* as fusion proteins with a C-terminal His6 tag. Both mutant enzymes were abundantly expressed as soluble proteins. They remained stable during a 15-min heat treatment at 85° C., suggesting that they were properly folded despite the artificially created active site mutations.

Example 3

Activity and Substrate Specificity of W110A TeSADH and Y267G TeSADH

Activity assays with heat-treated crude extracts: The activity of Y267G TeSADH was tested on heat-treated crude extracts with (rac)-1-phenethyl alcohol, (rac)-2-butanol, (rac)-4-phenyl-2-butanol, and (rac)-1-phenyl-2-propanol as substrates. Results were compared to those of heat-treated crude extracts of TeSADH. TeSADH and Y267G TeSADH relative concentrations in heat-treated crude extracts were estimated by SDS-PAGE. Y267G TeSADH showed a slight decrease in specific activity on (rac)-2-butanol (~33 U/mg) when compared to the wild-type TeSADH enzyme (~41 U/mg). Y267G TeSADH had no detectable activity on (rac)-1-phenethyl alcohol, (rac)-1-phenyl-2-propanol, or (rac)-4-phenyl-2-butanol, and was not further studied.

Similar activity assays with heat-treated crude extracts showed that W110A TeSADH is much less active on 2-butanol than TeSADH, and that it is relatively inactive on 1-phenethyl alcohol and acetophenone. Unexpectedly, W110A TeSADH showed significant activity on (rac)-1-phenyl-2-propanol, phenylacetone, and (rac)-4-phenyl-2-butanol, substrates on which wild-type TeSADH showed no activity. W110A TeSADH also showed significant activity with benzylacetone, on which wild-type TeSADH showed only slight activity. Because of these unexpected activity results, W110A TeSADH was purified to homogeneity and characterized. Initial activity assays with purified W110A TeSADH agreed with previous assays on crude extracts of W110A TeSADH (Table 1A): W110A TeSADH showed 10-fold lower activity on (rac)-2-butanol than TeSADH did; it showed almost no activity on (rac)-1-phenethyl alcohol and acetophenone; and it showed high activity levels on phenylacetone, benzylacetone, (S)-1-phenyl-2-propanol, and (S)-4-phenyl-2-butanol (Table 1A). Further assays showed that W110A TeSADH is very poorly active on (R)-1-phenyl-2-propanol and (R)-4-phenyl-2-butanol.

Example 4

Kinetic Parameters of W110A TeSADH

Whereas W110A TeSADH's Vmax on (rac)-2-butanol only decreased by about 20%, its affinity for (rac)-2-butanol decreased by more than two orders of magnitude (Table 2). This low affinity for 2-butanol explains why W110A TeSADH showed low specific activity on 10 mM (rac)-2-butanol (Table 1A). In contrast W110A TeSADH's kinetic parameters on (S)-1-phenyl-2-propanol, phenylacetone, (S)-4-phenyl-2-butanol, and benzylacetone are of the same order of magnitude as those of TeSADH on (rac)-2-butanol, making W110A TeSADH an excellent catalyst on these substrates. It is interesting to note that W110A TeSADH's Vmax and Km values on benzylacetone are higher (Vmax) and lower (Km) than those of TeSADH on (rac)-2-butanol, showing that W110A TeSADH is twice as efficient on benzylacetone as TeSADH is on (rac)-2-butanol.

TABLE 1A

Specific activities of wild-type (WT) TeSADH and W110A TeSADH with multiple substrates.[a]

| Substrate[b] | W110A (U(umol)/mg protein) | Substrate[b] | WT (U(umol)/mg protein) |
|---|---|---|---|
| 2-Butanol (10 mM) | 3.65 | 2-Butanol (7.5 mM) | 45.27 |
| (rac)-1-Phenethyl alcohol (10 mM) | 0.24 | (rac)-1-Phenethyl alcohol (10 mM) | 0.15 |
| Acetophenone (7.5 mM) | 0.94 | Acetophenone (7.5 mM) | 0.90 |
| (S)-1-Phenyl-2-propanol (7.5 mM) | 14.62 | (rac)-1-phenyl-2-propanol (10 mM) | 0.14 |
| (R)-1-Phenyl-2-propanol (7.5 mM) | 0.51 | | |
| Phenylacetone (7.5 mM) | 37.61 | Phenylacetone (7.5 mM) | 1.02 |
| (S)-4-Phenyl-2-butanol (7.5 mM) | 26.83 | (rac)-4-Phenyl-2-butanol (7.5 mM) | 0.29 |
| (R)-4-Phenyl-2-butanol (10 mM) | 0.26 | | |
| Benzylacetone (7.5 mM) | 34.58 | Benzylacetone (7.5 mM) | 5.94 |

[a]Enzyme assays were performed at 60° C. for 1 min with substrate, in 50 mM Tris-HCl pH~6.5 (reduction of ketones) or pH~8.0 (oxidation of alcohols), with 0.4 mM NADP(H).
[b]Substrate concentrations are indicated in parentheses.

TABLE 1B

Specific activity of the W110 TeSADH mutant with selected aryl derivatives.

| Substrate | Specific Activity (μmol/mg protein*min) |
|---|---|
| 1-Chloro-3-Phenyl-2-Propanol | — |
| 3-Chloro-3-Methyl-4-Phenyl-2-Butanone | 3.9 ± 0.2 |
| (2-Fluorophenyl) Acetone | 14.8 ± 0.2 |
| 1-(4-Bromophenyl) Acetone | 43.8 ± 1.9 |

TABLE 2

Kinetic parameters of the W110A TeSADH mutant with multiple substrates[a].

| | Wild-type TeSADH | | | W110A TeSADH | | |
|---|---|---|---|---|---|---|
| Substrate | $V_{max}$ (app) (U/mg) | $K_m$ (app) (mM) | $V_{max}/K_m$ (mL/min*mg) | $V_{max}$ (app) (U/mg) | $K_m$ (app) (mM) | $V_{max}/K_m$ (mL/min*mg) |
| (rac)-2-Butanol | 37 | 0.51 | 0.072 | 29.2 ± 3.6 | 80.3 ± 18 | 0.00036 |
| (S)-1-Phenyl-2-propanol | — | — | — | 16.2 ± 2.2 | 0.75 ± 0.1 | 0.022 |
| (S)-1-Phenyl-2-Butanol | — | — | — | 33.5 ± 3.4 | 0.39 ± 0.03 | 0.086 |
| Benzylacetone | — | — | — | 44.9 ± 2.8 | 0.25 ± 0.02 | 0.18 |
| Phenylacetone | — | — | — | 46.7 ± 2.5 | 0.86 ± 0.07 | 0.054 |

[a]Enzyme assays were performed at 60° C. for 1 min in 50 mM Tris-HCl pH ~6.5 (reduction of ketones) or pH ~8.0 (oxidation of alcohols), with 0.4 mM NADP(H).

Example 5

Effect of pH on Enzyme Activity

Alcohol oxidation and ketone reduction assays were performed at different pH values in citrate and Tris buffers at overlapping pHs to determine how pH affects W110A TeSADH activity.

Figure 3:
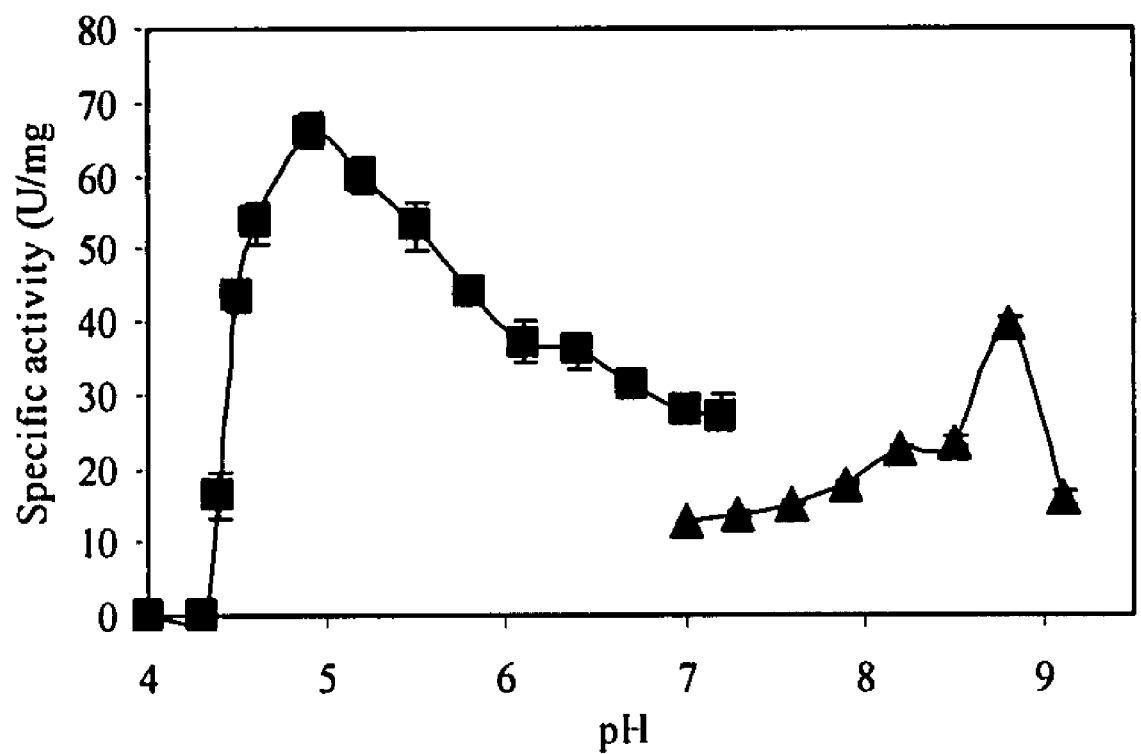
FIG. 3 shows an exemplary effect of pH on W110A TeSADH activity. Assays were performed with benzylacetone (◇, ■) and (rac)-4-phenyl-2-butanol (○, ▲) as the substrates. (◇, ▲): Sodium citrate buffer (pH 4.0 to 7.2), and (■, ○): Tris-HCl (pH 7.0 to 9.1).

Results show that the optimum pH is 4.9 for ketone reduction, and 8.8 for alcohol oxidation (FIG. 3). These results are significantly different from the TeSADH optimum pH from 6.5 for ketone reduction, and slightly different from pH 9.0 for alcohol oxidation (Burdette and Zeikus, 1994, Biochem. J. 302:163-1707; herein incorporated by reference).

Example 6

Effects of Temperature on W110A TeSADH Activity and Stability

Figure 5:
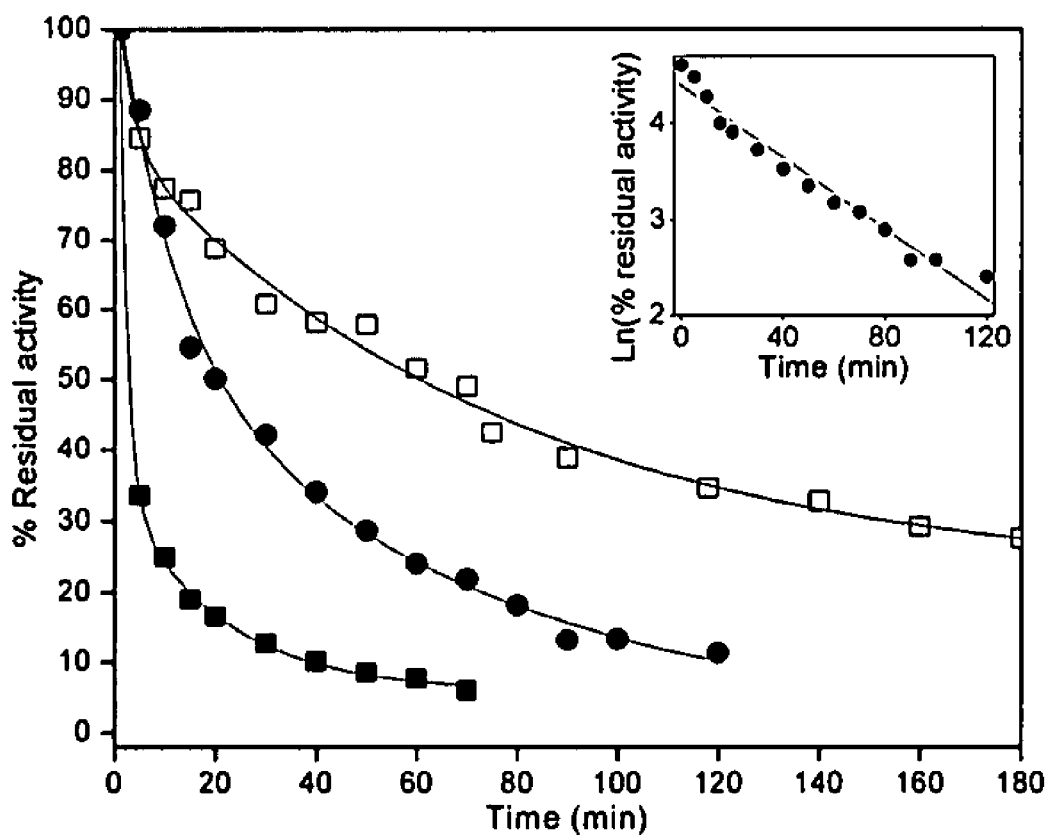
FIG. 5 shows an exemplary comparison of kinetic stability of W110A TeSADH versus TeSADH. TeSADH inactivation at 90° C. (●); W110A TeSADH inactivation at 85° C. (□); W110A TeSADH inactivation at 90° C. (■). Residual activity was measured on 5 mM (rac)-4-phenyl-2-butanol (W110A TeSADH) and 5 mM (rac)-2-butanol (TeSADH) at 60° C. for 1 minute. Inactivation curves were fitted by the sum of two exponentials. Inset: Fitting of TeSADH inactivation at 90° C. as a one-step inactivation mechanism.

Assays at temperatures ranging from 5-97° C. showed that W110A TeSADH activity increased from 5° C. to 87.5° C., with the enzyme showing maximal activity at 87.5° C., 2.5° C. below the temperature for TeSADH maximum activity (90° C.). Above 87.5° C., the activity dropped off sharply, suggesting that this enzyme starts inactivating above this temperature (FIG. 4). This exemplary small decrease in optimum temperature suggests that W110A TeSADH is destabilized in comparison to TeSADH, but that this destabilization is only marginal. W110A TeSADH kinetic inactivation data confirmed this result (FIG. 5).

Burdette (Burdette et al., 2000, Enzyme. Microb. Technol. 27:11-187; herein incorporated by reference) initially described TeSADH's kinetic inactivation as being a one-step mechanism ($R^2$=0.9654—FIG. 5 inset), however, during the development of the present inventions, TeSADH was found to be inactivated at 90° Celsius. The inventors found that TeSADH inactivation at 90° C. would not fit with a simple exponential decay function, but instead was best fitted by the sum of two exponentials ($R^2$=0.99318) showing that TeSADH goes through a two-stage decay process. This change in enzyme character may be due to an extra mutation (168A to 168D) that is found both in the TeSADH tested herein, and in W110A TeSADH, but not reported to be found in the TeSADH previously tested (Burdette et al., 1996, Biochem. J. 316:115-1227; herein incorporated by reference). 168 is a buried residue and the extra bulk of the aspartate side chain may cause a slight destabilization in this region. Further, W110A TeSADH was less stable than TeSADH at 90° C. (W110A TeSADH and TeSADH lost 94% and 71% activity, respectively, after 70 min at 90° C.), but W110A TeSADH was more stable at 85° C. than TeSADH at 90° Celsius.

These results confirm that, although mutation W110A destabilizes TeSADH to some extent, the mutant enzyme remains highly thermostable.

Example 7

Demonstration of W110A TeSADH Activity on Aryl Derivatives of Phenylacetone and Benzylacetone Usefulness of W110A TeSADH for industrial syntheses was demonstrated by testing W110A TeSADH activity on commercially available aryl derivatives of 1-phenyl-2-propanol, phenylacetone, and benzylacetone. W110A TeSADH showed significant levels of activity on 3-chloro-3-methyl-4-phenyl-2-butanone, (2-fluorophenyl)acetone, and 1-(4-bromophenyl)acetone, but showed no detectable activity on 1-chloro-3-phenyl-2-propanol (Table 3).

A small amount of 1-chloro-3-phenyl-2-propanol was tested (Sigma-Aldrich's Rare Chemical Library), however the enantiomeric composition of this alcohol was unknown. Therefore it is not know whether 1-chloro-3-phenyl-2-propanol is provided as an (R)-alcohol instead of an (S)-alcohol, so that it is not known whether W110A TeSADH inactive on a (R) or (S) substrate sample.

TABLE 3

Activity of W110A TeSADH on (1 mM) aryl derivatives[a].

| Substrate | Derivative structure | Specific activity (μmol/mg protein * min) |
|---|---|---|
| 1-Phenyl-2-propanol[b] 1-Chloro-3-phenyl-2-propanol | | 13.5 ± 2.0 ND |
| Benzylacetone[b] 3-Chloro-3-methyl-4-phenyl-2-butanone | | 37.6 ± 4.2 3.9 ± 0.2 |
| Phenylacetone[b] (2-Fluorophenyl) acetone 1-(4-Bromophenyl) acetone | | 39.8 ± 1.2 14.8 ± 0.2 43.8 ± 1.9 |

TABLE 3-continued

Activity of W110A TeSADH on (1 mM) aryl derivatives[a].

| Substrate | Derivative structure | Specific activity (μmol/mg protein * min) |
|---|---|---|
| | ![4-bromophenylacetone structure] | |

[a]Enzyme assays were performed at 60° C. for 1 min in 50 mM Tris-HCl pH~6.5 (reduction of ketones) or pH~8.0 (oxidation of alcohols), with 0.4 mM NADP(H).
[b]Substrates of W110A TeSADH that are the substructures for the aryl derivatives
ND: not detectable.

Example 8

Effect of Solvent on W110A TeSADH Stability

Figure 6:
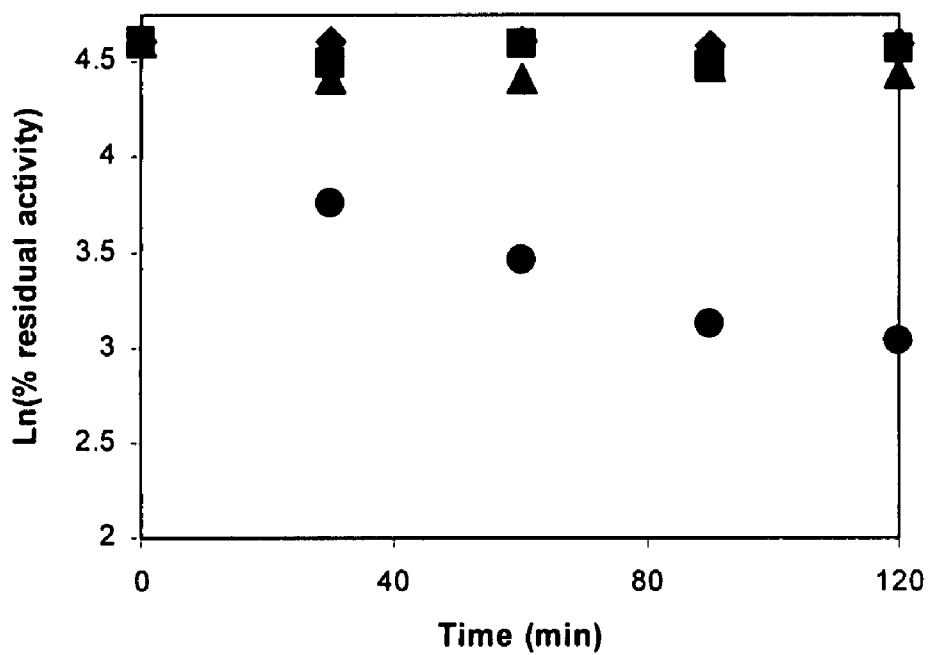
FIG. 6 shows an exemplary stability of A) W110A TeSADH in 30% 2-propanol at specified temperatures, 30° C. (♦); 40° C. (■); 50° C. (▲); 60° C. (●) B) W110A TeSADH (30° C. [◇]; 40° C. [□]; 50° C. [Δ]; and 60° C. [○]) and TeSADH (50° C. [▲] and 60° C. [●]) in 30% 2-propanol at specified temperatures.
Figure 6:
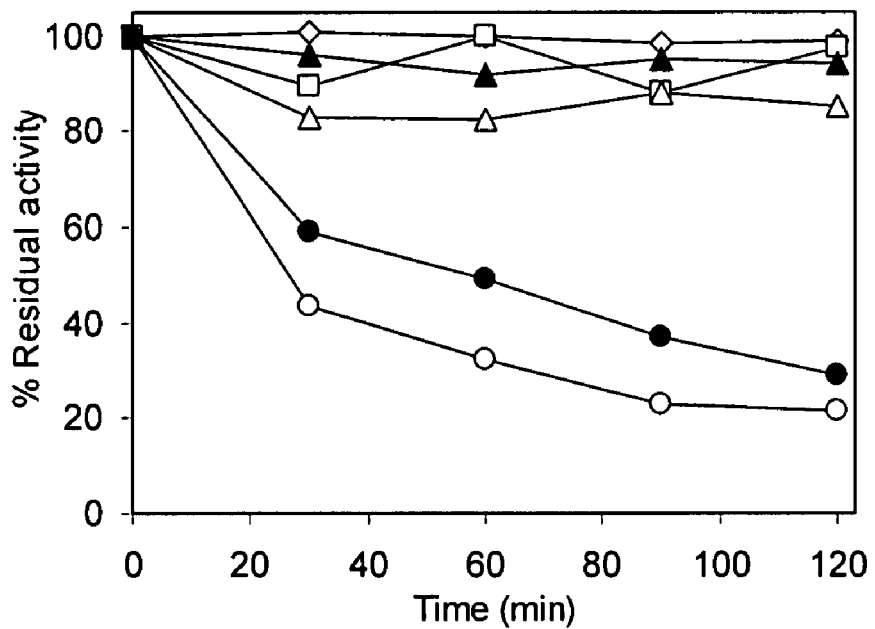
Figure 7:
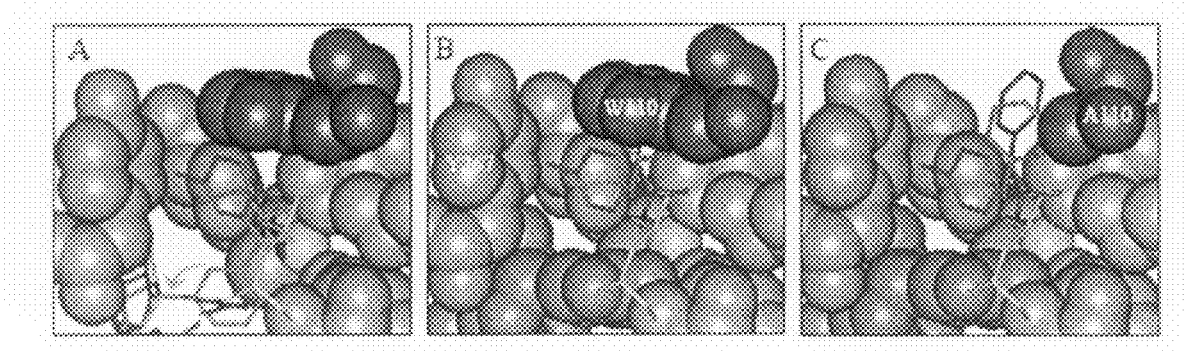
FIG. 7 shows an exemplary useful modeling of (S)-1-phenyl-2-propanol in the catalytic sites of TeSADH and W110A TeSADH when horse liver ADH is used as the base model. (A) Superposition of TbSADH•2-butanol (PDB ID: 1BXZ), TbSADH•NADP⁺ (PDB ID: 1YKF), and horse liver ADH•NAD⁺•p-bromobenzyl alcohol (BRB) (PDB ID: 1HLD). The proteins were superposed using the backbones of the zinc-binding residues, Cys36, His67, and Cys174 in horse liver ADH, and Cys37, His59, and Asp150 in TbSADH. (B) Modeling of (S)-1-phenyl-2-propanol in TbSADH catalytic site, with its reactive hydroxyl group superposed with that of BRB. Two orientations of (S)-1-phenyl-2-propanol are shown. (C) W110A mutation showing how (S)-1-phenyl-2-propanol can be a substrate of W110A TeSADH. TbSADH catalytic site residues are shown (in gray, CPK representation); Leu294 is in stick representation to allow a view into the catalytic site. Blue/dark grey: NAD⁺ (sticks) and catalytic Zn²⁺ (CPK) in 1HLD; orange/medium grey: NADP⁺ in 1YKF (sticks in A, CPK in B and C); yellow/light grey: catalytic Zn²⁺ in 1YKF; and atom colors (carbon in green/light grey and oxygen in red/medium grey): substrates (BRB in PDB ID: 1HLD and 2-butanol in PDB ID: 1BXZ in A; BRB in PDB ID: 1HLD and (S)-1-phenyl-2-propanol in PDB ID: 1YKF in B and C).

W110A TeSADH solvent stability was tested in 30% 2-propanol at four different temperatures. The 2-propanol present in the inactivation solution was used as the substrate to measure residual activity (195 mM final assay concentration). Little decrease in W110A TeSADH activity was observed after incubations in the presence of 30% 2-propanol at temperatures up to 50° Celsius. However, W110A TeSADH lost 80% activity after 120 min incubation at 60° C. (FIG. 6). These results indicate that, for long reaction times in the presence of solvents, W110A TeSADH would be best used at temperatures of 50° C. or below. The demonstrated ability to operate at or below 50° C. in the presence of 30% 2-propanol would allow the use of W110A TeSADH under (i) higher concentrations of substrates that are moderately soluble in water and for (ii) cofactor recycling using wild-type TeSADH as the coupling enzyme and 2-propanol as the recycling substrate.

Example 9

Validation of Modeling Approaches Used During the Development of the Present Inventions The demonstration herein that W110A TeSADH was active on (S)-1-phenyl-2-propanol unlike Y267G TeSADH correlates with a differing orientation of (S)-2-butanol in the TbSADH•(S)-2-butanol binary complex (PDB # 1BXZ) from its orientation in an active enzyme-substrate-cofactor ternary complex. While HLADH is a primary ADH yet shows limited activity on secondary alcohols, the orientation of BRB in the HLADH•BRB•NAD+ ternary complex is contemplated as an excellent indication of how the reactive oxygen (and the corresponding C—OH bond) in secondary alcohols should be positioned in TeSADH's catalytic site to yield an active ternary complex. In summary, the inventions described herein demonstrated that a W110A mutation significantly altered the substrate specificity of TeSADH including adding a variety of phenyl-substituted alcohols and ketones. W110A TeSADH is active on benzylacetone, phenylacetone, (S)-1-phenyl-2-propanol, and (S)-4-phenyl-2-butanol while showing little or no activity on the corresponding (R)-alcohols. W110A TeSADH produces (S)-4-phenyl-2-butanol at greater than 99% enantiomer excess. W110A TeSADH is active on aryl derivatives of phenylacetone and benzylacetone in contrast to the wild-type TeSADH that demonstrates little if any activity on these aryl substrates. Thus activity and enantiomeric specificity make W110A TeSADH a useful catalyst for chiral synthesis of aryl derivatives of alcohols, in particular S-aryl derivatives of alcohols.

Example 10

This example shows further reaction capabilities of the TeSADH mutant enzymes of the present inventions, in particular on ketones comprising a phenyl ring.

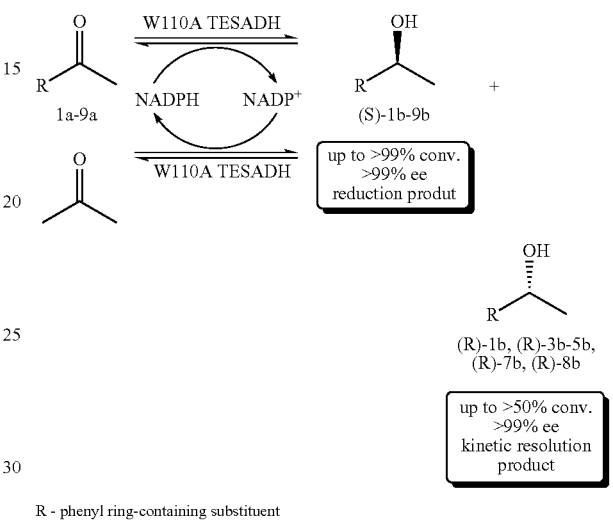

R - phenyl ring-containing substituent

As shown below, a series of phenyl ring-containing ketones, such as 4-phenyl-2-butanone (1a) and 1-phenyl-1,3-butadione (2a), were reduced with good to excellent yields and high enantioselectivities. On the other hand, 1-phenyl-2-propanone (7a) was reduced with lower ee than 2-butanone derivatives. (R)-Alcohols, anti-Prelog products, were obtained by enantiospecific oxidation of (S)-alcohols through oxidative kinetic resolution of the rac-alcohols using W110A TESADH in Tris buffer/acetone (90:10, v/v).

The following diagram and Table 4 shows the reactivity results obtained using exemplary substrates comprising phenyl rings and structural abbreviations used for this and the following EXAMPLE.

TABLE 4

Asymmetric Reduction of Phenyl Ring-Containing Ketones Using W110A TESADH.

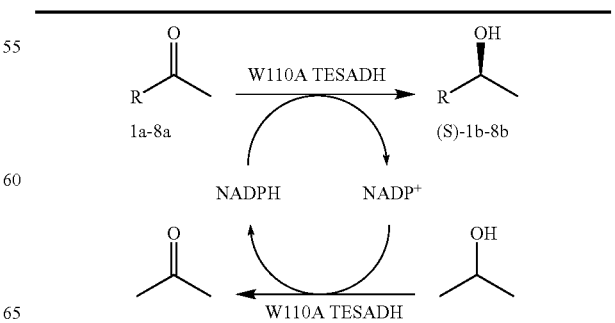

TABLE 4-continued

Asymmetric Reduction of Phenyl Ring-Containing Ketones Using W110A TESADH.

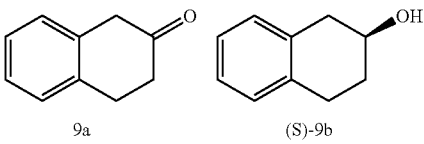

| substrate | R | producta | conv. (%)b | Ee (%)d |
|---|---|---|---|---|
| 1a | PhCH2CH2 | (S)-1b | 99 | >99 |
| 2a | pH(CdO)CH2 | (S)-2b | 98 | >99 |
| 3a | (E)-Ph—HCdCH | (S)-3b | 64 | >99 |
| 4a | p-MeOC6H4(CH2)2 | (S)-4b | 87 | 91 |
| 5a | PhOCH2 | (S)-5b | >99 | >99e |
| 6a | p-ClC6H4CH2CHCl | (2S,3R)-6b | 83c | >99 |
| 7a | PhCH2 | (S)-7b | 95 | 37e |
| 8a | p-MeOC6H4CH2 | (S)-8b | 97 | >99e |
| 9a | | (S)-9b | >99 | 71e | a The absolute configurations of the products were determined by comparison of the signs of the optical rotation with those reported previously.
b % conversion was determined by GC.
c Isolated yield.
d Unless otherwise mentioned, ee was determined by chiral stationary phase GC for the produced alcohol.
e The ee was determined for the corresponding acetate derivative.

TABLE 5

Enantiospecific Kinetic Resolution of Phenyl Ring-Containing rac-Alcohols Using W110A SADH.

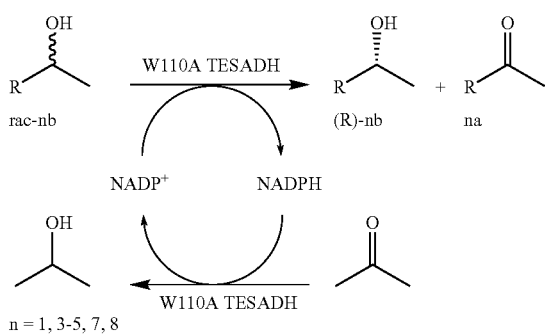

n = 1, 3-5, 7, 8

| substrate | R | producta | conv. (%)b | Ee (%)d |
|---|---|---|---|---|
| rac-1b | PhCH2CH2 | (R)-1b | 50 | >99 |
| rac-3b | (E)-Ph—HCdCH | (R)-3b | 50 | >99 |
| rac-4b | p-MeOC6H4(CH2)2 | (R)-4b | 75 | 77d |
| rac-5b | PhOCH2 | (R)-5b | 19 | 25 |
| rac-7b | PhCH2 | (R)-7b | 49 | 39d |
| rac-8b | p-MeOC6H4CH2 | (R)-8b | 48 | 92d | a The absolute configurations of the unreacted alcohols were confirmed by co-injection in a chiral column GC with their S enantiomers prepared by the asymmetric reduction of the corresponding ketones employing W110A TESADH (Table 4).
b % conversion was determined by GC.
c Unless otherwise mentioned, ee was determined by a chiral stationary phase GC for the alcohols.
d The ee was determined for the corresponding acetate derivative.

A series of phenyl ring-containing ketones, which could not be reduced by wild-type TESADH, were reduced by W110A TESADH to produce the corresponding nonracemic alcohols with good yields and high optical purities (Table 4). The reductions were carried out in Tris buffer containing 30% (v/v) 2-propanol, which served as both cosolvent and hydride source to reduce the oxidized coenzyme. The use of such a high percentage of 2-propanol was crucial for enhanced solubility of the hydrophobic phenyl ring-containing ketone substrates in aqueous media and shifted the equilibrium into the reduction direction. The produced alcohols had S configuration, in agreement with Prelog's rule, in which the NADPH cofactor transfers its pro-R hydride to the re face of the ketone (Kroutil, et al., (2004) Curr. Opin. Chem. Biol. 8:120-126; Nakamura, et al., (2003) Tetrahedron:Asymmetry 14:2659-2681; Prelog, (1964) Pure Appl. Chem. 9:119-130; all of which are herein incorporated by reference).

Phenyl ring-containing 2-butanone derivatives were reduced to the corresponding (S)-alcohols with excellent stereoselectivities and moderate to excellent yields (Table 4). 4-Phenyl-2-butanone (1a) was reduced stereoselectively to produce (S)-4-phenyl-2-butanol ((S)-1b) with excellent chemical and optical yields. The â-diketone 1-phenyl-1,3-butadione (2a) was reduced regio- and stereoselectively to furnish the monohydroxy ketone (S)-3-hydroxy-1-phenyl-1-butanone ((S)-2b) with excellent yield and ee, leaving the other keto group at C-1 intact. (E)-4-Phenyl-3-butene-2-one (3a) was reduced with moderate yield and excellent optical purity to produce the allylic alcohol (S)-4-phenyl-3-butene-2-ol ((S)-3b). The presence of the methoxy group at the para position of the phenyl ring in 4-(4-methoxyphenyl)-2-butanone (4a) affected the ee of the produced (S)-4-(4-methoxyphenyl)-2-butanol ((S)-4-b) (91% ee), which was lower than for (S)-1b. Phenoxy-2-propanone (5a) was reduced with very high yield and optical purity to produce the corresponding (S)-phenoxy-2-propanol ((S)-5b). When the R-chloroketone, 3-chloro-4-(4-chlorophenyl)-2-butanone (6a), was reduced with W110A TESADH, (+)-(2S,3R)-3-chloro-4-(4-chlorophenyl)-2-butanol ((+)-(2S,3R)-6b) was produced with high enantioselectivity (>99% ee) and diastereoselectivity (92:8 mixture of anti- and syn-R-chlorohydrins).

Figure 8:
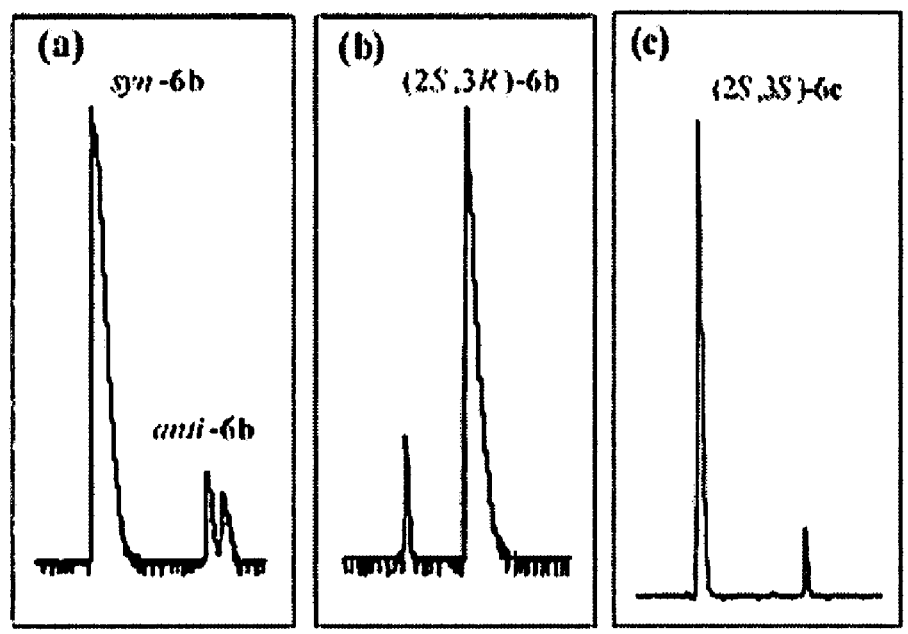
FIG. 8 shows exemplary GC chromatograms illustrating (a) the products of NaBH4 reduction of 6a, (b) the products of W110A TESADH reduction of 6a, and (c) (−)-(2S,3S)-6c produced from (+)-(2S,3R)-6b.

The absolute configuration of (+)-(2S,3R)-6b was confirmed by comparing the sign of the optical rotation with that reported previously for the very similar compound, (+)-(2S,3R)-4-phenyl-3-bromo-2-butanol) ([R]$^{20}$D+29.2, c 2.08, CHCl3; lit. 14 [R]25J+37, c 0.06, CHCl3, 95% ee). In a separate experiment, reduction of 6a with NaBH4, which expected to give mainly the syn product (Usami, et al., (2005) Chem. Lett. 34:1062-1063; herein incorporated by reference) afforded a mixture of four diastereomers ((±)-6b) (88:12 mixture of syn- and anti-R-chlorohydrins), in which the syn-6b had a different retention time than (+)-(2S,3R)-6b by injection in a chiral column GC (FIGS. 8a,b).

Reduction of 6a to almost a single stereoisomer, (+)-(2S,3R)-6b, using W110A TESADH indicated that the process involves a KR, and this should be combined with isolation of (S)-6a as unreacted enantiomer and a maximum yield of 50% of the produced R-chlorohydrin. The inventors observed an exemplary yield higher than 50%, and the isolated unreacted 6a was a racemic mixture. This indicates that the reduction of 6a with W110A TESADH proceeds by dynamic kinetic resolution via a facile buffer-catalyzed enolization, which enables the unreacted enantiomer (S)-6a to racemize after the depletion of (R)-6a starts (Feske et al., (2005) Org. Chem. 70:9654-9657; herein incorporated by reference). The R-chlorohydrin (+)-(2S,3R)-6b was then converted quantitatively to the corresponding epoxide, (−)-(2S,3S)-4-(4-chlorophenyl)-2,3-epoxybutane ((−)-(2S,3S)-6c), without racemization using 1,8-diazabicyclo-[5.4.0]undec-7-ene (DBU) (Scheme 1 below, FIG. 8c) (Schubert, et al., (2002) Angew. Chem., Int. Ed. 41:634-636; herein incorporated by reference). The absolute configuration of (−)-(2S,3S)-6c was confirmed by the comparison of the sign of optical rotation with that reported for the very similar compound (−)-(2S,3S)-4-phenyl-2,3-epoxybutane ([R]20D-26.2, c 2.32, CHCl3; lit. 14 [R]25J=27, c 0.04, CHCl3, >98% ee).

SCHEME 1. Conversion of (+)-(2S, 3R)-6b into (−)-(2S, 3S)-6c.

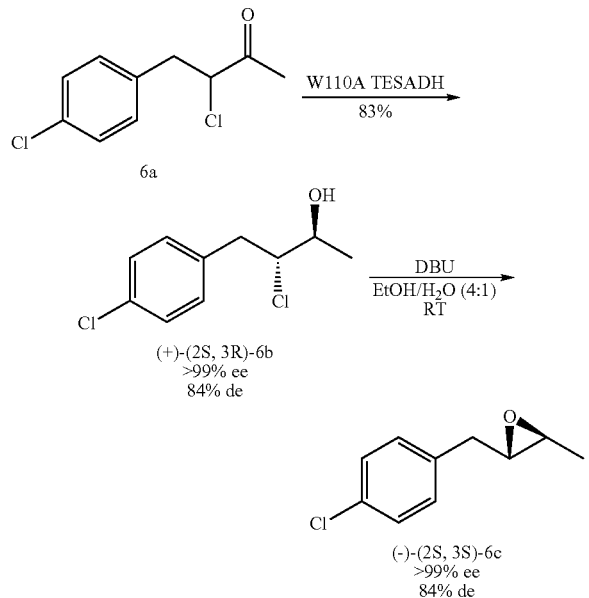

Unexpectedly, 1-phenyl-2-propanone (7a) was reduced to produce (S)-1-phenyl-2-propanol ((S)-7b) with poor enantioselectivity, indicating that 7a can fit in alternative modes in the active site within the large pocket, allowing the NADPH cofactor to deliver its pro-R hydride from either re or si faces. 1-(4-Methoxyphenyl)-2-propanone (8a) was reduced to produce (S)-1-(4-methoxyphenyl)-2-propanol ((S)-8b) with excellent chemical yield and ee, which means that the sterically bulky para methoxy substituent in 8a restricts the substrate to a single binding mode within the active site. The cyclic ketone 2-tetralone (9a) was reduced with high yield and moderate stereopreference to produce (S)-2-tetralol ((S)-9b). Enzymatic asymmetric reduction of substrates with sterically hindered groups on both sides of the carbonyl, like 9a, was of great interest because these substrates are typically either poor or non-substrates for ADHs; therefore, very few ADHs are able to achieve such asymmetric reductions (Kroutil, et al., (2004) Curr. Opin. Chem. Biol. 8:120-126; Yadav, et al., (2002) J. Org. Chem. 67:3900-3903; all of which are herein incorporated by reference).

Oxidation via KR of phenyl ring-containing rac-alcohols was used to produce their (R)-alcohols, the anti-Prelog configurated alcohols, as unreacted enantiomers with moderate to high enantiomeric ratios using W110A TESADH. The reactions were carried out in Tris buffer containing 10% (v/v) acetone. The amount of acetone needed was less than the amount of 2-propanol used in the reduction pathway simply because alcohols are more soluble than their corresponding hydrophobic ketones in aqueous media. As with all KRs, these reactions suffer from the limitation that the maximum theoretical yield with high enantiomeric ratio of a single enantiomer, (R) in this case, was 50% (Table 5). As expected, the substrates reduced with high ee showed high stereospecificities in the oxidation pathway and vice versa.

The enantiospecific oxidation via KR using W110A TESADH exclusively oxidized the S enantiomers of rac-1b and rac-3b to the corresponding ketones 1a and 3a, respectively, leaving their (R)-alcohols as unreacted enantiomers with excellent enantiomeric ratios (Table 5). The production of optically active 1b was important as it was a precursor for antihypertensive agents, such as bufeniode and labetalol (Stampfer, et al., (2003) J. Org. Chem. 68:402-406; Johnson, et al., (2000) Pharmacotherapy 20:622-628; all of which are herein incorporated by reference). For rac-4-b, it was resolved by oxidative KR to furnish (R)-4-b with moderate stereopreference (77% ee at 75% conversion). Under the same conditions, KR of rac-5b furnished (R)-5b with 25% ee at an exemplary 19% conversion, indicating that the KR of this alcohol takes place with high enantiomeric discrimination. Even with addition of more enzyme and acetone, we were not able to push the reaction to higher yield. The racemic 1-phenyl-2-propanol (rac-7a) was resolved, as expected, with low enantiospecificity because it was reduced with low ee. (S)-1-(4-Methoxyphenyl)-2-propanol ((S)-8b) was oxidized with excellent enantioselectivity to its corresponding ketone 8a, leaving (R)-8b as enantiomerically pure unreacted enantiomer. Although 9a was reduced with high yield and moderate ee, rac-9b was not oxidized by W110A TESADH. The same results for rac-9b were obtained by Stampfer et al. using Rhodococcus ruber DSM 44541 (Stampfer, et al., (2003) J. Org. Chem. 68:402-406; herein incorporated by reference).

Resistance of TESADH to organic cosolvents allowed the redox reactions in both directions to be carried out at relatively high substrate concentration (35 mM in the reduction pathway and 70 mM in the oxidation pathway). The design of new TESADH mutants such as W110A TESADH in addition to TESADH's resistance to organic solvents and high concentrations of substrates make this enzyme useful for synthetic applications.

The following materials and methods were used for this example.

Materials. Commercial grade solvents were used without further purification. NADP+, Novozyme 435, and NaBH4 were used as purchased from commercial sources. Substrates 1a-6a, 9a, rac-1b, rac-7b, (R)-7b, and (S)-7b were used as purchased from commercial suppliers. 7a and 8a were prepared as described previously (King, et al., (1951) J. Am. Chem. Soc. 73:4911-4915). rac-3b, rac-4-b, rac-5b, rac-8b, and rac-9b were prepared by reducing the corresponding ketones with NaBH4 (Yadav, et al., (2002) J. Org. Chem. 67:3900-3903).

General Procedure for Asymmetric Reduction of Phenyl Ring-Containing Ketones with W110A TESADH. Reactions were conducted with 0.34 mmol of substrate, 2 mg of NADP+, and 0.75 mg of W110A TESADH in 10.0 mL of 50 mM Tris-buffer (pH 8.0)/2-propanol (70:30, v/v). The reaction mixture was stirred at 50° C. for 10 h, and then it was extracted with 3×5 mL of CH2-Cl2. The combined organic layers were dried with Na2SO4 and concentrated under vacuum. The remaining residue was analyzed by chiral column GC to determine the percent conversion and ee of the produced alcohols and then purified with silica gel using hexane/ethyl acetate (85/15) (95/5 for 6b).

(+)-(2S,3R)-3-Chloro-4-(4-chlorophenyl)-2-butanol ((+)-(2S,3R)-6b). [R]20D+29.2 (c 2.08, CHCl3)>99% ee, 84% de. 1H NMR, ä: 1.33 (d, 3H, J) 6.4 Hz), 1.91 (brs, 1H), 2.91 (dd, 1H, J) 14.6 Hz, J) 9.8 Hz), 3.10 (dd, 1H, J) 14.6 Hz, J) 4.2 Hz), 3.96 (qd, 1H, J) 6.4, J) 4.0), 4.14 (td, 1H, J) 9.6, J) 4.0), 7.17 (d, 2H, J) 8.0), 7.29 (d, 2H, J) 8.0). 13C NMR, ä: 18.8, 39.2, 69.4, 70.3, 128.9, 130.8, 132.9, 136.3. HRMS calculated for C10H12OCl2 [M+H]+, 219.0343; found, 219.0347.

General Procedure for Kinetic Resolution of Phenyl Ring-Containing Racemic Alcohols with W110A TESADH. Reactions were conducted with 0.34 mmol of substrate, 1 mg of NADP+, and 0.38 mg of W110A TESADH in 5.0 mL of 50 mM Tris-buffer/acetone (90:10) (v/v). The reaction mixture was stirred at 50° C. for 12 h, and then it was extracted with 3×5 mL of CH$_2$Cl$_2$. The combined organic layers were dried with Na2SO4 and concentrated under vacuum. The remaining residue was analyzed by chiral stationary phase GC to determine the percent conversion to ketone and ee of the unreacted (R)-alcohol.

Synthesis of (−)-(2S,3S)-4-(4-Chlorophenyl)-2,3-epoxybutane ((−)-(2S,3S)-6c)

This compound was prepared from (2S,3R)-6b using a known procedure for epoxidation (Schubert, et al., *Angew. Chem., Int. Ed.* 2002, 41, 634-636; herein incorporated by reference). [R]20D −26.2 (c 2.32, CHCl3)>99% ee, 84% de. 1H NMR, ä: 1.23 (d, 3H, J) 5.2 Hz), 2.71-2.80 (m, 4H), 7.10 (d, 2H, J) 8.4), 7.20 (d, 2H, J) 8.8). 13C NMR, ä: 17.1, 37.9, 54.6, 59.6, 128.8, 130.5, 132.6, 136.1. HRMS calculated for C10H11OCl [M+H]+, 183.0576; the inventors found, 183.0571.

Determination of Absolute Configuration. The absolute configurations of the following compounds were determined by comparing of the sign of the optical rotation with that reported in the literature: (S)-1b,20 (S)-2b,21 (S)-3b,22 (S)-4-b,23 (S)-5b,24 (S)-7b,25 (S)-8b,26 and (S)-9b (Stampfer, et al., (2003) J. Org. Chem. 68:402-406; herein incorporated by reference). The absolute configuration of (S)-7b was also demonstrated by co-injection on a chiral column GC with commercially available (R)-7b and (s)-7b. The absolute configuration of (S)-1b was confirmed by co-injection on a chiral column GC with (R)-1b, which was prepared by KR of rac-1b using Novozyme 435.27 The absolute configurations of (R)-1b, (R)-3b, (R)-4-b, (R)-5b, (R)-7b, and (R)-8b were elucidated by co-injection on GC using a chiral stationary phase with S enantiomers prepared from asymmetric reduction of the corresponding ketones using W110A TESADH.

Chiral GC chromatogram for both enantiomers of the acetate derivatives of alcohols 1b-5b and 7b-9b. Optical rotation values for (S)-1b-5b and (S)-7b-9b. 1H NMR and 13C NMR spectra for compounds (S)-1b-5b, (S)-7b-9b, (+)-(2S, 3R)-6b, and (−)-(2S,3S)-6c. This material was available via the Internet at pubs.acs.org; herein incorporated by reference).

Example 11

This example demonstrates exemplary advantages of compositions comprising and methods using a gel-sol formulation comprising mutant TeSADH enzymes of the present inventions. Please see Table 4 for an explanation of the abbreviations used for chemicals in this example.

The observations shown herein demonstrated that the mutant TeSADH enzymes of the present inventions were able to reduce phenyl-ring-containing ketones at concentrations of 35 mm to produce their corresponding S-configured alcohols in Tris-HCl buffer solution/2-propanol (70:30 v/v; Tris=tris (hydroxymethyl)aminomethane), however, the inventors contemplated that higher substrate concentrations would be required for practical production of optically active alcohols.

Herein, the inventors report the use of encapsulated W110A TeSADH in sol-gel glasses to overcome the aforementioned contemplated limitation. Specifically, in 2003, Gröger et al. reported a practical asymmetric enzymatic reduction of poorly water-soluble ketones by using an ADH-compatible biphasic reaction medium [15; herein incorporated by reference]. One problem associated with using mixed aqueous and organic solvents as reported, was that water-miscible or -immiscible solutions used for enzymatic reactions had a tendency to form emulsions in the workup, which caused problems of product separation. It was contemplated that when the water, necessary for enzyme activity, was entrapped with the enzyme within the sol gel, the workup procedure was simplified by using water-immiscible organic solvents, and therefore emulsion formation was avoided. Therefore, the inventors improved upon the early formulation as described herein. Specifically, a simple and efficient non-covalent immobilization method was used for TeSADH mutant enzymes, wherein the enzymes were encapsulation in transparent porous silicate glasses prepared by a sol-gel method, for example, [4; herein incorporated by reference]. For review examples, silicate glasses allowed the transport of small molecules, but not enzyme molecules, into and out of the glasses pores [5; herein incorporated by reference]. The sol-gel encapsulation enzymes showed advantages over non-encapsulated enzymes, such as ease of recycling, broad applicability, cost effectiveness, and safety. [3; herein incorporated by reference]

For this example, commercial grade solvents were used without further purification. NADP+, tetramethyl orthosilicate (TMOS), 1a-3a, and 6a were used as purchased from commercial suppliers. Compounds 4a and 5a were prepared as described previously [25; herein incorporated by reference].

Preparation of sol-gel ane enzyme stock: the silica sol was prepared by mixing TMOS (2.10 g), distilled water (0.47 g), and HCl (0.04m, 3 drops). The mixture was then sonicated until one layer was formed. The gels were prepared by mixing the above sol (1.0 mL) with enzyme stock (1.0 mL) in a 10 mL round-bottomed flask. The enzyme stock was prepared in 50 mm Tris-HCl buffer solution (pH 8.0) such that the concentration of the enzyme was 0.43 mgmL-1 and that of NADP+ was 3.0 mgmL-1. The sol gel was then left in the same flask and closed with Parafilm at room temperature for 48 h to allow gel aging. In the case of the hydrogel, the gel was then used without further treatment. The hydrogel was dried at room temperature in air for 24 h to give hydrated silica SiO2.nH$_2$O, the so-called xerogel.

Preparation of sol-gel-encapsulated W110A TeSADH: Gel-sol encapsulated enzyme was prepared partially as previously reported, [5, 16; herein incorporated by reference] with modifications described herein. In particular, the sol gel was kept in Tris-HCl buffer solution medium until it was used as a wet sol gel (hydrogel). The asymmetric reduction of 4-phenyl-2-butanone (1a) to (S)-4-phenyl-2-butanol ((S)-1b), a precursor for the synthesis of bufeniode and labetalol (antihypertensive agents) [17; herein incorporated by reference], was used as a model in the screening reactions in this study. The hydrogelencapsulated W110A TeSADH was used to reduce 1a to (S)-1b in several different solvent systems (Table 6). The reduction carried out in aqueous buffer solution gave almost the same yield as with the free enzyme [14a; herein incorporated by reference]. However, the same sol gel was reused three more times to give 56%, 30%, and 10% conversion, respectively. 2.0 mg of NADP+ was added for every new reaction because NADP+ molecules either escaped from the pores of the sol-gel glasses or become inactivated during turnover [18a; herein incorporated by reference].

Asymmetric reduction using xerogel-encapsulated W110A TeSADH in organic solvents: Unless otherwise mentioned, all reactions were performed with W110A TeSADH (0.43 mg) and NADP+ (3.0 mg) encapsulate d in sol gel, substrate (0.34 mmol), 2-propanol (600 mL), and organic solvent (2.0 mL) in a 10 mL round bottomed flask equipped with a magnetic stirrer. The reaction mixture was stirred at 508 C for 12 hours. The sol gel was then removed by filtration and washed with ethyl acetate (2×2 mL). The combined organic solvent was then concentrated under vacuum, and the remaining residue was analyzed by chiral-column GC to determine the yield. The residue was then converted into the corresponding acetate ester derivative to determine the ee value of the product alcohol by GC.[23]

The asymmetric reduction of 1a was also carried out in Tris-HCl buffer solution/acetonitrile/2-propanol (41:41:18 v/v) to produce (S)-1b in good yield (81%). When the same sol gel was reused, the yield was lower (43%). This indicates that W110A TeSADH was not inactivated by polar solvents. In all cases (S)-1b was produced with high enantioselectivity (>96% ee). The asymmetric reduction of 1a to (S)-1b was also performed in hexane and diisopropyl ether to give good to moderate conversions (80% and 40%, respectively) by using hydrogel-encapsulated W110A TeSADH (Table 6). Although 1a was reduced with a higher yield in the aqueous medium by using sol-gel-encapsulated W110A TeSADH, the use of organic solvents makes the process more efficient by allowing high concentrations of substrates (approximately 140 mm) to be used. It also makes this asymmetric reduction accessible to hydrophobic substrates.

The W110ATeSADH hydrogel was dried in air for 24 h to form a xerogel ($SiO_2.nH_2O$). When this xerogel was used for asymmetric reduction of 1a in Tris-HCl buffer solution/2-propanol (70:30 v/v), it gave the same conversion as that achieved by the hydrogel (Table 1). Asymmetric reduction of 1a by using the xerogel-encapsulated W110A TeSADH in hexane gave 74% conversion as compared with 80% with the hydrogel form. These results indicate that the xerogel retains the essential water molecules required for enzyme activity [18b; herein incorporated by reference]. Use of the xerogel instead of the hydrogel was preferable as it simplifies the workup procedure [18c; herein incorporated by reference].

Capillary GC measurements: Measurements were made with a Varian 3300 GC equipped with a flame-ionization detector and a Supelco b-Dex 120 chiral column (30 m, 0.25 mm (internal diameter), 0.25 mm film thickness) by using He as the carrier gas. Products were isolated and characterized as described previously [14a]. Their absolute configurations were determined by coinjection on a chiral-column GC with their S- or R-configured alcohols, which were prepared by asymmetric reduction of the corresponding ketones or kinetic resolution of the corresponding racemates by using free W110A TeSADH[14a].

The lower yield for the asymmetric reduction with a solgel-encapsulated enzyme compared with the reduction using free enzyme [14a] could be due to the slow diffusion of 140 mm substrate concentrations. 1-Phenoxy-2-propanone (2a) was reduced with a very high yield and enantioselectivity to produce (S)-1-phenoxy-2-propanol ((S)-2b). (S)-4-(4'-Methoxyphenyl)-2-butanol ((S)-3b) was obtained from the enantioselective reduction of 4-(4'-methoxyphenyl)-2-butanone (3a) with a moderate yield and a higher enantioselectivity when compared with the same alcohol produced by asymmetric reduction with free W110A TeSADH in Tris-HCl buffer solution (Table 7) [14a; herein incorporated by reference].

Although 1-phenyl-2-propanone (4a) was reduced to (S)-1-phenyl-2-propanol ((S)-4-b) with high yield but a rather low ee value (37%) in aqueous media, [14a; herein incorporated by reference] the inventors were unexpectedly obtained a better yield and significantly improved enantioselectivity (69% ee) by using xerogel W110A TeSADH in hexane.

The asymmetric reduction of 4a was also performed by using xerogel W110A TeSADH in toluene, tert-butyl alcohol, and diisopropyl ether to produce (S)-4-b with 55, 63, and 73% ee, respectively. This indicates that the solvent can affect the enzyme enantioselectivity [19; herein incorporated by reference]. The lower yield in toluene (Table 7) may be due to competitive inhibition of aromatic ketone binding by toluene. The enantioselectivity of the reduction of 4a by W110A TeSADH correlates neither with the hydrophobicity nor with the dipole moment of the solvent. This was consistent with the recent study of ADH-catalyzed reactions in biphasic systems by Filho et al., [20] who reported that a single physicochemical parameter does not predict the biocompatibility of organic solvents but rather the solvent functionality would be of great significance. 1-(4'-Methoxyphenyl)-2-propanone (5a) was reduced by using the xerogel W110A TeSADH with a lower yield but the same ee value when compared with that using the free enzyme, which produces (S)-1-(4-methoxyphenyl)-2-propanol ((S)-5b). The cyclic ketone, 2-tetralone (6a), was reduced to the corresponding (S)-2-tetralol ((S)-6b) by the xerogel with yields comparable with that produced by using free W110A TeSADH in aqueous medium. However, the ee value of (S)-6b was improved in hexane by using the xerogel (Table 7).

The low enantioselectivity observed in the reduction of 4a and 6a was a result of binding of these substrates in alternative ways within the large pocket of the active site, [14a] allowing NADPH to deliver its pro-R hydride to either the Re face or the Si face of the substrate. The improvement in enantioselectivity observed when these substrates are reduced by the xerogel W110A TeSADH in organic solvents was likely due to differences in solvation of the enzyme active site [21; herein incorporated by reference]. In an aqueous environment, the binding of a large substrate must displace solvent water from the active site. The binding of the substrate in the "wrong" orientation may actually displace more water, making it favorable entropically [22; herein incorporated by reference]. In a nonaqueous medium, this entropic advantage was contemplated as diminished.

The inventors contemplated that active-site solvation plays a significant role in the stereospecificity of aliphatic secondary alcohols by TeSADH.[23] The inventions described herein demonstrate a preparative scale asymmetric reduction by using xerogel-encapsulated ADH in pure organic solvent media. The inventors clearly demonstrated misconceptions that practical nonaqueous enzymology was limited to hydrolases were false.

In summary, the tolerance of TeSADH to high concentrations of organic solvents allowed asymmetric reduction of phenyl-ring-containing hydrophobic ketones by using xerogel-encapsulated W110A TeSADH. Sol-gel immobilization was a convenient method for reusing the enzyme and for making the enzyme accessible to a wide variety of water insoluble substrates by switching the traditional aqueous medium to organic media. This new gel-sol method allowed for the use of high concentrations of substrates that are crucial for largescale synthetic applications. Reusable catalysts for chemo-, regio-, and enantioselective asymmetric reduction are contemplated for industrial applications.

TABLE 6

Asymmetric reduction of 1a by using sol-gel-encapsulated W110A TeSADH in different media.[a]

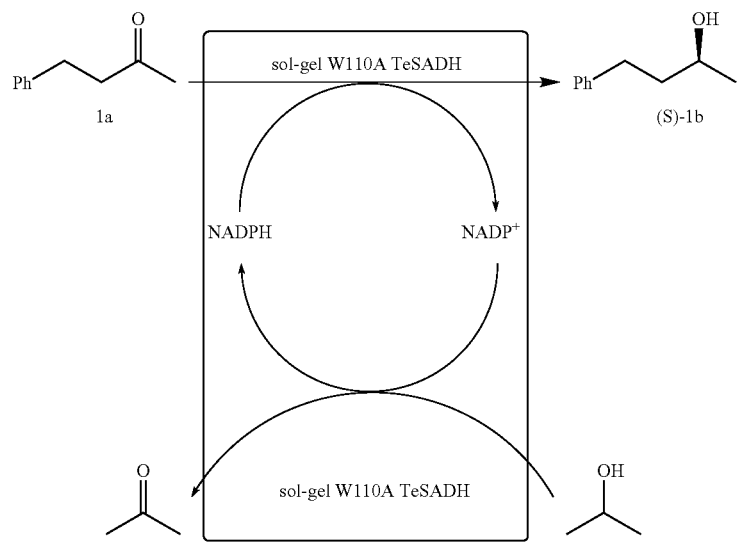

| Solvent | Hydrogel | | Xerogel | |
| --- | --- | --- | --- | --- |
| | Conv. [%][b] | ee [%][c] | Conv. [%][b] | ee [%][c] |
| 50 mM Tris-HCl pH 8.0[d] | 93 (1st) | 98 | 92 | 98 |
| | 56 (2nd) | 98 | | |
| | 30 (3rd) | 98 | | |
| | 10 (4th) | 98 | | |
| 50 mM Tris-HCl/ CH$_3$CN (1:1)[d] | 81 (1st) | 97 | — | — |
| | 43 (2nd) | 97 | — | — |
| hexane | 80 | 96 | 74 | 97 |
| diisopropyl ether | 40 | 97 | — | — |

[a]Unless otherwise stated, all reactions were performed at 508C by using sol-gel samples containing W110A TeSADH (0.43 mg) and NADP+ (3.0 mg) encapsulated in sol gel, 1a (0.34 mmol), 2-propanol (600 mL), and 2.0 mL solvent.

[b]% conversion was determined by GC.

[c]ee values were determined by chiral stationary-phase GC for the corresponding acetate derivative.[24]

[d]50 mm Tris-HCl buffer solution, pH 8.0 (3.5 mL) and 2-propanol (1.5 mL).

[e]50 mm Tris-HCl buffer solution, pH 8.0 (1.5 mL), CH3CN (1.5 mL), and 2-propanol (600 mL).

TABLE 2

Asymmetric reduction of phenyl-ring-containing ketones by using xerogel W110A TeSADH in organic solvents.[a,b]

| n | R | Solvent | Conv. [%][c,d] | ee [%][c,e] |
|---|---|---|---|---|
| 1 | Ph(CH$_2$)$_2$ | | 74 (99) | 97 (>99) |
| 2 | PhOCH$_2$ | | >99 (>99) | >99 (>99) |
| 3 | p-MeOC$_6$H$_4$(CH$_2$)$_2$ | | 61 (87) | 94 (91) |
| 4 | PhCH$_2$ | hexane | 80 (95) | 69 (37) |
|   | PhCH$_2$ | toluene | 24 | 55 |
|   | PhCH$_2$ | diisopropyl ether | 37 | 73 |
|   | PhCH$_2$ | tert-butyl alcohol | 38 | 63 |
| 5 | p-MeOC$_6$H$_4$CH$_2$ | | 67 (97) | >99 (>99) |
| 6 | (see structure under table heading) | | 94 (>99) | 76 (71) |

[a]Reactions were performed at 50° C. by using W110A TeSADH (0.43 mg) and NADP+ (3.0 mg) encapsulated in xerogel, substrate (0.34 mmol), 2-propanol (600 mL), and 2.0 mL hexane.
[b]The absolute configuration was determined as described previously.[14a]
[c]Results of reduction with free W110A TeSADH in 50 mm Tris-HCl buffer solution (pH 8.0)/2-propanol (70:30 v/v) are given in parentheses [14a].
[d]% conversion was determined by GC.
[e]ee values were determined by chiral stationary-phase GC for the corresponding acetate derivative.[24; herein incorporated by reference].

The following references for this Example are all herein incorporated by reference:

[1] Thayer, Chem. Eng. News 2006, 86(33), 15-25;
[2] a) Garcia-Urdiales, et al, Chem. Rev. 2005, 105, 313-354; b) Kroutil, et al, Curr. Opin. Chem. Biol. 2004, 8, 120-126; c) Nakamura, et al, Tetrahedron: Asymmetry 2003, 14, 2659-2681; d) Carrea, et al, Angew. Chem. 2000, 112, 2312-2341; Angew. Chem. Int. Ed. 2000, 39, 2226-2254;
[3] a) Cao, et al, Curr. Opin. Biotechnol. 2003, 14, 387-394; b) Gervais, et al, Biotechnol. Prog. 2003, 19, 389-395;
[4] a) Vera-Avila, et al, J. Sol-Gel Sci. Technol. 2004, 30, 197-204; b) Gelman, et al, J. Am. Chem. Soc. 2002, 124, 14 460-14463; c) Reetz, et al, Biotechnol. Bioeng. 1996, 49, 527-534;
[5] Ellerby, et al, Science 1992, 255, 1113-1115;
[6] a) Zhu, et al, J. Org. Chem. 2006, 71, 4202-4205; b) Stampfer, et al, J. Org. Chem. 2003, 68, 402-406; c) Yadav, et al, J. Org. Chem. 2002, 67, 3900-3903; d) Schubert, et al, Angew. Chem. 2002, 41, 656-659; Angew. Chem. Int. Ed. 2002, 41, 634-636; e) Heiss, et al, J. Chem. Soc. Perkin Trans. 1 2000, 2821-2825;
[7] a) Klibanov, Curr. Opin. Biotechnol. 2003, 14, 427-431; b) Klibanov, Nature 2001, 409, 241-246; c) P. Jonsson, et al, Biochim. Biophys. Acta 1999, 1430, 313-322;
[8] Grunwald, et al, J. Am. Chem. Soc. 1986, 108, 6732-6734;
[9] a) Burdette, et al, Biochem. J. 1994, 302, 163-170; b) Burdette, et al, Biochem. J. 1996, 316, 115-122;
[10] In unpublished results, Laivenieks, et al, showed that TeSADH was identical to that from *Thermoanaerobium brockii* (TBADH); [1,1] a) Pham, et al, J. Am. Chem. Soc. 1990, 112, 3629-3632; b) Pham, et al, J. Am. Chem. Soc. 1989, 111, 1935-1936;
[12] a) Heiss, et al, J. Chem. Soc. Perkin Trans. 1 2000, 2821-2825; b) Heiss, et al, Bioorg. Med. Chem. 2001, 9, 1659-1666;
[13] Prelog, Pure Appl. Chem. 1964, 9, 119-130;
[14] a) Musa, et al, J. Org. Chem. 2007, 72, 30-34; b) Ziegelmann-Fjeld, et al, Prot. Eng. Des. Sel. 2007, 20, 47-55;
[15] Gröger, et al, Org. Lett. 2003, 5, 173-176;
[16] Obert, et al, J. Am. Chem. Soc. 1999, 121, 12192-12193;
[17] Johnson, et al, Pharmacotherapy 2000, 20, 622-628;
[18] a) When the same sol-gel sample was reused without adding NADP+, a 10% conversion was achieved in the second reaction compared with 56% when new NADP+ was added, b) About 65% by weight of the xerogel was water after 24 h drying in air, c) the inventors noticed that the xerogel loses its activity after drying for a longer time (i.e. more than four days). However, the hydrogel was stable at room temperature for longer times as this enzyme has long-term stability;

[19] Fitzpatrick, et al, J. Am. Chem. Soc. 1991, 113, 3166-3171;
[20] Villela Filho, et al, Angew. Chem. 2003, 115, 3101-3104; Angew. Chem. Int. Ed. 2003, 42, 2993-2996;
[21] Schmitke, et al, Proc. Natl. Acad. Sci. USA 1998, 95, 12918-12923;
[22] Phillips, J. Mol. Catal. B 2002, 19-20, 103-107;
[23] Heiss, et al, J. Am. Chem. Soc. 2001, 123, 345-346;
[24] Ghanem, et al, Tetrahedron: Asymmetry 2003, 14, 57-62; and
[25] King, et al, J. Am. Chem. Soc. 1951, 73, 4911-4915.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in medicine, biochemistry, chemistry, molecular biology, microbiology or related fields are intended to be within the scope of the following claims.

We claim:

1. An isolated nucleic acid having the sequence as set forth in SEQ ID NO:02, wherein said nucleic acid encodes a protein having alcohol dehydrogenase activity.

2. An isolated nucleic acid having the sequence as set forth in SEQ ID NO:04.

3. An isolated nucleic acid having the sequence as set forth in SEQ ID NO:06.

* * * * *

UNITED STATES PATENT AND TRADEMARK OFFICE
CERTIFICATE OF CORRECTION

| | | |
|---|---|---|
| PATENT NO. | : 7,750,135 B2 | Page 1 of 1 |
| APPLICATION NO. | : 11/881690 | |
| DATED | : July 6, 2010 | |
| INVENTOR(S) | : Gregory J. Zeikus et al. | |

It is certified that error appears in the above-identified patent and that said Letters Patent is hereby corrected as shown below:

In the Specification

In column 1, lines 6-9, please delete:

"Aspects of this disclosure were accomplished in part with government support under Grant Award MCB-0445750 and 0445511 from the National Science Foundation. As such, the United States Government may have certain rights."

and insert:

-- STATEMENT REGARDING FEDERALLY SPONSORED RESEARCH OR DEVELOPMENT

This invention was made with government support under MCB0445750 awarded by the National Science Foundation. The government has certain rights in the invention. --

Signed and Sealed this
Twenty-ninth Day of July, 2014

Michelle K. Lee
*Deputy Director of the United States Patent and Trademark Office*

SEQUENCE LISTING

<160> NUMBER OF SEQ ID NOS: 19

<210> SEQ ID NO 1
<211> LENGTH: 352
<212> TYPE: PRT
<213> ORGANISM: Thermoanaerobacter ethanolicus

<400> SEQUENCE: 1

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Ala Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Asp Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
```

-continued

```
                    245                 250                 255
Lys Pro Gly Gly Thr Ile Ala Asn Val Asn Tyr Phe Gly Glu Gly Glu
                260                 265                 270

Val Leu Pro Val Pro Arg Leu Glu Trp Gly Cys Gly Met Ala His Lys
            275                 280                 285

Thr Ile Lys Gly Gly Leu Cys Pro Gly Gly Arg Leu Arg Met Glu Arg
        290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
                340                 345                 350

<210> SEQ ID NO 2
<211> LENGTH: 1056
<212> TYPE: DNA
<213> ORGANISM: Thermoanaerobacter ethanolicus
<220> FEATURE:
<221> NAME/KEY: misc_feature
<222> LOCATION: (328)..(330)
<223> OTHER INFORMATION: nnn at these positions are gct or gcc or gca
      or gcg
<220> FEATURE:
<221> NAME/KEY: misc_feature
<222> LOCATION: (556)..(558)
<223> OTHER INFORMATION: nnn at these positions are gat or gac

<400> SEQUENCE: 2
atgaaaggtt ttgcaatgct cagtatcggt aaagttggct ggattgagaa ggaaaagcct      60
gctcctggcc catttgatgc tattgtaaga cctctagctg tggccccttg cacttcggac     120
attcataccg tttttgaagg agccattggc gaaagacata acatgatact cggtcacgaa     180
gctgtaggtg aagtagttga agtaggtagt gaggtaaaag attttaaacc tggtgatcgc     240
gttgttgtgc cagctattac ccctgattgg cggacctctg aagtacaaag aggatatcac     300
cagcactccg gtggaatgct ggcaggcnnn aaattttcga atgtaaaaga tggtgttttt     360
ggtgaatttt ttcatgtgaa tgatgctgat atgaatttag cacatctgcc taaagaaatt     420
ccattggaag ctgcagttat gattcccgat atgatgacca ctggttttca cggagctgaa     480
ctggcagata tagaattagg tgcgacggta gcagttttgg gtattggccc agtaggtctt     540
atggcagtcg ctggtnnnaa attgcgtgga gccggaagaa ttattgccgt aggcagtaga     600
ccagtttgtg tagatgctgc aaaatactat ggagctactg atattgtaaa ctataaagat     660
ggtcctatcg aaagtcagat tatgaatcta actgaaggca aggtgtcga tgctgccatc      720 atcgctggag gaaatgctga cattatggct acagcagtta agattgttaa acctggtggc     780
accatcgcta atgtaaatta ttttggcgaa ggagaggttt gcctgttcc tgtcttgaa       840 tggggttgcg gcatggctca taaaactata aaaggcgggc tatgccccgg tggacgtcta     900
agaatggaaa gactgattga ccttgttttt tataagcctg tcgatccttc taagctcgtc     960
actcacgttt tccagggatt tgacaatatt gaaaaagcct ttatgttgat gaaagacaaa    1020
ccaaaagacc taatcaaacc tgttgtaata ttagca                              1056

<210> SEQ ID NO 3
<211> LENGTH: 352
<212> TYPE: PRT
<213> ORGANISM: Thermoanaerobacter ethanolicus
```

<400> SEQUENCE: 3

```
Met Lys Gly Phe Ala Met Leu Ser Ile Gly Lys Val Gly Trp Ile Glu
1               5                   10                  15
Lys Glu Lys Pro Ala Pro Gly Pro Phe Asp Ala Ile Val Arg Pro Leu
                20                  25                  30
Ala Val Ala Pro Cys Thr Ser Asp Ile His Thr Val Phe Glu Gly Ala
            35                  40                  45
Ile Gly Glu Arg His Asn Met Ile Leu Gly His Glu Ala Val Gly Glu
        50                  55                  60
Val Val Glu Val Gly Ser Glu Val Lys Asp Phe Lys Pro Gly Asp Arg
65                  70                  75                  80
Val Val Val Pro Ala Ile Thr Pro Asp Trp Arg Thr Ser Glu Val Gln
                85                  90                  95
Arg Gly Tyr His Gln His Ser Gly Gly Met Leu Ala Gly Ala Lys Phe
            100                 105                 110
Ser Asn Val Lys Asp Gly Val Phe Gly Glu Phe His Val Asn Asp
        115                 120                 125
Ala Asp Met Asn Leu Ala His Leu Pro Lys Glu Ile Pro Leu Glu Ala
    130                 135                 140
Ala Val Met Ile Pro Asp Met Met Thr Thr Gly Phe His Gly Ala Glu
145                 150                 155                 160
Leu Ala Asp Ile Glu Leu Gly Ala Thr Val Ala Val Leu Gly Ile Gly
                165                 170                 175
Pro Val Gly Leu Met Ala Val Ala Gly Ala Lys Leu Arg Gly Ala Gly
            180                 185                 190
Arg Ile Ile Ala Val Gly Ser Arg Pro Val Cys Val Asp Ala Ala Lys
        195                 200                 205
Tyr Tyr Gly Ala Thr Asp Ile Val Asn Tyr Lys Asp Gly Pro Ile Glu
    210                 215                 220
Ser Gln Ile Met Asn Leu Thr Glu Gly Lys Gly Val Asp Ala Ala Ile
225                 230                 235                 240
Ile Ala Gly Gly Asn Ala Asp Ile Met Ala Thr Ala Val Lys Ile Val
                245                 250                 255
Lys Pro Gly Gly Thr Ile Ala Asn Val Asn Tyr Phe Gly Glu Gly Glu
            260                 265                 270
Val Leu Pro Val Pro Arg Leu Glu Trp Gly Cys Gly Met Ala His Lys
        275                 280                 285
Thr Ile Lys Gly Gly Leu Cys Pro Gly Gly Arg Leu Arg Met Glu Arg
    290                 295                 300
Leu Ile Asp Leu Val Phe Tyr Lys Arg Val Asp Pro Ser Lys Leu Val
305                 310                 315                 320
Thr His Val Phe Arg Gly Phe Asp Asn Ile Glu Lys Ala Phe Met Leu
                325                 330                 335
Met Lys Asp Lys Pro Lys Asp Leu Ile Lys Pro Val Val Ile Leu Ala
            340                 345                 350
```

<210> SEQ ID NO 4
<211> LENGTH: 1056
<212> TYPE: DNA
<213> ORGANISM: Thermoanaerobacter ethanolicus
<220> FEATURE:
<221> NAME/KEY: misc_feature
<222> LOCATION: (328)..(330)
<223> OTHER INFORMATION: nnn at these positions are gct or gcc or gca or gcg

<400> SEQUENCE: 4

```
atgaaaggtt ttgcaatgct cagtatcggt aaagttggct ggattgagaa ggaaaagcct    60
gctcctggcc catttgatgc tattgtaaga cctctagctg tggccccttg cacttcggac   120
attcataccg tttttgaagg agccattggc gaaagacata acatgatact cggtcacgaa   180
gctgtaggtg aagtagttga agtaggtagt gaggtaaaag attttaaacc tggtgatcgc   240
gttgttgtgc cagctattac ccctgattgg cggacctctg aagtacaaag aggatatcac   300
cagcactccg gtggaatgct ggcaggcnnn aaattttcga atgtaaaaga tggtgttttt   360
ggtgaatttt ttcatgtgaa tgatgctgat atgaatttag cacatctgcc taaagaaatt   420
ccattggaag ctgcagttat gattcccgat atgatgacca ctggttttca cggagctgaa   480
ctggcagata tagaattagg tgcgacggta gcagttttgg gtattggccc agtaggtctt   540
atggcagtcg ctggtgccaa attgcgtgga gccggaagaa ttattgccgt aggcagtaga   600
ccagtttgtg tagatgctgc aaaatactat ggagctactg atattgtaaa ctataaagat   660
ggtcctatcg aaagtcagat tatgaatcta actgaaggca aggtgtcga tgctgccatc   720
atcgctggag aaatgctga cattatggct acagcagtta agattgttaa acctggtggc   780
accatcgcta atgtaaatta ttttggcgaa ggagaggttt tgcctgttcc tcgtcttgaa   840
tggggttgcg gcatggctca taaaactata aaggcgggc tatgccccgg tgacgtcta    900
agaatggaaa gactgattga ccttgttttt tataagcctg tcgatccttc taagctcgtc   960
actcacgttt tccagggatt tgacaatatt gaaaaagcct ttatgttgat gaaagacaaa  1020
ccaaaagacc taatcaaacc tgttgtaata ttagca                            1056
```

<210> SEQ ID NO 5
<211> LENGTH: 352
<212> TYPE: PRT
<213> ORGANISM: Thermoanaerobacter ethanolicus

<400> SEQUENCE: 5

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175
```

```
Pro Val Gly Leu Met Ala Val Ala Gly Asp Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Gly Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350

<210> SEQ ID NO 6
<211> LENGTH: 1056
<212> TYPE: DNA
<213> ORGANISM: Thermoanaerobacter ethanolicus

<400> SEQUENCE: 6
atgaaaggtt ttgcaatgct cagtatcggt aaagttggct ggattgagaa ggaaaagcct    60
gctcctggcc catttgatgc tattgtaaga cctctagctg tggccccttg cacttcggac   120
attcataccg tttttgaagg cgccattggc gaaagacata acatgatact cggtcacgaa   180
gctgtaggtg aagtagttga agtaggtagt gaggtaaaag attttaaacc tggtgatcgc   240
gttgttgtgc cagctattac ccctgattgg cggacctctg aagtacaaag aggatatcac   300
cagcactccg gtgaatgct ggcaggctgg aaattttcga atgtaaaaga tggtgttttt   360
ggtgaatttt ttcatgtgaa tgatgctgat atgaatttag cacatctgcc taaagaaatt   420
ccattggaag ctgcagttat gattcccgat atgatgacca ctggttttca cggagctgaa   480
ctggcagata tagaattagg tgcgacggta gcagttttgg gtattggccc agtaggtctt   540
atggcagtcg ctggtgacaa attgcgtgga gccggaagaa ttattgccgt aggcagtaga   600
ccagtttgtg tagatgctgc aaaatactat ggagctactg atattgtaaa ctataaagat   660
ggtcctatcg aaagtcagat tatgaatcta actgaaggca aggtgtcga tgctgccatc   720 atcgctggag gaaatgctga cattatggct acagcagtta agattgttaa acctggtggc   780
accatcgcta atgtaaatgg ttttggcgaa ggagaggttt tgcctgttcc tcgtcttgaa   840
tggggttgcg gcatggctca taaaactata aaaggcgggc tatgccccgg tggacgtcta   900
agaatggaaa gactgattga ccttgttttt tataagcgtg tcgatccttc taagctcgtc   960
actcacgttt tccggggatt tgacaatatt gaaaaagcct ttatgttgat gaaagacaaa  1020
ccaaaagacc taatcaaacc tgttgtaata ttagca                            1056

<210> SEQ ID NO 7
```

<211> LENGTH: 353
<212> TYPE: PRT
<213> ORGANISM: Thermoanaerobacter ethanolicus

<400> SEQUENCE: 7

Met Met Lys Gly Phe Ala Met Leu Ser Ile Gly Lys Val Gly Trp Ile
1               5                   10                  15

Glu Lys Glu Lys Pro Ala Pro Gly Pro Phe Asp Ala Ile Val Arg Pro
            20                  25                  30

Leu Ala Val Ala Pro Cys Thr Ser Asp Ile His Thr Val Phe Glu Gly
        35                  40                  45

Ala Ile Gly Glu Arg His Asn Met Ile Leu Gly His Glu Ala Val Gly
    50                  55                  60

Glu Val Val Glu Val Gly Ser Glu Val Lys Asp Phe Lys Pro Gly Asp
65                  70                  75                  80

Arg Val Val Val Pro Ala Ile Thr Pro Asp Trp Arg Thr Ser Glu Val
                85                  90                  95

Gln Arg Gly Tyr His Gln His Ser Gly Gly Met Leu Ala Gly Trp Lys
            100                 105                 110

Phe Ser Asn Val Lys Asp Gly Val Phe Gly Glu Phe His Val Asn
        115                 120                 125

Asp Ala Asp Met Asn Leu Ala His Leu Pro Lys Glu Ile Pro Leu Glu
130                 135                 140

Ala Ala Val Met Ile Pro Asp Met Met Thr Thr Gly Phe His Gly Ala
145                 150                 155                 160

Glu Leu Ala Asp Ile Glu Leu Gly Ala Thr Val Ala Val Leu Gly Ile
                165                 170                 175

Gly Pro Val Gly Leu Met Ala Val Ala Gly Ala Lys Leu Arg Gly Ala
            180                 185                 190

Gly Arg Ile Ile Ala Val Gly Ser Arg Pro Val Cys Val Asp Ala Ala
        195                 200                 205

Lys Tyr Tyr Gly Ala Thr Asp Ile Val Asn Tyr Lys Asp Gly Pro Ile
    210                 215                 220

Glu Ser Gln Ile Met Asn Leu Thr Glu Gly Lys Gly Val Asp Ala Ala
225                 230                 235                 240

Ile Ile Ala Gly Gly Asn Ala Asp Ile Met Ala Thr Ala Val Lys Ile
                245                 250                 255

Val Lys Pro Gly Gly Thr Ile Ala Asn Val Asn Tyr Phe Gly Glu Gly
            260                 265                 270

Glu Val Leu Pro Val Pro Arg Leu Glu Trp Gly Cys Gly Met Ala His
        275                 280                 285

Lys Thr Ile Lys Gly Gly Leu Cys Pro Gly Gly Arg Leu Arg Met Glu
    290                 295                 300

Arg Leu Ile Asp Leu Val Phe Tyr Lys Arg Val Asp Pro Ser Lys Leu
305                 310                 315                 320

Val Thr His Val Phe Arg Gly Phe Asp Asn Ile Glu Lys Ala Phe Met
                325                 330                 335

Leu Met Lys Asp Lys Pro Lys Asp Leu Ile Lys Pro Val Val Ile Leu
            340                 345                 350

Ala

<210> SEQ ID NO 8
<211> LENGTH: 1056
<212> TYPE: DNA
<213> ORGANISM: Thermoanaerobacter ethanolicus

<400> SEQUENCE: 8

```
atgaaaggtt ttgcaatgct cagtatcggt aaagttggct ggattgagaa ggaaaagcct      60
gctcctggcc catttgatgc tattgtaaga cctctagctg tggccccttg cacttcggac     120
attcataccg tttttgaagg agccattggc gaaagacata acatgatact cggtcacgaa     180
gctgtaggtg aagtagttga agtaggtagt gaggtaaaag attttaaacc tggtgatcgc     240
gttgttgtgc cagctattac ccctgattgg cggacctctg aagtacaaag aggatatcac     300
cagcactccg gtggaatgct ggcaggctgg aaattttcga atgtaaaaga tggtgttttt     360
ggtgaatttt ttcatgtgaa tgatgctgat atgaatttag cacatctgcc taaagaaatt     420
ccattggaag ctgcagttat gattcccgat atgatgacca ctggttttca cggagctgaa     480
ctggcagata tagaattagg tgcgacggta gcagttttgg gtattggccc agtaggtctt     540
atggcagtcg ctggtgccaa attgcgtgga gccggaagaa ttattgccgt aggcagtaga     600
ccagtttgtg tagatgctgc aaaatactat ggagctactg atattgtaaa ctataaagat     660
ggtcctatcg aaagtcagat tatgaatcta actgaaggca aaggtgtcga tgctgccatc     720
atcgctggag gaaatgctga cattatggct acagcagtta agattgttaa acctggtggc     780
accatcgcta atgtaaatta ttttggcgaa ggagaggttt tgcctgttcc tcgtcttgaa     840
tggggttgcg gcatggctca taaaactata aaggcgggc tatgccccgg tggacgtcta     900
agaatggaaa gactgattga ccttgttttt tataagcctg tcgatccttc taagctcgtc     960
actcacgttt tccagggatt tgacaatatt gaaaagcct ttatgttgat gaaagacaaa    1020
ccaaaagacc taatcaaacc tgttgtaata ttagca                              1056
```

<210> SEQ ID NO 9
<211> LENGTH: 352
<212> TYPE: PRT
<213> ORGANISM: Thermoanaerobacter ethanolicus

<400> SEQUENCE: 9

```
Met Lys Gly Phe Ala Met Leu Ser Ile Gly Lys Val Gly Trp Ile Glu
1               5                   10                  15

Lys Glu Lys Pro Thr Pro Gly Pro Phe Asp Ala Ile Val Arg Pro Leu
            20                  25                  30

Ala Val Ala Pro Cys Thr Ser Asp Val His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Ile Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Glu Ile Glu Leu Gly Ala Thr Val Ala Val Leu Gly Ile Gly
                165                 170                 175
```

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asn Gly Pro Ile Glu
        210                 215                 220

Ser Gln Ile Met Asp Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Asp
            260                 265                 270

Val Leu Pro Val Pro Arg Leu Glu Trp Gly Cys Gly Met Ala His Lys
        275                 280                 285

Ala Ile Lys Gly Gly Leu Cys Pro Gly Gly Arg Leu Arg Met Glu Arg
        290                 295                 300

Leu Ile Asp Leu Val Phe Tyr Lys Arg Val Asp Pro Ser Lys Leu Val
305                 310                 315                 320

Thr His Val Phe Gln Gly Phe Asp Asn Ile Glu Lys Ala Leu Met Leu
                325                 330                 335

Met Lys Asp Lys Pro Lys Asp Leu Ile Lys Pro Val Val Ile Leu Ala
            340                 345                 350

<210> SEQ ID NO 10
<211> LENGTH: 352
<212> TYPE: PRT
<213> ORGANISM: Thermoanaerobacter brockii

<400> SEQUENCE: 10

Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys

```
                195                 200                 205
Tyr Tyr Gly Ala Thr Asp Ile Val Asn Tyr Lys Asp Gly Pro Ile Glu
        210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350

<210> SEQ ID NO 11
<211> LENGTH: 1059
<212> TYPE: DNA
<213> ORGANISM: Thermoanaerobacter brockii

<400> SEQUENCE: 11
atgaaaggtt ttgcaatgct cagtatcggt aaagttggct ggattgagaa ggaaaagcct      60
gctcctggcc catttgatgc tattgtaaga cctctagctg tggccccttg cacttcggac     120
attcataccg tttttgaagg cgccattggc gaaagacata acatgatact cggtcacgaa     180
gctgtaggtg aagtagttga agtaggtagt gaggtaaaag attttaaacc tggtgatcgc     240
gttgttgtgc cagctattac ccctgattgg cggacctctg aagtacaaag aggatatcac     300
cagcactccg gtggaatgct ggcaggctgg aaattttcga atgtaaaaga tggtgttttt     360
ggtgaatttt ttcatgtgaa tgatgctgat atgaatttag cacatctgcc taaagaaatt     420
ccattggaag ctgcagttat gattcccgat atgatgacca ctggttttca cggagctgaa     480
ctggcagata tagaattagg tgcgacggta gcagttttgg gtattggccc agtaggtctt     540
atggcagtcg ctggtgccaa attgcgtgga gccggaagaa ttattgccgt aggcagtaga     600
ccagtttgtg tagatgctgc aaaatactat ggagctactg atattgtaaa ctataaagat     660
ggtcctatcg aaagtcagat tatgaatcta actgaaggca aggtgtcga tgctgccatc     720
atcgctggag gaaatgctga cattatggct acagcagtta agattgttaa acctggtggc     780
accatcgcta atgtaaatta ttttggcgaa ggagaggttt tgcctgttcc tcgtcttgaa     840
tggggttgcg gcatggctca taaaactata aaggcgggc tatgccccgg tggacgtcta     900
agaatggaaa gactgattga ccttgttttt tataagcgtg tcgatccttc taagctcgtc     960
actcacgttt tccgggggatt tgacaatatt gaaaaagcct ttatgttgat gaaagacaaa    1020
ccaaaagacc taatcaaacc tgttgtaata ttagcataa                            1059

<210> SEQ ID NO 12
<211> LENGTH: 374
<212> TYPE: PRT
<213> ORGANISM: Equus caballus
```

<400> SEQUENCE: 12

```
Ser Thr Ala Gly Lys Val Ile Lys Cys Lys Ala Ala Val Leu Trp Glu
1               5                   10                  15

Glu Lys Lys Pro Phe Ser Ile Glu Val Glu Val Ala Pro Pro Lys
            20                  25                  30

Ala His Glu Val Arg Ile Lys Met Val Ala Thr Gly Ile Cys Arg Ser
        35                  40                  45

Asp Asp His Val Val Ser Gly Thr Leu Val Thr Pro Leu Pro Val Ile
    50                  55                  60

Ala Gly His Glu Ala Ala Gly Ile Val Glu Ser Ile Gly Glu Gly Val
65                  70                  75                  80

Thr Thr Val Arg Pro Gly Asp Lys Val Ile Pro Leu Phe Thr Pro Gln
                85                  90                  95

Cys Gly Lys Cys Arg Val Cys Lys His Pro Glu Gly Asn Phe Cys Leu
            100                 105                 110

Lys Asn Asp Leu Ser Met Pro Arg Gly Thr Met Gln Asp Gly Thr Ser
            115                 120                 125

Arg Phe Thr Cys Arg Gly Lys Pro Ile His His Phe Leu Gly Thr Ser
130                 135                 140

Thr Phe Ser Gln Tyr Thr Val Val Asp Glu Ile Ser Val Ala Lys Ile
145                 150                 155                 160

Asp Ala Ala Ser Pro Leu Glu Lys Val Cys Leu Ile Gly Cys Gly Phe
                165                 170                 175

Ser Thr Gly Tyr Gly Ser Ala Val Lys Val Ala Lys Val Thr Gln Gly
            180                 185                 190

Ser Thr Cys Ala Val Phe Gly Leu Gly Gly Val Gly Leu Ser Val Ile
        195                 200                 205

Met Gly Cys Lys Ala Ala Gly Ala Ala Arg Ile Ile Gly Val Asp Ile
210                 215                 220

Asn Lys Asp Lys Phe Ala Lys Ala Lys Glu Val Gly Ala Thr Glu Cys
225                 230                 235                 240

Val Asn Pro Gln Asp Tyr Lys Lys Pro Ile Gln Glu Val Leu Thr Glu
                245                 250                 255

Met Ser Asn Gly Gly Val Asp Phe Ser Phe Glu Val Ile Gly Arg Leu
            260                 265                 270

Asp Thr Met Val Thr Ala Leu Ser Cys Cys Gln Glu Ala Tyr Gly Val
        275                 280                 285

Ser Val Ile Val Gly Val Pro Pro Asp Ser Gln Asn Leu Ser Met Asn
    290                 295                 300

Pro Met Leu Leu Leu Ser Gly Arg Thr Trp Lys Gly Ala Ile Phe Gly
305                 310                 315                 320

Gly Phe Lys Ser Lys Asp Ser Val Pro Lys Leu Val Ala Asp Phe Met
                325                 330                 335

Ala Lys Lys Phe Ala Leu Asp Pro Leu Ile Thr His Val Leu Pro Phe
            340                 345                 350

Glu Lys Ile Asn Glu Gly Phe Asp Leu Leu Arg Ser Gly Glu Ser Ile
        355                 360                 365

Arg Thr Ile Leu Thr Phe
    370
```

<210> SEQ ID NO 13
<211> LENGTH: 1761
<212> TYPE: DNA
<213> ORGANISM: Equus caballus

<400> SEQUENCE: 13

```
gaaaacggca tcatgagcac agcaggaaaa gtaataaaat gcaaagcggc tgtgctgtgg      60
gaggaaaaga aaccattttc catcgaggag gtggaggttg cacccccgaa ggcccatgaa     120
gtccgtataa agatggtggc cacaggaatt tgtcgctcag atgaccacgt ggttagtgga     180
acccttgtca cacctcttcc tgtgatcgca ggccatgagg cagcgggcat tgtggagagc     240
attggagaag gcgtcactac agtaagacca ggtgataaag tcatcccact ctttactccc     300
cagtgtggaa aatgcagggt ttgtaagcac cctgaaggca acttctgctt gaaaaatgat     360
ctgagcatgc ctcggggaac catgcaggat ggtaccagca ggttcacctg cagagggaag     420
cccatccacc acttccttgg caccagcacc ttctcccagt acaccgtggt ggacgagatc     480
tcagtggcca agatcgatgc ggcctcaccg ctggagaaag tctgtctcat tggctgtgga     540
ttttctactg ttatgggtc tgcagtcaag gttgccaagg tcacccaggg ctccacctgt      600
gccgtgtttg gccttggagg agtgggcctg tctgttatca tgggctgtaa agcagccgga     660
gcggccagga tcattgggt ggacatcaac aaagacaagt tgcaaaggc caaagaagtg       720
ggtgccactg agtgtgtcaa ccctcaggac tacaagaaac ccatccagga ggtgctgaca     780
gaaatgagca atggaggtgt ggatttttcc tttgaagtca ttggtcggct cgacactatg     840
gtgactgcct tgtcatgctg tcaagaagca tatggtgtga gcgtcattgt gggagtacct     900
cctgattccc aaaatctctc tatgaatcct atgttgctac tgagtggacg tacctggaaa     960
ggagctattt ttgcggttt taagagtaaa gattctgtcc ccaaacttgt ggccgatttt    1020
atggctaaaa agtttgcact ggatccttta atcacccatg ttttaccttt tgaaaaaata    1080
aatgaaggat ttgacctgct tcgctctgga gagagtatcc gtaccatcct gacgttttga    1140
gaccatacaa atgtctgcac ttgtagccgt cttctggctc ctctatcctc tggatcatca    1200
gccaaacgac atcaataatt ctgttcctca agatgctat taatagttac cgctgggagc     1260
tttctaaaag aaacaaaaat tgatgtgaag tcacttttca agcaaacgtt taaaatccaa    1320
gtgagagcta gaggaaccat cagctgggta actgagccca ctaaactttc cttcttaatc    1380
attctcctca cgttgaatcc tgtcaccttt cccattgagg aaggcatgt gttttgactt     1440
cttgcatgat ttgtatcttg gcacccctta gtattgaagc cggggtggg gggtcctcat     1500
gatacttgcc cctcagcata cacgtgatgg gctattgtgc tctaagcctt ctccttctac    1560
atgcatttcc actgtctgta tttgccttt gatgaaggta acaaggtcgc acagtaaaat     1620
acagtctgtg aaagatact ctcggattta aagtggaga aggtctagaa cttctaaatg      1680
cagggaattt cttaggaaaa tgtcatacat ctttataagg tggagggaaa tgtctttatc    1740
gcttttatac tgttggcagt g                                             1761
```

<210> SEQ ID NO 14
<211> LENGTH: 35
<212> TYPE: DNA
<213> ORGANISM: Artificial Sequence
<220> FEATURE:
<223> OTHER INFORMATION: Synthetic

<400> SEQUENCE: 14

```
atcaatatgt catatgatga aaggttttgc aatgc                                35
```

<210> SEQ ID NO 15
<211> LENGTH: 26
<212> TYPE: DNA

```
<213> ORGANISM: Artificial Sequence
<220> FEATURE:
<223> OTHER INFORMATION: Synthetic

<400> SEQUENCE: 15
cattcgaaaa tttcgcgcct gccagc                                          26

<210> SEQ ID NO 16
<211> LENGTH: 27
<212> TYPE: DNA
<213> ORGANISM: Artificial Sequence
<220> FEATURE:
<223> OTHER INFORMATION: Synthetic

<400> SEQUENCE: 16
aggaccatct ttagggttta caatatc                                         27

<210> SEQ ID NO 17
<211> LENGTH: 26
<212> TYPE: DNA
<213> ORGANISM: Artificial Sequence
<220> FEATURE:
<223> OTHER INFORMATION: Synthetic

<400> SEQUENCE: 17
gctggcaggc gcgaaatttt cgaatg                                          26

<210> SEQ ID NO 18
<211> LENGTH: 27
<212> TYPE: DNA
<213> ORGANISM: Artificial Sequence
<220> FEATURE:
<223> OTHER INFORMATION: Synthetic

<400> SEQUENCE: 18
gatattgtaa accctaaaga tggtcct                                         27

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19
gtcatctcga gtgctaatat tacaacaggt ttg                                  33
```